US012691456B2

(12) United States Patent
Yossifon et al.

(10) Patent No.: US 12,691,456 B2
(45) Date of Patent: Jul. 28, 2026

(54) SYSTEM AND METHOD FOR MANIPULATING OBJECTS IN A FLUID

(71) Applicant: Ramot at Tel-Aviv University Ltd., Tel-Aviv (IL)

(72) Inventors: Gilad Yossifon, Mazkeret Batia (IL); Yue Wue, Haifa (IL); Sinwook Park, Haifa (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 1074 days.

(21) Appl. No.: 17/440,216

(22) PCT Filed: Mar. 17, 2020

(86) PCT No.: PCT/IL2020/050317
§ 371 (c)(1),
(2) Date: Sep. 17, 2021

(87) PCT Pub. No.: WO2020/188563
PCT Pub. Date: Sep. 24, 2020

(65) Prior Publication Data
US 2022/0161275 A1 May 26, 2022

Related U.S. Application Data

(60) Provisional application No. 62/819,649, filed on Mar. 17, 2019.

(51) Int. Cl.
| | |
|---|---|
| *B03C 5/00* | (2006.01) |
| *B03C 1/01* | (2006.01) |
| *B03C 1/30* | (2006.01) |
| *B03C 5/02* | (2006.01) |
| *C12M 1/42* | (2006.01) |
| *C12N 13/00* | (2006.01) |
| *G01N 33/58* | (2006.01) |

(52) U.S. Cl.
CPC ............... *B03C 5/005* (2013.01); *B03C 1/01* (2013.01); *B03C 1/30* (2013.01); *B03C 5/026* (2013.01); *C12M 35/02* (2013.01); *C12N 13/00* (2013.01); *G01N 33/58* (2013.01); *B03C 2201/18* (2013.01); *B03C 2201/26* (2013.01)

(58) Field of Classification Search
CPC ............................. B03C 5/005; C12M 35/02
See application file for complete search history.

(56) References Cited

U.S. PATENT DOCUMENTS

2012/0085649 A1    4/2012  Sano et al.

FOREIGN PATENT DOCUMENTS

| WO | WO 2007/119154 | 10/2007 |
|---|---|---|
| WO | WO 2017/212475 | 12/2017 |
| WO | WO 2020/188563 | 9/2020 |

OTHER PUBLICATIONS

Zhan et al., "Low-frequency ac electroporation shows strong frequency dependence and yields comparable transfection results to dc electroporation", Journal of Controlled Release, vol. 160, pp. 570-576. (Year: 2012).*

Bai et al., "Characterization of biomechanical properties of cells through dielectrophoresis-based cell stretching and actin cytoskeleton modeling", BioMedical Engineering OnLine, vol. 16(41), pp. 1-15. (Year: 2017).*

Lyu, C., et al., "Simultaneous electroporation and dielectrophoresis in nonelectrolytic micro/nanoelectroporation", Scientific Reports, vol. 8(2481), pp. 1-13. (Year: 2018).*

Supplementary European Search Report and the European Search Opinion Dated Nov. 8, 2022 From the European Patent Office Re. Application No. 20774569.6. (10 Pages).

International Search Report and the Written Opinion Dated Jun. 23, 2020 From the International Searching Authority Re. Application No. PCT/IL2020/050317. (13 Pages).

Durdik et al. "Conceptual Design of Integrated Microfluidic System for Magnetic Cell Separation, Electroporation, and Transfection", Physica Medica, 29(5): 562-567, Published Online Dec. 21, 2012.

Hejazian et al. "Lab on a Chip for Continuous-Flow Magnetic Cell Separation", Lab on a Chip, 15(4): 959-970, Feb. 21, 2015.

Huo et al. "Analysis of Cargo Loading Modes and Capacity of an Electrically-Powered Active Carrier", Langmuir, p. 1-18, Published Online Dec. 5, 2019.

Nilsson et al. "Review of Cell and Particle Trapping in Microfluidic Systems", Analytica Chimica Acta, 649(2): 141-157, Published Online Jul. 14, 2009.

Park et al. "Individually Addressable Multi-Chamber Electroporation Platform With Dielectrophoresis and Alternating-Current-Electro-Osmosis Assisted Cell Positioning", Biomicrofluidics, 8(2): 024117-1-024117-16, Published Online Apr. 24, 2014.

Wu et al. "Active Particles as Mobile Microelectrodes for Selective Bacteria Electroporation and Transport", Science Advances, 6(5): eaay4612-1-eaay4612-12, Jan. 29, 2020.

* cited by examiner

*Primary Examiner* — Grant C Currens

(57) ABSTRACT

A method of electroporation of a biological object, comprises: introducing a carrier particle into a medium containing the biological object; applying a first electric field to the medium to induce trapping of the biological object by the carrier particle; and varying at least one parameter of the first electric field so as to induce electroporation of the biological object.

14 Claims, 44 Drawing Sheets

FIG. 2A
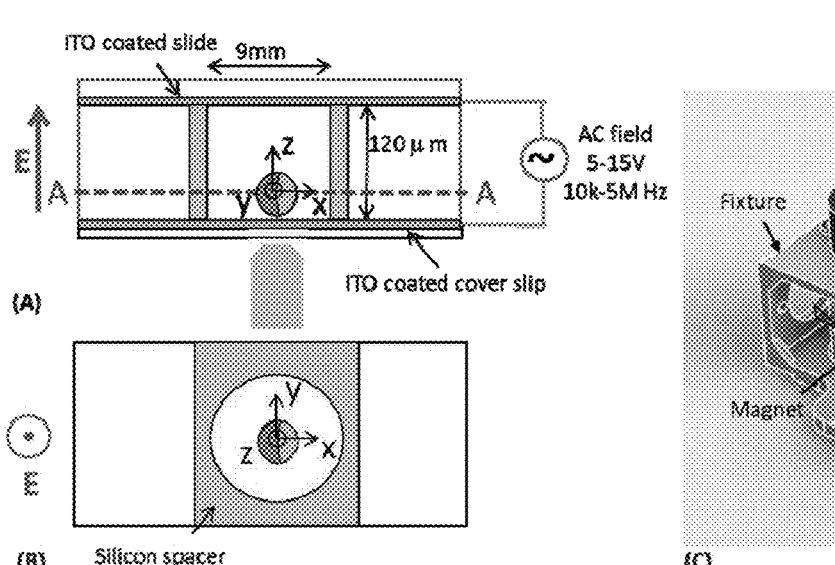
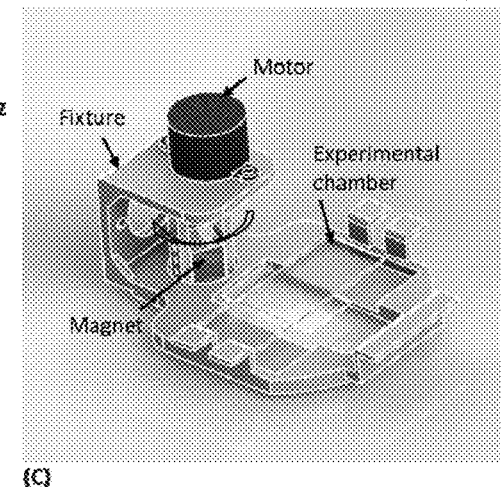
FIG. 2B                                    FIG. 2C
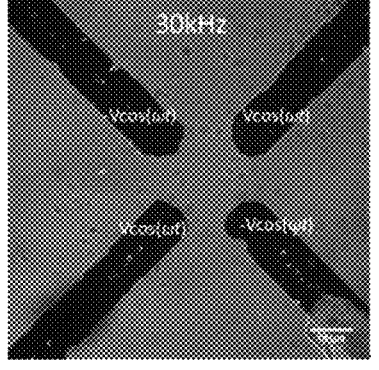
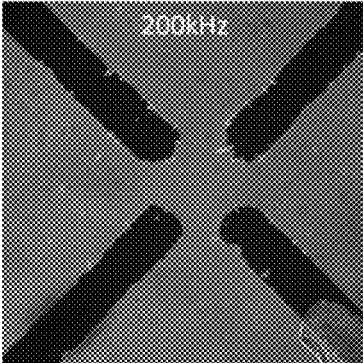
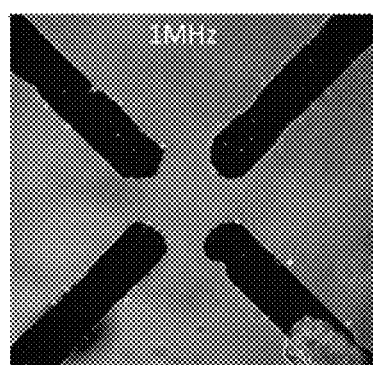
FIG. 3A                    FIG. 3B                    FIG. 3C

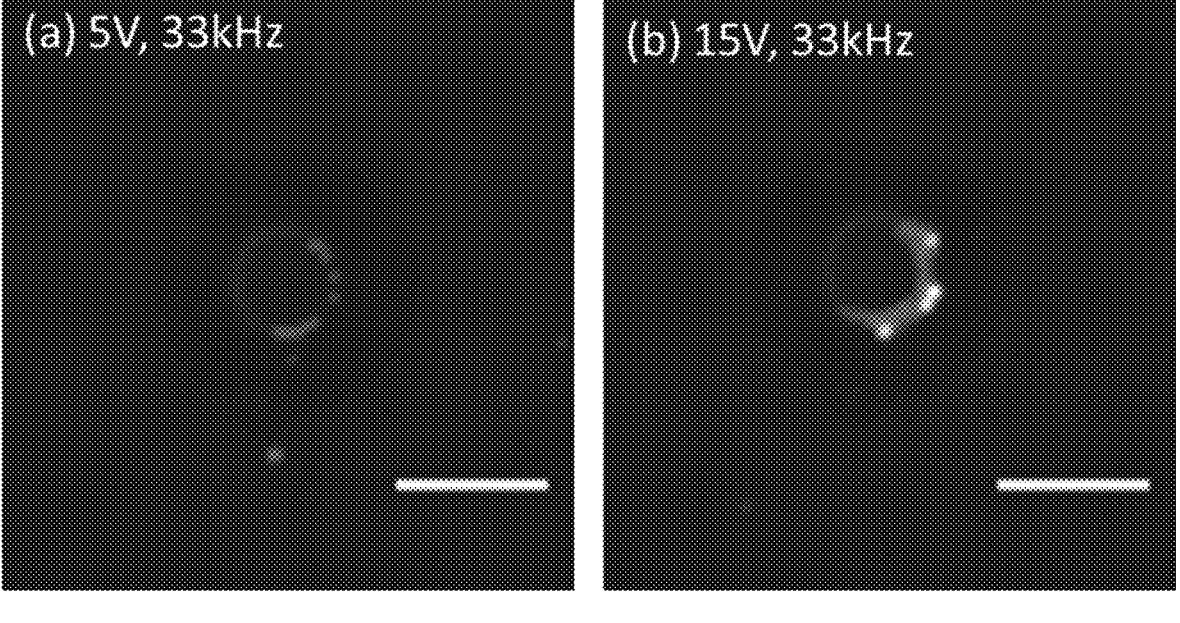
FIG. 10A                 FIG. 10B bright field　　　　fluorescent

ICEP, pDEP trapping          sDEP, nDEP trapping

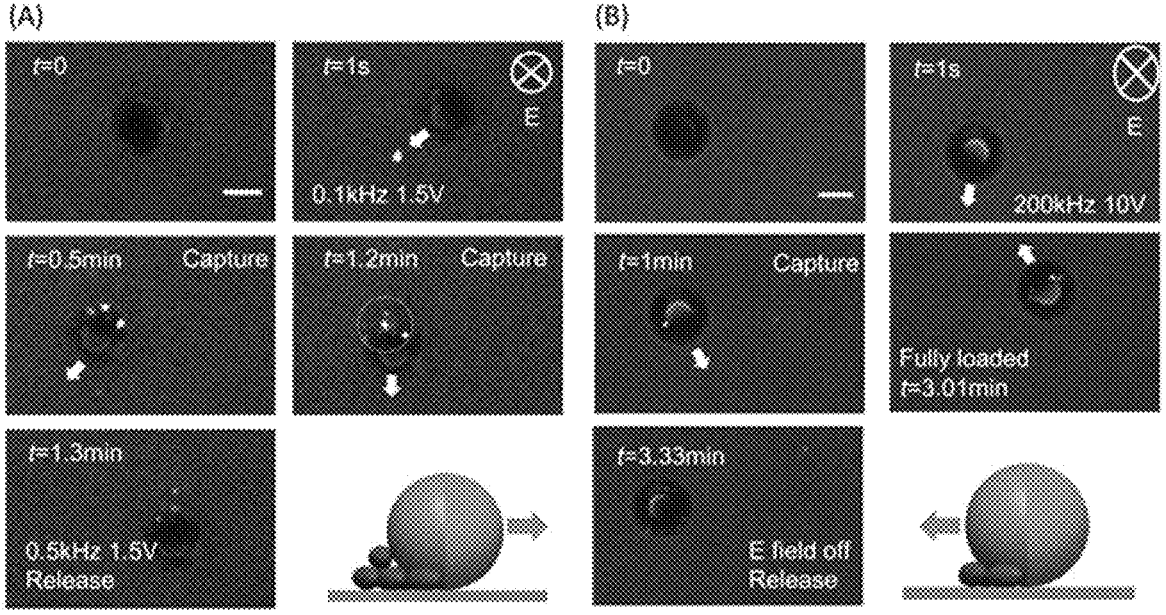
FIG. 24A                    FIG. 24B
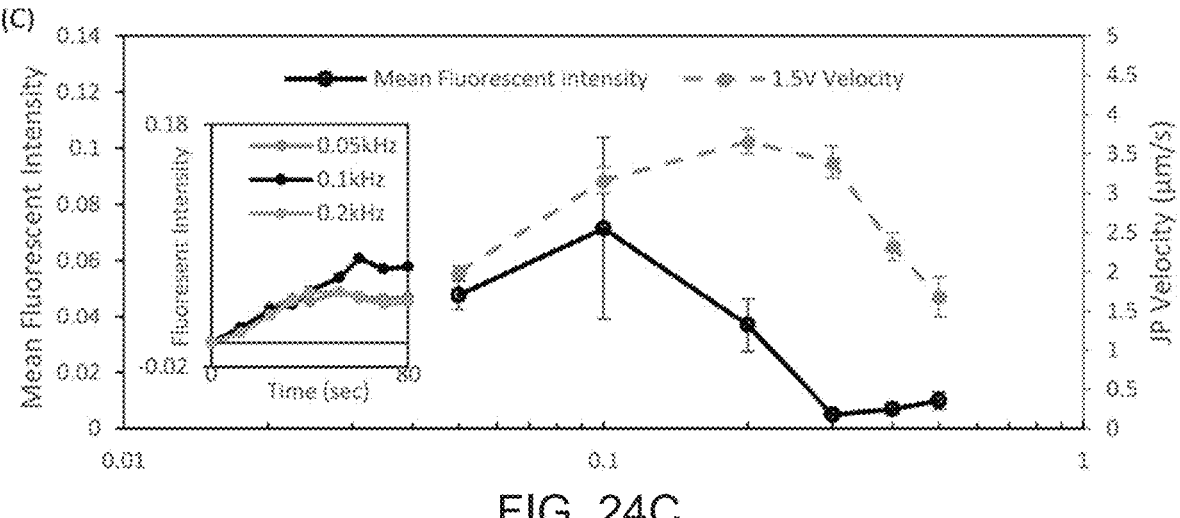
FIG. 24C

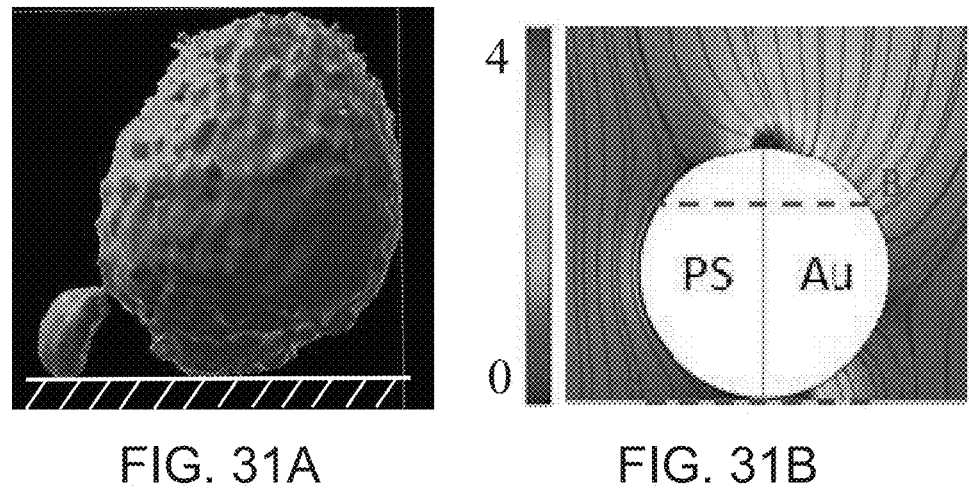
FIG. 31A                    FIG. 31B
10kHz 10V (CFDA Channel)
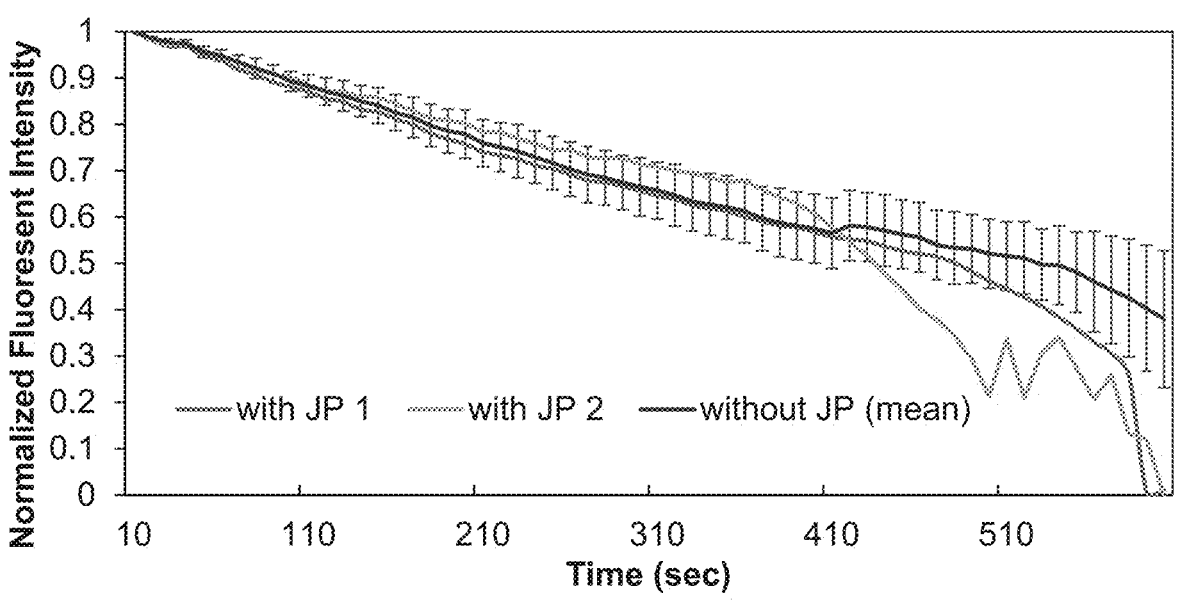
FIG. 32

FIG. 33A          FIG. 33B          FIG. 33C
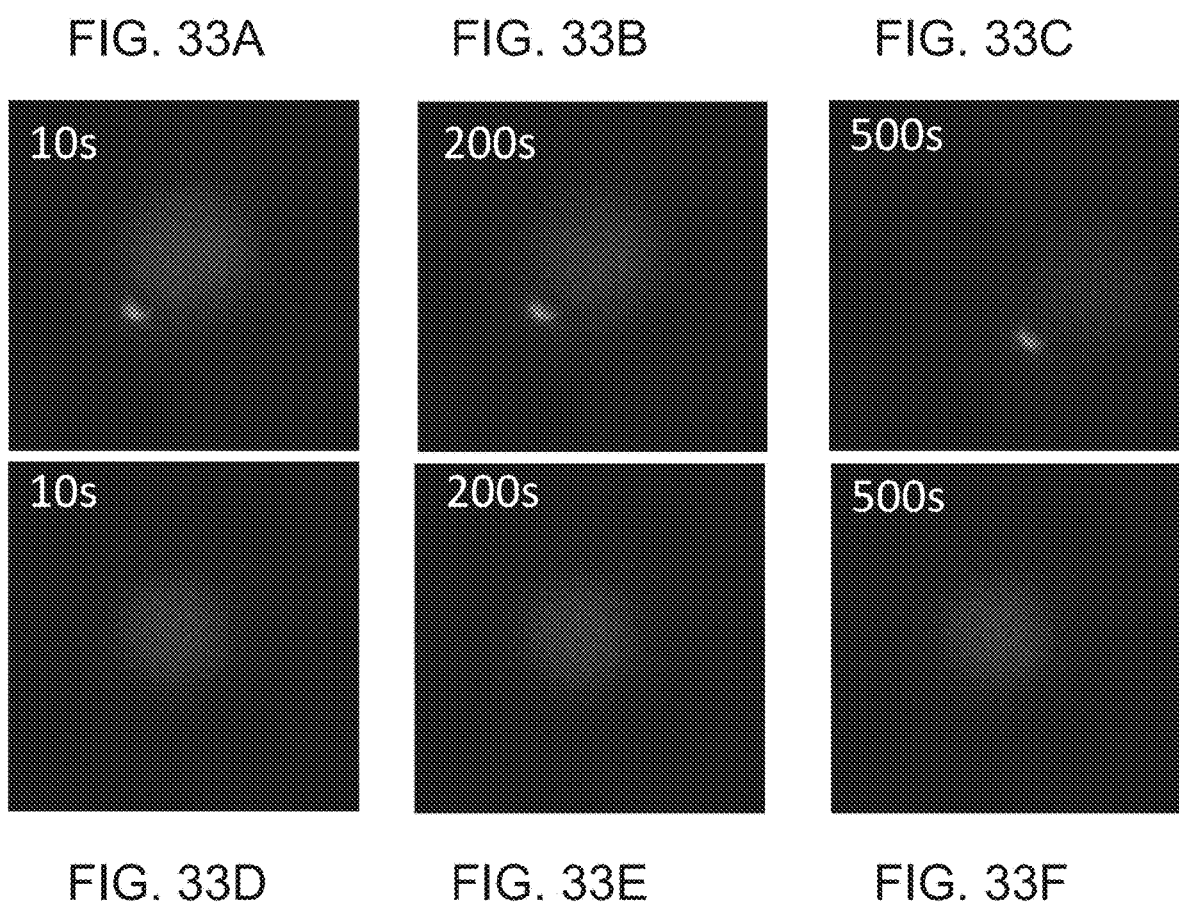
FIG. 33D          FIG. 33E          FIG. 33F
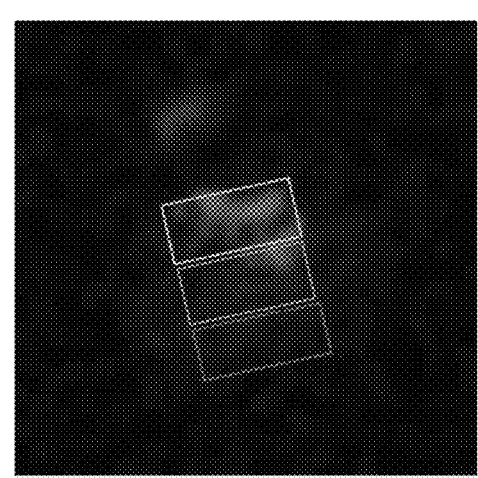
FIG. 34A

SYSTEM AND METHOD FOR MANIPULATING OBJECTS IN A FLUID

RELATED APPLICATIONS

This application is a National Phase of PCT Patent Application No. PCT/IL2020/050317 having International filing date of Mar. 17, 2020, which claims the benefit of priority under 35 USC § 119 (e) of U.S. Provisional Patent Application No. 62/819,649 filed on Mar. 17, 2019, The contents of the above applications are all incorporated by reference as if fully set forth herein in their entirety.

FIELD AND BACKGROUND OF THE INVENTION

The present invention, in some embodiments thereof, relates to object manipulation and, more particularly, but not exclusively, to a system and method for manipulating objects in a fluid.

Dielectrophoresis (DEP) is a known method of separation and concentration of both inorganic and biological matter. DEP occurs when a polarizable particle is suspended in a non-uniform electric field. The electric field polarizes the particle, and the poles then experience a force along the field lines, which can be either attractive termed positive DEP (p-DEP) or repulsive, termed negative DEP (n-DEP) according to the orientation on the dipole. The transition frequency from p-DEP to n-DEP behavior and vice versa is known as the cross-over frequency (COF) and depends on the combination of geometrical and electrical properties, e.g. conductivity or permittivity properties of both the target particle and the solution in which it is suspended. The COF corresponds exactly to when the Clausius-Mossotti (CM) factor, that combines the former electrical and geometrical parameters, vanishes. Some micro-fabricated DEP devices apply far-field electro-convection effects such as alternating-current electro-osmosis (ACEO) or induced charge electro-osmosis (ICEO) to rapidly concentrate target particles from a suspending solution to locations where they can be trapped. These DEP devices typically rely on inbuilt geometric asymmetry to induce the electric field gradients required. Some known devices embed metal electrodes to generate the spatially non-uniform, time-varying (AC) electric fields. In other known devices insulating posts are positioned in a channel of a microchip to produce the spatially non-uniform fields. Typically, active sites of known DEP devices are predetermined and prescribed by the chip design.

International Publication No. WO2017/212475 discloses a method for DEP. An electric field is applied across a micro-fluidic chamber with an alternating current (AC). The micro-fluidic chamber contains an electrolyte-solution with suspended target particles and a carrier particle freely floating on or in the electrolyte-solution. The target particles are trapped on the carrier particle based on localized gradients of the electric field induced by the carrier particle. The target particles is transported with the carrier particle from a first location in the chamber to a second location in the chamber. The trapping and the transporting is and dynamically controlled based on forces applied remotely on the carrier particle.

SUMMARY OF THE INVENTION

According to an aspect of some embodiments of the present invention there is provided a method of electroporation of a biological object. the method comprises: introducing a carrier particle into a medium containing the biological object; applying a first electric field to the medium to induce trapping of the biological object by the carrier particle; and varying at least one parameter of the first electric field so as to induce electroporation of the biological object.

According to some embodiments of the invention the varying the electric field comprises applying an electric field pulse train, in addition to the first electric field.

According to some embodiments of the invention the method comprises, following the trapping and prior to the electroporation, transporting the carrier particle and the biological object to an electroporation location.

According to some embodiments of the invention the method comprises, following the trapping and prior to the electroporation, reducing a speed of the carrier particle.

According to some embodiments of the invention the reducing the speed is to a speed of zero.

According to some embodiments of the invention the transporting comprises varying the first electric field to induce induced-charge electrophoresis or self-dielectrophoresis on the carrier particle.

According to some embodiments of the invention the transporting comprises applying a magnetic force to the carrier particle.

According to some embodiments of the invention the transporting comprises applying an optical field to the carrier particle.

According to some embodiments of the invention the carrier particle is a homogenous particle.

According to some embodiments of the invention the particle is a symmetry broken particle.

According to some embodiments of the invention the carrier particle is a Janus particle.

According to some embodiments of the invention the biological object comprises a bacterium.

According to some embodiments of the invention the biological object comprises a virus.

According to some embodiments of the invention the biological object is comprises mammalian cell.

According to some embodiments of the invention the biological object is comprises an organelle of a biological cell.

According to some embodiments of the invention the method comprises varying the electric field to deform the shape of the biological object, and probe at least one mechanical property thereof.

According to an aspect of some embodiments of the present invention there is provided a system for electroporation of a biological object. The system comprises: a fluidic chamber for receiving a medium containing the biological object, and a carrier particle; an electric field generator configured for generating electric field within the chamber, and a controller configured for controlling the electric field generator to apply a first electric field so as to induce trapping of the biological object by the carrier particle, and to vary at least one parameter of the first electric field so as to induce electroporation of the biological object.

According to some embodiments of the invention the system further comprising a fluidic delivery system for introducing the medium containing the biological object, and the carrier particle into the chamber.

According to an aspect of some embodiments of the present invention there is provided a method of labeling a target object. The method comprises: within a first medium containing a carrier particle and a labeling object that is specific to the target object, applying a first electric field to induce trapping of the functionalized object by the carrier particle, thereby providing a carrier complex including the trapped functionalized object and the carrier particle; establishing contact between a second medium containing target objects and the carrier complex, so as to allow at least one target object to specifically bind to the functionalized object; and isolating the at least one bound target object from other target objects.

According to some embodiments of the invention the trapping is by positive dielectrophoresis. According to some embodiments of the invention the trapping is by negative dielectrophoresis.

According to some embodiments of the invention the establishing contact comprises transporting the carrier complex to a chamber containing the second medium.

According to some embodiments of the invention the isolating comprises transporting the carrier complex and the at least one bound target object to a separate chamber.

According to some embodiments of the invention the transporting comprises varying the first electric field to induce induced-charge electrophoresis or self-dielectrophoresis on the carrier particle.

According to some embodiments of the invention the carrier particle comprises a magnetic coating or a magnetic core.

According to some embodiments of the invention the transporting comprises applying a magnetic force to the carrier particle.

According to some embodiments of the invention the establishing contact comprises passing the second medium through the first medium.

According to some embodiments of the invention the functionalized object is functionalized to bind the target object by means of an ionic linkage.

According to some embodiments of the invention the functionalized object is functionalized to bind the target object by means of a non-ionic linkage.

According to some embodiments of the invention the functionalized object is functionalized to bind the target object by means of a covalent bond.

According to some embodiments of the invention the functionalized object is functionalized to bind the target object by means of a non-covalent bond.

According to some embodiments of the invention the functionalized object comprises an affinity moiety selected from the group consisting of a nucleic acid, an antibody, an antigen, a receptor, a ligand, an enzyme, a substrate and an inhibitor.

According to an aspect of some embodiments of the present invention there is provided a method of separating organelles in a medium containing cell-free organelles. The method comprises: introducing a carrier particle into the medium; applying to the medium a first electric field at a frequency and amplitude selected to induce specific trapping of one type of organelle by the carrier particle thereby providing a carrier complex including the trapped organelle and the carrier particle; and isolating the carrier complex from the medium.

According to some embodiments of the invention the isolating comprises transporting the carrier complex to a separate chamber.

According to some embodiments of the invention the transporting comprises varying the first electric field to induce induced-charge electrophoresis or self-dielectrophoresis on the carrier particle.

According to some embodiments of the invention the carrier particle is magnetic.

According to some embodiments of the invention the transporting comprises applying a magnetic force to the carrier particle.

According to some embodiments of the invention the transporting comprises applying an optical field to the carrier particle.

According to some embodiments of the invention the isolating is by washing.

According to some embodiments of the invention the organelle is selected from the group consisting of mitochondria, chloroplaset, lysosome, peroxisome, golgiosome, endoplasmic reticulum, nucleus, kernel, ribosomes, microtubule, centerbody, exosome, and proteasome.

According to some embodiments of the invention the method comprises varying the electric field to deform the shape of the organelle, and probe at least one mechanical property thereof.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF SEVERAL VIEWS OF THE DRAWINGS

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-C are schematic illustrations of an experimental setup used according to some embodiments of the present invention for selective bacteria electroporation and transport.

FIGS. 3A-C are images showing positive DEP response of both CFDA (live (green fluorescent)) and PI-stained (dead (red fluorescent)) *E. coli* within a quadrupolar electrode array and solution conductivity of 9 µS/cm. At low frequency of 30 kHz the alternating-current-electro-osmotic (ACEO) flow resulted in accumulation of the bacteria on the stagnation lines at the electrodes center.

FIGS. 10A and 10B show polystyrene particles (2 µm) trapped under the metallic coated hemisphere of the JP forming a: (a) single layer under 5V and (b) multi-layer under 15V. Scale bar=5 µm.

FIGS. 18A-C show transition of cargo transport from sDEP with nDEP mode to ICEP with pDEP mode. At high frequency (500 kHz), nDEP trapped cargos (biotin-coated particles) assemble on the equator of the Janus particle and the micromotor (10 μm-diameter) and translates with its metallic (yellow color) hemisphere forward. By switching from high (500 kHz) to low frequency (5 kHz), the cargos trapped at the equator of the JP undergo pDEP trapping and the micromotor translates with its dielectric (dark grey) hemisphere forward by ICEP but with a non-smooth motion due to abrupt stops. FIGS. 18B and 18A are schematic illustrations of the trappings at 5 kHz and 500 kHz, respectively.

FIGS. 22A-E Trapping and transport of a nucleus using a Janus particle. (A) Microscope image of a Janus particle (JP) pushing a nucleus (50 kHz, 10V). Inset depicts a schematic of the side view. (B) Microscope image of a JP carrying a nucleus on its top (100 kHz, 10V). Inset depicts a schematic of the side view. (C) DEP response (i.e., velocity; positive towards the electrode edge) of the nucleus within a quadru- polar electrode army. DEP response were estimated by measuring average translational velocities between 10 and 20 μm distance from the edge of the electrode. (D) Velocity of the JP before and after trapping of the nucleus, in electrolyte solutions of low (6 μS/cm) and high (26 μS/cm) conductivities. (E) Cross-section (at the symmetry plane y-z; see also dashed red line in part B) of the trapped nucleus as obtained from the constructed three-dimensional confocal z-scans of the nucleus at various frequencies (50 kHz, 500 kHz and 3 MHz; 10V), and in low conductivity (6 μS/cm) solution. The empty region of the circle that encircles the trapped nucleus is squeezed by the JP.

FIGS. 24A-D show trapping and transport of mitochon- dria using a Janus particle. The mitochondria are always trapped between the metallic hemisphere of the Janus par- ticle (JP) and the ITO substrate. Sequential trapping of mitochondria by a 10 μm JP at: (A) 0.1 kHz and 1.5V, (B) 200 kHz and 10V. (C) Mean fluorescence intensity in the trapping area (dashed circle in part A containing most of the trapped mitochondria) at the metallic side of the JP, over a frequency range between 0.01 kHz-1 kHz. The velocity of the JP is plotted on the secondary axis. Insert: mean fluo- rescence intensity at the area of interest for frequency (0.05 kHz, 0.1 kHz and 0.2 kHz) versus operation time. (D) Number of individually trapped mitochondria within the frequency range of 10 kHz-1 MHz. The velocity of the JP is plotted on the secondary axis. Data are shown for low conductivity (6 μS/cm) solution.

FIG. 31A shows 3D reconstructed Janus particle and a mammalian cell.

FIG. 31B shows electric field surface plots and stream- lines around a Janus particle.

FIG. 32 shows normalized CFDA fluorescent intensity of JP approached and non-approached cells.

FIGS. 33A-F are microscopy images of JP approached and non-approached cells.

FIGS. 34A-C show local electroporation of Propidium iodide (PI) into a mammalian cell by a Janus particle.

DESCRIPTION OF SPECIFIC EMBODIMENTS OF THE INVENTION

Figure 1:
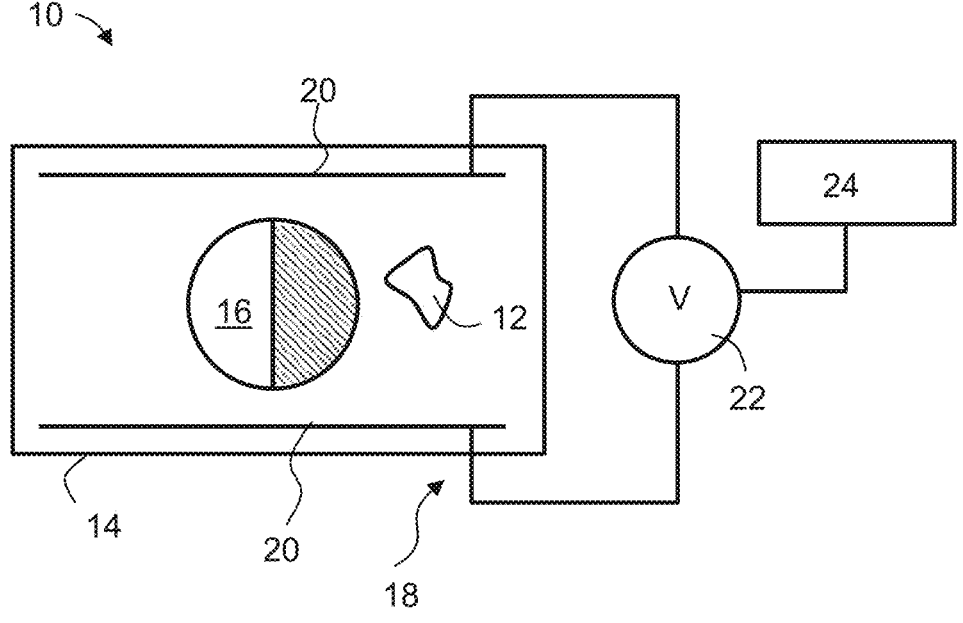
FIG. 1 is a schematic illustration of a system for electroporation of a biological object, according to some embodiments of the present invention.

The present invention, in some embodiments thereof, relates to object manipulation and, more particularly, but not exclusively, to a system and method for manipulating objects in a fluid.

Before explaining at least one embodiment of the inven- tion in detail, it is to be understood that the invention is not necessarily limited in its application to the details of con- struction and the arrangement of the components and/or methods set forth in the following description and/or illus- trated in the drawings and/or the Examples. The invention is capable of other embodiments or of being practiced or carried out in various ways.

According to some embodiments of the present invention, a first oscillatory (AC) electric field is applied across a fluidic chamber, optionally and preferably a micro-fluidic chamber, having therein a medium containing a biological object, and a carrier particle. The oscillatory electric field is optionally and preferably uniform across the chamber. The oscillatory electric field can be applied continuously or as a pulse train. The frequency, amplitude, and/or pulse parameters (when a pulse train is employed) is/are selected to induce trapping of the biological object by the carrier particle. The trapping forms a carrier complex which includes the carrier particle and the trapped biological object, wherein the biological object is attracted to the carrier particle by means of field gradients in the vicinity of the carrier particle.

Trapping can induced, for example, by applying a continuous electric field at a frequency of from about 50 kHz to about 700 kHz, more preferably from about 100 kHz to about 500 kHz, and amplitude of from about 50 V/mm to about 150 V/mm, more preferably 70 V/mm to about 120 V/mm, e.g., about 80 or about 90 V/mm. These embodiments are particularly useful when the particle is about 10 μm in diameter.

In some embodiments, the carrier particle is a symmetry broken particle. The symmetry broken particle may have symmetry broken geometric properties, such as, but not limited to, a particle doublet, a particle having a symmetry broken electrical properties, e.g., a Janus particle (JP).

The present embodiments contemplate many types of biological objects. Representative examples including, without limitation, bacteria, viruses, mammalian cells, and organelles of biological (e.g., mammalian) cell, such as, but not limited to, mitochondria, chloroplaset, lysosome, peroxisome, golgiosome, endoplasmic reticulum, nucleus, kernel, ribosomes, microtubule, centerbody, exosome, and proteasome.

When the biological object is a bacterium, a virus, a cell, or an organelle of a cell, one or parameters of the first electric field is varied so as to induce electroporation of the biological object. The varied parameters can include one or more of the frequency, amplitude, and the pulse parameters (when a pulse train is employed). In some embodiments of the present invention the electroporation is induced by applying a continuous electric field, or a pule train if electric field at a frequency which is lower than the trapping frequency. For example, when the trapping frequency is above 100 kHz, the electroporation frequency can be from about 10 kHz to about 70 kHz. The amplitude of the electric field used for the electroporation can be the same as the amplitude of the electric field used for trapping. Alternatively, the amplitude of the electric field used for the electroporation can be larger than (e.g., two or more times larger) than the amplitude of the electric field used for trapping.

Preferably, but not necessarily, the electroporation is induced by applying a pulse train of an AC or DC field, in addition to the first oscillatory electric field. In some embodiments, the speed of carrier particle is reduced, optionally and preferably to zero, before the electroporation. This can be done by selecting the parameters of the first electric field. For example, in experiments performed using a 10 μm JP, the Inventors found that an electric field at a frequency of 10-100 kHz, or 3-8 MHz can significantly reduce the speed of the JP.

In some embodiments of the present invention the carrier complex (including the carrier particle and the biological object) is transported to an electroporation location, following the trapping and prior to the electroporation. The electroporation location can be remote from the location at which the trapping occurs. For example, the electroporation location can be in a different fluidic channel or a different channel than the channel at which the trapping occurs.

Transport of the carrier complex can be effected in more than one way. According to some embodiments of the present invention, the carrier particle is a symmetry broken particle and transportation is effected by a propulsion mechanism that is induced by the localized symmetry breaking and is based on an induced-charge electro-phoresis (ICEP) or a self-DEP (s-DEP), depending on frequency of the externally applied electric field. In these embodiments, the electric field is varied to induce motion of the carrier complex via ICEP or s-DEP.

Self-DEP as used herein refers to a propulsion mechanism in which the driving gradient in the electric field for mobilizing the carrier particle is self-induced by proximity of the carrier particle to a conducting channel wall. According to some exemplary embodiments, self-DEP is induced by applying an oscillatory electric field with frequency above a pre-defined critical frequency. According to some exemplary embodiments, the critical frequency depends on the electrolyte concentration and particle radius. Optionally, ICEP may be used also to free stuck particles from the substrate, after which the frequency may be increased to induce transportation by s-DEP.

When the symmetry broken carrier particle is a metallodielectric Janus particle, self-DEP may be distinguished from ICEP by a switching of direction of the carrier particle. Under ICEP, the carrier particle typically travels with its dielectric hemisphere forwards due to stronger ICEO around the metallic hemisphere. Field gradients beneath the metallic hemisphere typically drive the carrier particle in the direction of its metallic end. A critical frequency at which a metallodielectric Janus particle switches direction represents a point just after its dipolophoretic (DIP) velocity equals zero. Such a frequency can be employed, following the transportation, so as to reduces the velocity of the particle prior to the electroporation. DIP velocity is the summation of the generally opposing DEP and ICEP velocities that operate on the carrier particle at lower frequencies.

Transport by means of DEP and ICEP can induced, for example, by applying a continuous electric field at a frequency of from about 50 kHz to about 700 kHz, more preferably from about 100 kHz to about 500 kHz, and amplitude of from about 50 V/mm to about 150 V/mm, more preferably 70 V/mm to about 120 V/mm, e.g., about 80 or about 90 V/mm. These embodiments are particularly useful when the particle is about 10 μm in diameter.

In some exemplary embodiments, taking dielectric target particles that exhibit a p-DEP to n-DEP transition with increasing frequency as an example, frequencies significantly above a frequency that induces p-DEP for target particles (and below the frequency the COF frequency that shifts to a n-DEP behavior of the target particles) is applied for a defined time period to enhance trapping of the target particles and then the frequency is reduced (within a range of p-DEP) to enhance mobilization of the carrier particle while the target particles are still trapped. In some exemplary embodiments, the carrier particles tend to mobilize at a faster rate at the lower frequency range for self-DEP, e.g. frequencies around 100 KHz. In some exemplary embodiments, an applied voltage is controlled, e.g. increased to increase trapping.

In some exemplary embodiments, the carrier particle may be symmetric and transport of the particle may be induced by an external driving force other than the electric field gradient. Optionally, adding magnetic functionalization, e.g., substituting the partial metallic coating of the particles with magnetic coating or using a carrier particle with a magnetic core enables controlling transport based on an external magnetic field in conjunction with the applied electric field. Also contemplated are embodiments in which other driving forces are applied to effect a transport. These include, but are not limited to, DC electric field, pressure field, an optical driving force, or a mechanical driving force.

The present embodiments also contemplate a technique in which the electric field and carrier particle are used for trapping a target object (e.g., a target biological object as further detailed hereinabove) via a functionalized object. In these embodiments, the first electric field is applied to a chamber having therein a first medium containing the carrier particle as further detailed hereinabove, and a functionalized object that is specific to the target object.

The functionalized object can be, in a form of, for example, a bead, a microstructure, a nanostructure or the like. The functionalized object has an affinity to the target object. According to a preferred embodiment of the present invention the functionalized object includes an affinity moiety, which is capable of binding to the target object. The affinity moiety may be, for example, a nucleic acid, an antibody, an antigen, a receptor, a ligand, an enzyme, a substrate and/or an inhibitor. The binding of the affinity moiety to the target object can be by means of an ionic linkage or a non-ionic linkage, or by means of covalent linkage or a non-covalent linkage. The affinity moiety can be adsorbed onto a surface of the functionalized object or, alternatively, it can be covalently linked to the surface of the functionalized object.

The first electric field is preferably applied to induce trapping of the functionalized object by the carrier particle, as further detailed hereinabove. This provides a carrier complex including the trapped functionalized object and the carrier particle.

Following the trapping, contact is established between a second medium containing target objects and the carrier complex. This can be done either by transporting the carrier complex to a second chamber containing the second medium, as further detailed hereinabove, or by passing the second medium with the target objects through the first medium that contains the carrier complex.

The contact between the carrier complex and the second medium, allows one of more of the target objects in the second medium to specifically bind to the functionalized object. This forms a labeled complex in which the functionalized object is trapped by the carrier and the target object(s) is/or bind to the trapped functionalized object. Following the formation of the labeled complex, the labeled complex is optionally and preferably isolated from the other target objects in the second medium. This results in a labeled that is isolated from non-labeled objects in the second medium.

The isolation of the labeled complex can be effected, for example, by washing. In these embodiments, the carrier particle is immobilized within the chamber in which the binding occurs, and a washing buffer is introduced into the chamber, removing from the chamber the second medium and the other objects. The immobilization can be by applying an electric field that ensures that the labeling complex is at rest relative to the chamber, or in embodiments in which the carrier particle is magnetic, by applying a magnetic field to immobilize the labeling complex. The immobilization can also be mechanical, for example, using a filter that allows the unbound object to wash out but prevents the labeling complex, which is typically larger since it also includes the carrier particle, from exiting the chamber.

The isolation of the labeled complex can also be effected by transporting the labeling complex to a separate chamber, as further detailed hereinabove.

The present embodiments also contemplate a technique in which the electric field and carrier particle are used for separating organelles in a medium containing cell-free organelles and optionally and preferably also to perform single cell and organelle electro-deformation. In these embodiments, a carrier particle is introduced into a medium containing cell-free organelles. In some embodiments, the carrier particle is introduced into a medium containing whole cells. In the latter embodiments, the carrier particle is first guided to a cell-of-interest (for example, under a microscope), e.g., using sDEP or ICEP, or by means of other fields, such as, but not limited to, magnetic field or optical field, as further detailed hereinabove. Once the carrier particle approaches the cell, the electric field can be varied to induce irreversible electroporation and release the organelles from the cell, thereby forming a medium containing the cell-free organelles.

Once the particle is in the medium that contains the cell-free organelles, the first electric field is applied to the medium. The frequency and amplitude of the first electric field is selected to induce specific trapping of one type of organelle by the carrier particle. The inventors found and experimentally demonstrated that different types of organelles respond differently to electric field of different frequencies and amplitudes in the presence of the carrier particle.

For example, it was found that cell nuclei can be trapped by the carrier particle when a continuous electric field is applied at a frequency of from about 100 kHz to about 500 kHz, and amplitude of from about 70 V/mm to about 100 V/mm, or from about 80 V/mm to about 90 V/mm. It was also found that cell mitochondria can be trapped by the carrier particle when a continuous electric field is applied at a frequency of from about 10 kHz to about 2 MHz, or from about 10 kHz to about 2 MHz, or from about 0.05 kHz to about 0.5 kHz, and amplitude of from about 50 V/mm to about 140 V/mm, or from about 65 V/mm to about 125V/mm. It was also found that cell lysosome can be trapped by the carrier particle when a continuous electric field is applied at a frequency of from about from about 0.05 kHz to about 0.5 kHz, or from about 10 kHz to about 120 kHz, and amplitude of from about 10 V/mm to about 200 V/mm, e.g., about 15 V/mm, or from about 20 V/mm to about 80V/mm, e.g., about 70 V/mm.

It is appreciated that the field parameters (frequency, amplitude) for trapping (e.g., via positive DEP) depends on the specific organelle and the dielectric properties medium. The skilled person having provided with the details described herein would know how to select the appropriate parameters.

Following the specific trapping of the organelle, a carrier complex including the trapped organelle and the carrier particle is formed. The carrier complex can then be isolated from the medium, as further detailed hereinabove.

Figures 21A, 21B, 21C:
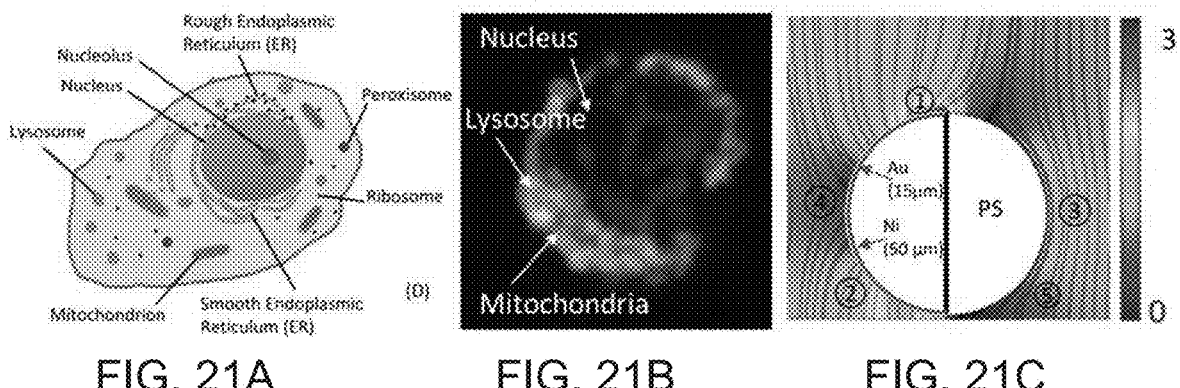
FIGS. 21A-D show mammalian cell organelles and their loading and transport modes using an active particle system. (A) Schematic of the organelles in a mammalian cell. (B) Fluorescence microscopy image of the nucleus, mitochondria and lysosome stained with the fluorescent dyes. (C) Electric field (normalized by the electric field away from the particle) surface plot and streamlines as obtained from numerical simulation. The different numbers are related to local electric field maxima (locations 1-3) and minima (locations 4,5) corresponding to pDEP and nDEP potential wells. (D) Different cargo (nucleus, mitochondrion and lysosome) loading modes versus the applied frequency. The color blocks correspond to the different manipulation strategy as indicated in the text within each of these. Data are shown for low-conductivity (6 μS/cm) solution and fixed organelles.

The Inventors found that different types of organelles may be trapped on different parts of the carrier particle (see, for example, FIG. 21B of the Examples section that follows). This phenomenon can be used for separating the organelles even when a set of electric field parameters results in trapping of more than one organelle on the same carrier particle. For example, suppose that an electric field having a frequency of about 100 kHz and amplitude of 80 V/mm is applied to a medium containing nuclei, mitochondria and lysosomes. This traps a nucleus and a mitochondrion, but not a lysosome. Thereafter the carrier complex is separated from the medium and the frequency of the electric field is varied to release, for example, the mitochondrion but not the nucleus. The carrier particle with the remaining cargo can then be transported to a different location and the remaining cargo can be released, thereby separating it from the other organelles.

The parameters (frequency and/or amplitude) of the applied electric field can also be selected for inducing a deformation on the trapped organelle. These embodiments are particularly useful for probing the mechanical properties (e.g., elastic properties) of the trapped organelle. For example, FIGS. 23A-H of the Examples section that follows demonstrate various deformations by an electric field having frequency of about 1 MHz, and different amplitudes.

FIG. 1 is a schematic illustration of a system 10 for electroporation of a biological object 12, according to some embodiments of the present invention. System 10 comprises a fluidic chamber 14 for receiving a medium containing the biological object 12, and a carrier particle 16, and an electric field generator 18 configured for generating electric field within chamber 14. Electric field generator 18 can be embodied, for example, as two conductive plates 20 connected to a voltage source. System 10 can also comprise a controller 24 having an electronic circuit for controlling electric field generator 18. In some embodiments of the present invention controller 24 is configured to apply an electric field so as to execute the technique described herein.

For example, controller 24 can be configured to apply a first electric field to induce trapping of biological object 12 by carrier particle 16, and to vary the first electric field so as to induce electroporation of biological object 12, as further detailed hereinabove. Alternatively, or additionally, controller 24 can be configured to apply a first electric field to induce trapping of a functionalized object by carrier particle 16, as further detailed hereinabove. Controller 24 can also be configured to apply a first electric field to induce trapping of a biological object (e.g. cell organelle, cell) by carrier particle 16 and perform local electro-deformation tests for mechanical probing.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Electroporation and Transport of Bacteria

This Example demonstrates selective electroporation of trapped bacteria. The selective electroporation was obtained under both continuous alternating current and pulsed signal conditions. This approach is applicable to wide range of cell types, and constitutes a tool for, for example, single-cell analysis and targeted delivery.

Introduction

The area of active particles (also termed micromotors) promises applications in drug delivery detoxification, environmental remediation, immunosensing, remote surgery, self-repairing systems, self-motile devices and more. Motion is achieved by designing particles that can asymmetrically draw and dissipate energy, creating local gradients of force for autonomous propulsion. With freedom to travel along individual path lines such particles can cover larger areas and volumes and operate under simpler ambient conditions (for example, without the necessity for field or chemical gradients) than phoretically driven particles. Active particles can be used for cargo transport (loading and translation on an active particle) and delivery (release). To date, achieving both propulsion of the active carrier and cargo manipulation (load and release) has only been possible by combining two different mechanisms; self-propulsion can be driven by e.g., electric, magnetic and optical external fields and even with chemical fuel, while cargo loading is achieved by e.g., magnetic, electrostatic, or biomolecular recognition and attraction mechanisms.

Boymelgreen et al., Nat. Commun. 9, 760 (2018) describes a unification of carrier propulsion and cargo manipulation, and demonstrates that it is possible to singularly control both processes by an applied external electric field. This unification allows for significantly simpler and more robust operation. The field gradients that can manipulate matter via dielectrophoresis (DEP) can be induced at the surface of a polarizable, freely suspended active metallodielectric Janus particle (JP) under an externally applied electric field, acting essentially as a mobile floating microelectrode. This finding offers a label-free method to selectively and dynamically manipulate (load, transport and release) a broad range of organic and inorganic cargo. The DEP force can be either attractive (positive DEP) or repulsive (negative DEP), depending on the relative polarizability of the cargo compared to the medium, which is a function of the material's inherent electrical properties and the frequency of the applied field. Thus, high (low) electric field regions can be used to selectively trap particles exhibiting positive (negative) DEP.

Combining DEP with electrically powered active particle propulsion yields an active carrier that can selectively load, transport and release a broad range of cargos, singularly controlled by an external electric field. Electric fields allow the precise tuning of the induced propulsion forces on active particles in real time and avoid issues of finite life and/or non-bio-compatibility of fuels. Furthermore, changes in the frequency of the applied electric fields can give rise to a number of distinct electrokinetic effects that can power locomotion in different ways. Under the application of a uniform alternating current (AC) electric field, metallodielectric JPs (where one hemisphere is conducting and the other dielectric) can respond as active particles, despite the external nature of the applied field. This distinctive feature arises from the propulsive mechanism, either induced-charge electrophoresis (ICEP) or self-dielectrophoresis (sDEP), which is produced on the individual particle level rather than via an externally applied global gradient. It has the advantage of being fuel-free, and mobility is greatest in aqueous electrolytes. Addition of magnetic steering, e.g., magnetizing a ferromagnetic Ni layer coated on half of the JP surface and using an external rotating static magnet, can provide directed motion and selective trapping of cells.

Unlike other techniques, the micromotor described in this Example can be applied in closed microfluidic chambers, and be externally controlled using electric and magnetic fields. Such a design offers intensification of the electric field due to the nanometer gap between the floating metallic patch and the conductive substrate. Together with its directed motion ability, using magnetic steering, the approach presented herein offers a significantly simplified and efficient method of unifying selective trapping and electroporation of cells, singularly controlled via an externally applied electric field.

In this Example, JP propulsion and cargo manipulation was operated under AC electric field conditions within the parallel indium tin oxide (ITO)-coated glass slide setup, in order to suppress the generation of the gas bubble products of the faradic reactions on the electrodes. Although DC pulses are the dominant electroporation mode, continuous AC fields can also cause cell electroporation and lysis. This Example demonstrates that the locally intensified electric field intensity and gradient at the JP level enable both selective collection of E. coli as well as effective electroporation of the cells, with a moderate voltage, using either a continuous AC field or a train of pulses for electroporation. A significantly higher electroporation rate was observed for E. coli collected by JPs, relative to untrapped E. coli, proving that the micromotor-based approach of the present embodiments allows for targeted electroporation of cells. This Example also demonstrates the application of the JP not only as a cargo carrier, but also as a platform for local electroporation of selectively trapped cells.

Methods

Magnetic Janus Particle Fabrication

Polystyrene particles (diameter: 10 μm) (Sigma Aldrich) in isopropanol (IPA) were pipetted onto a glass microscope slide, to form a monolayer of particles upon solvent evaporation. The glass slide was coated with 15 nm Cr, followed by 50 nm Ni and 15 nm Au, as described in the protocol outlined in Pethig et al., J. Electrochem. Soc. 164, B3049-B3055 (2017), and Wu et al. Science (80-.). 350, aab4077-aab4077 (2015). To magnetize the JPs, the substrates were placed in between two neodymium magnetic blocks (14× 12×19 mm in size), with opposite dipoles facing each other. Next, the substrate was sonicated in deionized water DI with 2% (v/v) Tween 20 (Sigma Aldrich) to release the JPs. The JPs were then washed three times in DI water with 0.01% (v/v) Tween 20 (Sigma Aldrich) and $7 \cdot 10^{-5}$M KCl before the experiment.

Magnetic Steering of Janus Particles

JPs were guided by placing the neodymium magnet block (14×12×19 mm in size) at a specific orientation close to the microchamber (see FIGS. 2A-C). The magnet was kept at a horizontal distance of 3 cm from the focus of the objective and at the same height as the microchamber. In this setup, the magnet produced a field of 125 Gauss in the microchamber.

Cell Culture and Preparation of Bacteria Solution

Escherichia coli (E. coli) strain XL1-Blue bacteria were cultured at 37° C. and 250 rpm in Luria-Bertani (LB) medium containing 10 g/L tryptone, 5 g/L yeast extract and 10 g/L NaCl. Electorcompetent cells were prepared when the cultures reach an OD600 of 0.5-0.7 using a glycerol method and frozen in a −80° C. freezer. To label bacteria with GFP, a pCDNA3.1-GFP plasmid was transformed to XL1-Blue competent cells by electroporation (1800 w, 0.5 ms). Cells were cultured in a LB-Agar plate with ampicillin resistance to grow as single colonies. Bacteria were picked up from a colony for experiments using a pipette tip and incubated for 5 min, at room temperature, in 200 μL DI water, which contained 33 μg/ml PI, 0.01% (v/v) Tween 20 (Sigma Aldrich) and $7 \cdot 10^{-5}$M KCl. To label the cell with CFDA, XL1-Blue bacteria (without GFP labelling) were cultured in a LB-Agar plate without ampicillin resistance to grow as a single colonies. Bacteria were picked up from a colony for experiments using a pipette tip and incubated for 30 min, at 37° C., in 0.1 mM-Phosphate buffer (pH 8.5, 5% (w/v)-NaCl, 0.5 mM-EDTA disodium salt) and 6-Carboxyfluorescein diacetate (CFDA) solution (10 mg/ml) according to manufactures' protocol. Cells were washed 3 times with DEP buffer (2385 mg (L-HEPES, 80700 mg/L-Sucrose, and 4500 mg/L-Dextrose). Before the experiment, 3 μg/ml Propidium Iodide (PI) and 0.1% Tween 20 were added into the solution. Moreover, the conductivity was adjusted to 9 μS/cm by adding KCl. Then incubated for 5 minutes at room temperature. All chemicals were purchased from Sigma-Aldrich.

*Rhodococcus Erythropolis* ATCC 4277 were cultured at 30° C. in a LB-Agar plate for 48 hours to grow as single colonies. Bacterial were picked up from a colony for experiments using a pipette tip and incubated for 30 min, at 30° C., in Phosphate-buffered saline (PBS) with 6-Carboxyfluorescein diacetate (CFDA) solution (10 mg/ml) according to manufactures' protocol. Cells were washed 3 times with DEP buffer (2385 mg/L-HEPES, 80700 mg/L-Sucrose, and 4500 mg/L-Dextrose). Before the experiment, 3 μg/ml Propidium Iodide (PI) and 0.1% Tween 20 were added into the solution. Moreover, the conductivity was adjusted to 9 μS/cm by adding KCl. Then incubated for 5 minutes at room temperature. All chemicals were purchased from Sigma-Aldrich.

Preparation of Polystyrene Tracer Particles Solution

For observation of electroconvection, a solution consisting of 0.01% (w/v) 720 nm-diameter polystyrene (PS) particles (Fluoro-max) was prepared. Particles were rinsed three times with DI water, to which a small amount (0.01% (v/v)) of nonionic surfactant (Tween 20 (Sigma Aldrich)) and $7 \cdot 10^5$M KCl were added in order to minimize adhesion to the ITO substrate before being injected into the microfluidic chamber via a small hole at the upper substrate, drilled expressly for this purpose.

Experimental Set-Up

The experimental chamber consisted of a 120 μm-high, silicone reservoir (Grace-Bio), sandwiched between an ITO-coated, 1 mm glass slide (Delta Technologies) and an ITO-coated coverslip (SPI systems), see FIGS. 3A-C. Two inlet holes (~1 mm in diameter) were drilled through the top 1 mm ITO slide, surrounded by a silicone reservoir (2 mm in height and 9 mm in diameter) filled with solution, to ensure the chamber remained wet and to enable the addition of the solution with the JPs, bacteria, fluorescent dyes and tracer particles into the channel via manual pumping. The AC electrical forcing was applied using a signal generator (Agilent 33250A) and monitored by an oscilloscope (Tektronix-TPS-2024). An AC pulse signal was applied using a signal generator (TTi TGA 12104 series) with multiple channels. A lab-made switch (Solid State Relays (AQV252G) controlled by Arduino Nano) was used to control the duration and timing of AC pulses. A power amplifier (Falco System) was used to amplify the output signal.

Selective Trapping of *E. coli* by Janus Particles and Electroporation

Figure 4A:
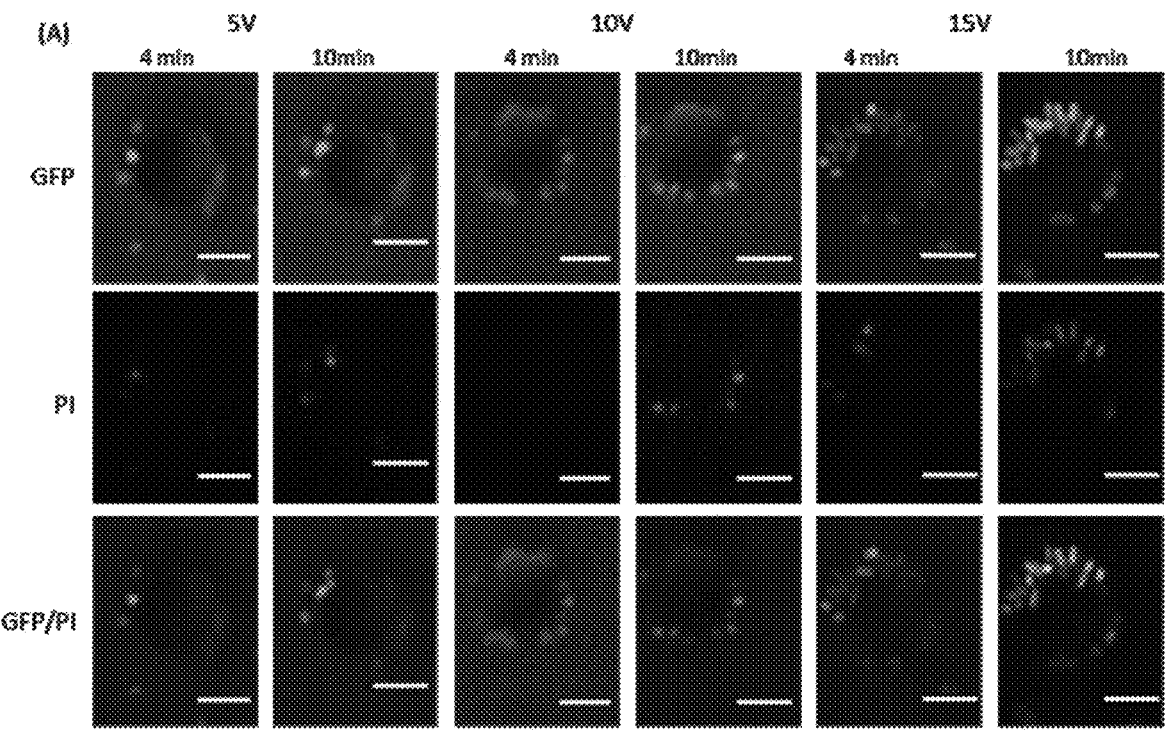
FIGS. 4A-C show microscope images of PI-stained trapped versus non-trapped *E. coli*, at low frequency (50±20 k Hz), various applied voltages, and operation times. PI uptake (red fluorescence) indicates cell electroporation. Microscopic images of (A) trapped *E. coli* and (B) untrapped *E. coli*. (C) Percentage of both trapped and un-trapped PI-stained *E. coli* over time, at various applied voltages (~33 k Hz). Error bars represent standard deviation computed from three independent tests. Janus particle of 10 µm in diameter was used. *Escherichia coli* (*E. coli*) strain XL 1-Blue bacteria with GFP labelling was used. Scale bar=5 µm.
Figure 5A:
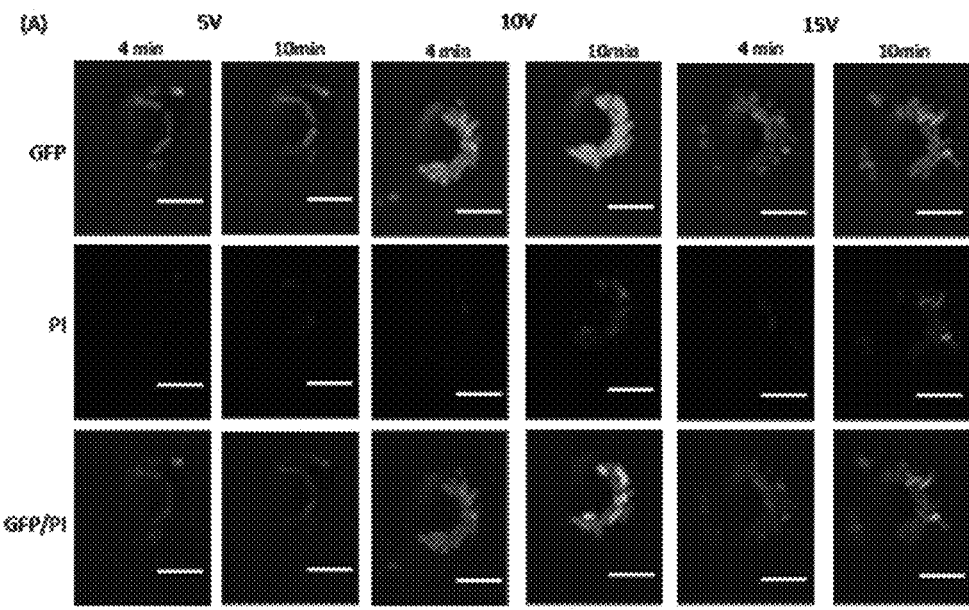
FIGS. 5A-C show microscope images of PI-stained trapped versus non-trapped *E. coli*, at high frequency (5M Hz), various applied voltages, and operation times. PI uptake (red fluorescence) indicates cell electroporation. (A) Trapped and (B) untrapped *E. coli*. (C) Percentage of both trapped and un-trapped PI-stained *E. coli*, at various applied voltages (5M Hz). Error bars represent standard deviation computed from three independent tests. Janus particle of 10 µm in diameter was used. Scale bar=5 µm. *E. coli* strain XL 1-Blue bacteria with GFP labelling was used.
Figure 5B:
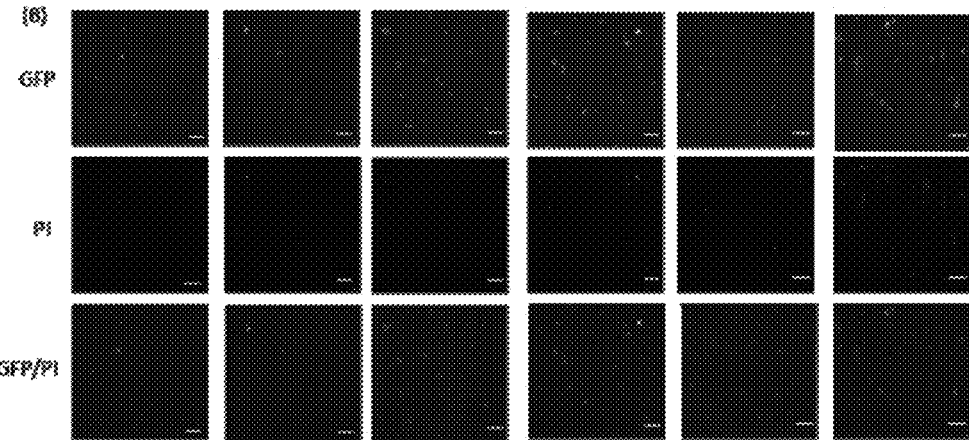
Figure 5C:
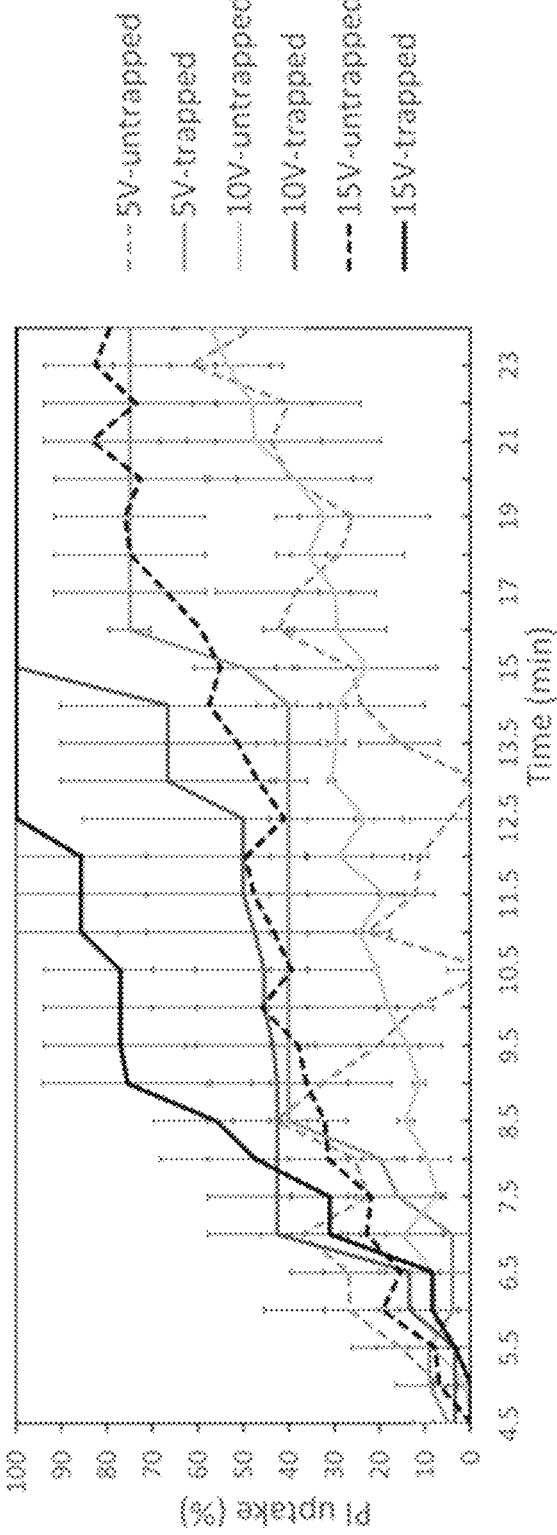

Active collection of *E. coli* was performed in the ITO chamber at 300 k Hz and 10 V, for 2 min. In the following 2 min, the electrical field parameters were changed to find the conditions (zero velocity of the JP) for the electroporation stage during which un-trapped *E. coli* diffuse away. The remaining trapped *E. coli* underwent electroporation using either continuous AC signal for different amplitudes, frequencies and durations, as depicted in FIG. 4A and FIG. 5A, or using an AC pulse train under a continuous AC signal with frequency of 5M Hz. The AC pulse train consisted of electroporation pulses (frequency: 33 k Hz, 30 V, duration: 0.5 ms) with 1 s intervals of a continuously applied electric field (frequency: 2M Hz, 10 V) for trapping purposes.

Microscopy and Image Analysis

Trapped and untrapped *E. coli* (FIG. 4A, FIG. 5A, FIGS. 6A and 6B and FIG. 7A) were observed using a Nikon Eclipse Ti-E inverted microscope equipped with a Yokagawa CSU-X1 spinning disk confocal scanner and Andor iXon-897 EMCCD camera. The chamber was placed with the coverslip side down and images were taken using an ×60 oil immersion lens. GFP and PI fluorescent dyes were observed with lasers of wavelength 488 nm and 561 nm, respectively. If the cell shows 50% fluorescent intensity of its maximum value, it was considered PI-stained. The PI uptake (FIGS. 4A-C, 5A-C, and 7C) was computed as the ratio between the number of PI-stained trapped *E. coli* and the total number of trapped *E. coli*, after subtraction of the number of PI-stained *E. coli* at minute 4. Here, again the bacteria trapped above the JP were not included.

Numerical Simulations

The numerical simulation used to qualitatively verify the presence of asymmetric electric field gradients arising from the proximity of a Janus sphere near a conducting wall, was performed in COMSOL™ 5.3. A simple 2D geometry, consisting of a rectangular channel, 50 μm height and 100 μm width, with a 10 μm diameter circle placed 300 nm above the substrate, was used to model the experimental setup. Since the EDLs are thin relative to the radius of the particle (λ/a<<1), within the electrolyte one can solve the Laplace equation for the electric potential, φ, in conjunction with the following boundary condition at the metallic side of the JP $$\sigma\frac{\partial\phi}{\partial n} = i\omega C_{DL}(\phi - V_{floating}) \qquad \text{(EQ. 1.1)}$$

which describes the oscillatory Ohmic charging of the induced EDL, wherein $V_{floating}$ is the floating potential of the metallic hemisphere of the JP, n is the coordinate in the direction of the normal to the JP surface, and $C_{DL}$ represents the capacitance per unit area of the EDL and may be estimated from the Debye-Huckel theory as $C_{DL} \sim \varepsilon/\lambda$. In addition, a floating boundary condition (21) was applied on the metallic hemisphere so as to obey total zero charge. An insulation boundary condition was applied on the dielectric hemisphere of the JP, a voltage of 6.25 V was applied at the lower substrate (y=0), while the upper wall was grounded, and the edges of the channel were given an insulating boundary condition.

Calculation of the Transmembrane Potential

The following Schwan's equation (42) was used for the approximation of the transmembrane potential of *E. coli*:

$$\Delta\psi_{membr} = 1.5aE_{appl}\cos\theta \big/ [1 + (\omega\tau)^2]^{1/2}, \qquad \text{(EQ. 1.2)}$$

$$\tau = aC_{membr}\big(\rho_{int} + \frac{\rho_{ext}}{2}\big), \qquad \text{(EQ. 1.3)}$$

where θ is the angle between the electric field direction and the normal to the cell membrane, $E_{appl}$ is the applied field strength, f is the frequency, ω=2πf is the angular frequency, a is the radius of the cell, $C_{member}$ (F/cm²) is the capacitance of the membrane, $\rho_{int}$ is the resistivity of the internal fluid, $\rho_{ext}$ is the resistivity of external medium, and τ is the membrane relaxation time. As an example, for applied voltage difference of 10 V, the calculated transmembrane potential is 0.1 V and 0.002 V, for frequencies of 33 k Hz and 5M Hz, respectively (see Table 1.1), demonstrating the decreased electroporation efficiency with increasing frequency.

TABLE 1.1

| Symbol | Explanation | value |
|---|---|---|
| $E_{appl}$ (V/cm) | Applied field strength | 833.3 |
| f (Hz) | Frequency | $33 \times 10^3$ |
|  |  | $5 \times 10^6$ |
| $\Omega$ (rad/s) | $2\pi f$ |  |
| A (cm) | Radius of the cell | $1 \times 10^{-4}$ |
| $C_{membr}$ (F/cm$^2$) | Capacitance of the membrane | $0.6 \times 10^{-6}$ |
| $\rho_{int}$ ($\Omega$ cm) | resistivity of the internal fluid | 454.55 |
| $\rho_{ext}$ ($\Omega$ cm) | Resistivity of external medium | $1.11 \times 10^5$ |
| $\tau$ ($\mu$s) | Relaxation time of membrane | 3.36 |
| $\Delta\psi_{membr}$ (V) | Transmembrane potential | 0.103 (f = $33 \cdot 10^3$ Hz) |
|  |  | 0.002 (f = $5 \cdot 10^6$ Hz) |

Result

Directed Motion-Based Selective Trapping and Release

Figures 8A, 8B, 8C, 8D, 8E, 8F:
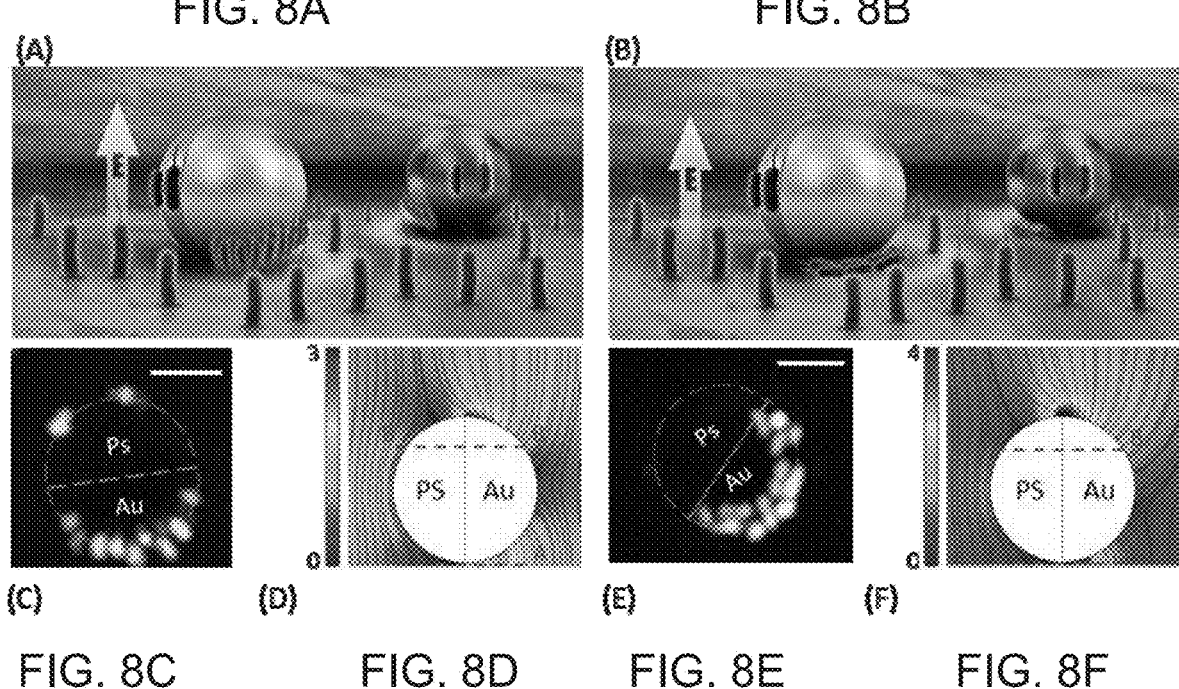
FIGS. 8A-F are schematic illustrations and images showing selective bacteria trapping and electroporation demonstrated in experiments performed according to some embodiments of the present invention. Schematic illustrations of selective bacteria transport and electroporation, using a Janus particle (JP) as a mobile microelectrode and a continuous AC electric field. The *E. coli* potentially trapped above the JP are not depicted in A and B as we were focused on visualizing only those trapped at or below the equator of the JP. (A, C, D) 50±20 k Hz and 15V, (B, E, F) 5M Hz and 15V. (C) and (E) Confocal microscope images obtained by projection of z-scans from plane A-A to B-B (as shown in (D) and (F)). The bacteria that are trapped below the JP exhibit a distinct orientation at low and high electric field frequencies. (D) and (F) are electric field surface plots and streamlines, as obtained from numerical simulations for low (f/f$_{RC}$=3) and high (f/f$_{RC}$>>1) frequencies. Scale bar=5 µm.

To study *E. coli* trapping using a metallo-dielectric Janus sphere in an experimental setup consisting of conductive (ITO-coated glass slides) top and bottom substrates, a z-scan (11 planes within 10 μm distance from ~2 μm below the substrate) of the JP was performed (see FIGS. 8C and 8E). It was found that *E. coli* were trapped at two locations: 1) between the [TO slide and the metallic side of the JP, 2) at the equator of the polystyrene side of the JP. This is in qualitative agreement with the numerical simulation results indicating that the strongest electric field and field gradients are formed in the inherent small gap between the metallic side of the JP and the wall, with smaller field and field gradients also observed at the equator of the dielectric hemisphere (FIGS. 8D and 8F). As a result, trapping was observed, due to positive DEP, at these locations. The DEP response of both live and dead bacteria at the low solution conductivity (]~9 μS/cm) at which the experiments were conducted is expected to be positive (35) and was indeed verified using the quadrupolar electrode array (FIG. 3A-C). At low frequencies (~30 kHz) alternating-current-electro-osmotic (ACEO) flow dominated the response. In some cases bacteria was also trapped above the JP due to positive DEP resulting from the local large electric field gradients existing at the metallo-dielectric interface (FIGS. 8D and 8F). However, the region of interrogation (i.e., between planes A-A and B-B) was below the top of the JP as this Example is focused on visualizing only those trapped at or below the equator of the JP It was also found that the orientations of the *E. coli* trapped in between the metallic side of the JP and the bottom substrate were distinctively different in low and high frequencies. In the low frequency regime (50±20 k Hz), the metallic side of the JP was partially screened due to the induced electrical double layer (EDL). Therefore, the electrical field outside the EDL had a non-zero tangential electric field component along which the trapped *E. coli* aligned and seemed to be "standing up" (i.e., with its major axis normal to the ITO substrate) (FIG. 8A). However, at higher frequencies (5M Hz), much beyond the relaxation time of the induced EDL ($f_{RC}=\frac{1}{2}\pi\tau$~1.6 kHz; where $\tau=\lambda a/D$ is the induced charge relaxation, $\lambda=\sqrt{\varepsilon D/\sigma}$ ~40 nm is the Debye length, a=5 μm is the radius of the JP, D~$2\cdot10^{-9}$ m$^2$/s is the diffusion coefficient of the ionic species (37), σ~9 μS/cm is the measured conductivity of the solution (37), ε~$80\varepsilon_0$ is the permittivity of water and $\varepsilon_0$ is the permittivity of the vacuum), there was not sufficient time for charging of the induced EDL, and hence, the electrical field lines were perpendicular to the non-screened metallic hemisphere. In this case, in order to fit into the small gap between the JP and the wall, the *E. coli* had to 'lie down' (i.e., with its major axis parallel to the ITO substrate) (FIG. 8B).

Figures 9A, 9B:
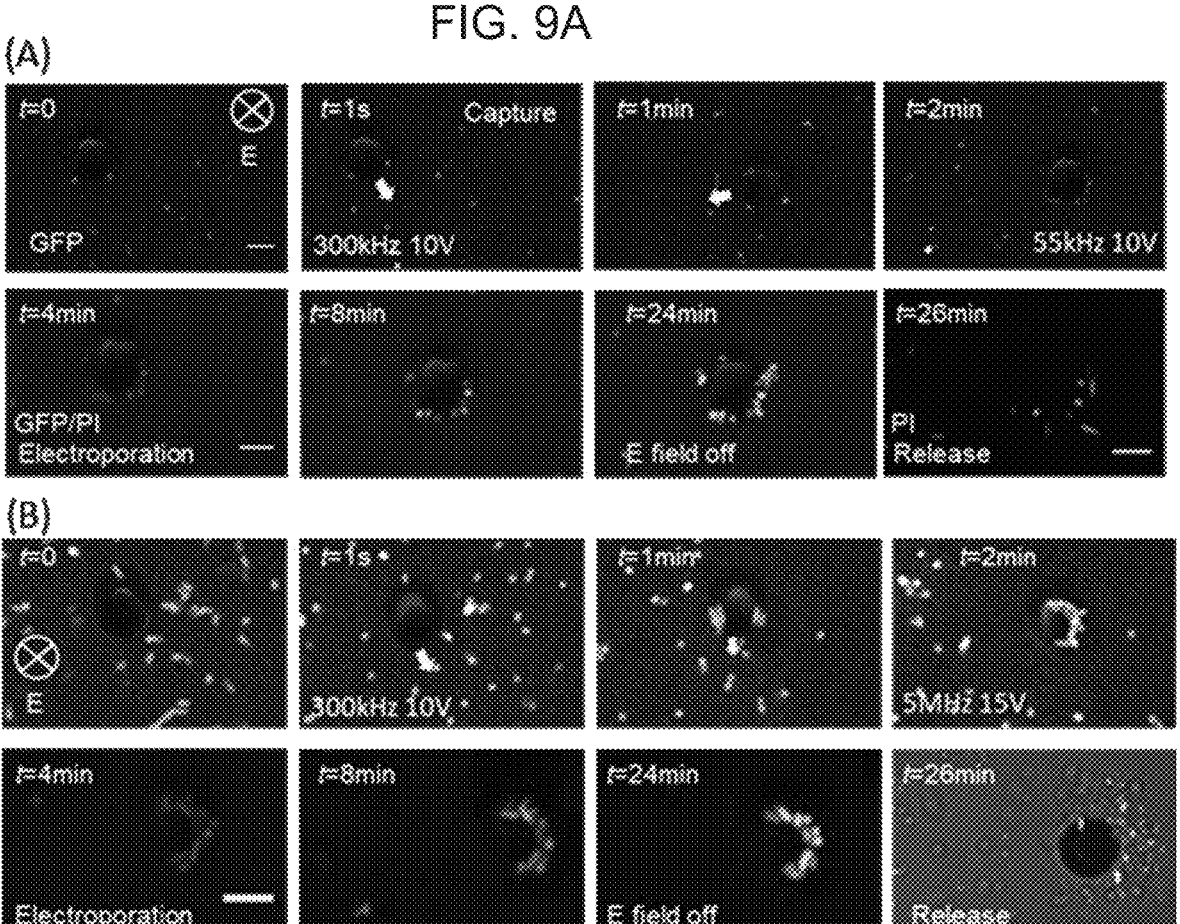
FIGS. 9A-D shows sequential trapping, electroporation and release of *E. coli*, as obtained in experiments performed according to some embodiments of the present invention. Trapping was conducted at 300 k Hz and 10 V, with a moving Janus particle (JP), while electroporation was performed at either. (A) 50±20 k Hz or (B) 5M Hz, where the JP was immobile, as evident from (C), depicting the JP particle velocity versus frequency. The applied voltage in the electroporation stage varied, but results of the case of 10 V and 15 V are shown here. (D) Number of *E. coli* trapped between the JP and the ITO glass, including at the JP equator, at the low (50±20 k Hz) and high (5M Hz) frequency regimes, for different operation times, and varying voltages. Error bars represent standard deviation computed from three independent tests. Scale bar=5 µm.
Figure 9C:
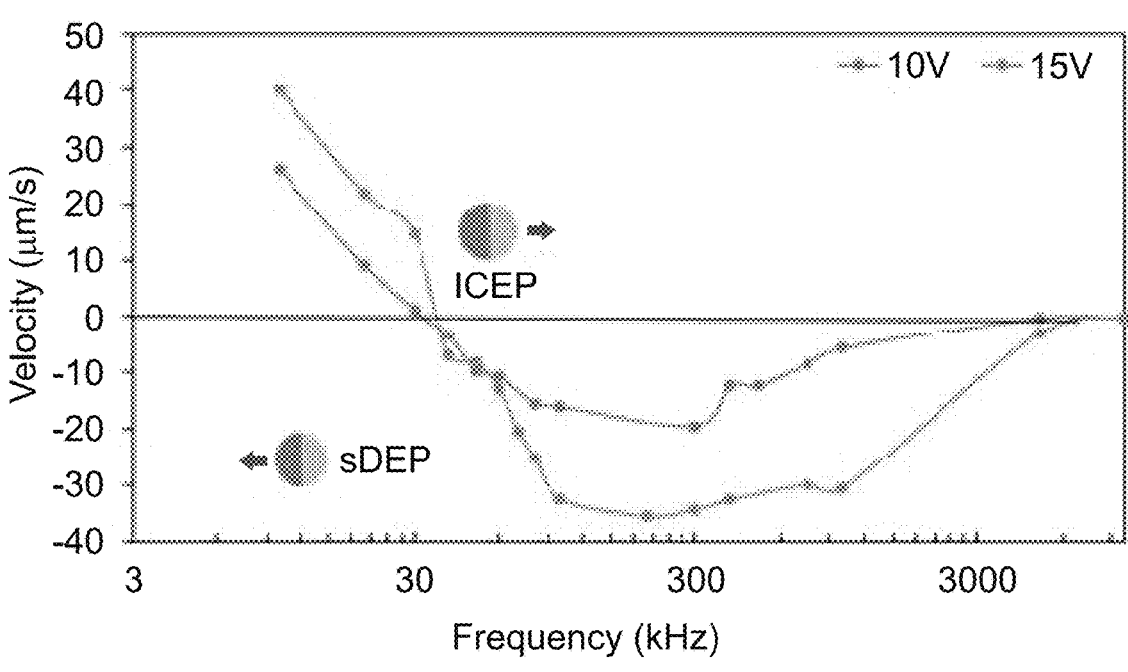

The reason for choosing these two frequencies (50±20 kHz, 5 MHz) for studying the continuous AC electroporation was because the JP propulsion velocity at these frequencies approximately vanished (FIG. 9C), which facilitated confocal z-scan imaging at a fixed location. The low frequency regime (50±20 k Hz) corresponds to the critical frequency at which the JP reverses direction from ICEP to sDEP motions. This critical frequency depends on the local conductivity of the solution, which might be affected by cytoplasm coming out from the electroporated cells, and hence varies within a range of frequencies. However, due to the low concentration of the bacteria in the solution it is not expected to be a significant effect in terms of both conductivity and molecule adsorption on the JP surface. The exact value of the frequency at which the JP velocity vanishes, which also determines the continuous AC field electroporation conditions, then needs to be determined for each test. The sequential stages of trapping, electroporation and release are described in FIGS. 9A-B. The JP first collected *E. coli* in the ITO chamber (300 kHz and 10 V, 2 min), moving at a velocity of ~20 μm/s, which is around the maximum velocity achieved in sDEP mode (FIG. 9C). After two minutes of trapping, the electrical field parameters were changed to the desired continuous AC field electroporation conditions. As a result, the outer layer of the trapped *E. coli* became un-trapped (weak DEP force relative to thermal motion) and diffused away. Propidium iodide (PI) uptake by *E. coli* was used as an indication of membrane electroporation. The electroporation efficiency, defined as the ratio of the number of electroporated cells relative to the total number of trapped cells, was below 10% during the trapping stage, which suggests the ability to carry intact biological matter and electroporate it at a second location.

Figure 9D:
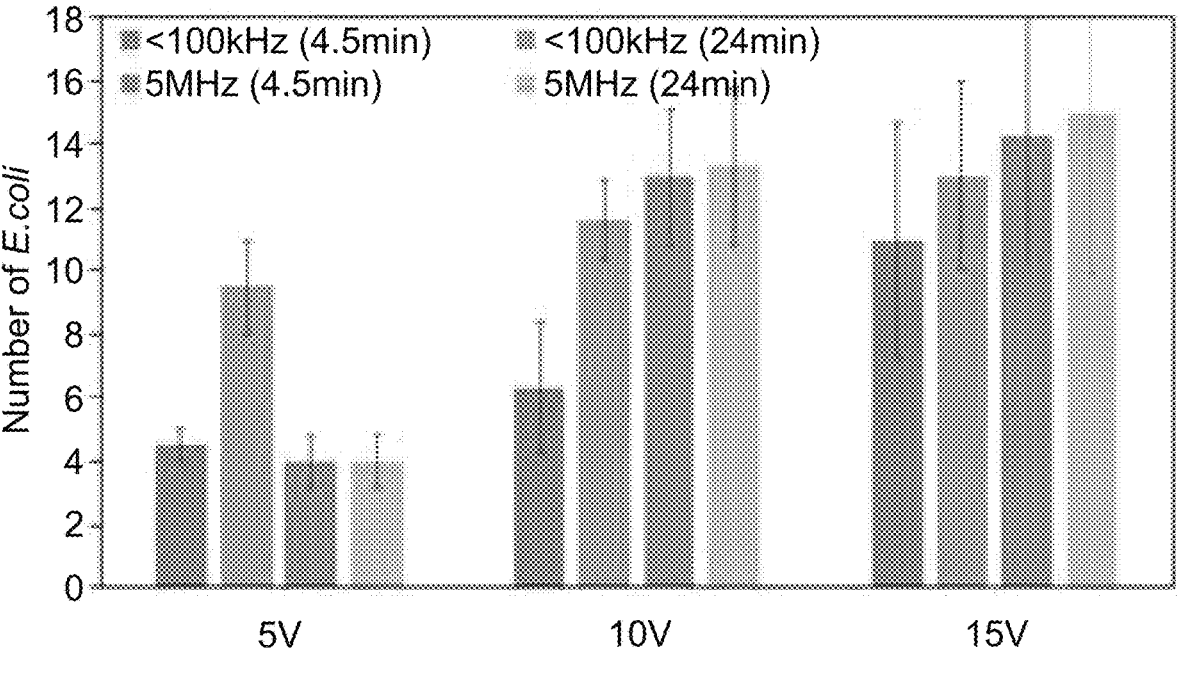
Figure 11:
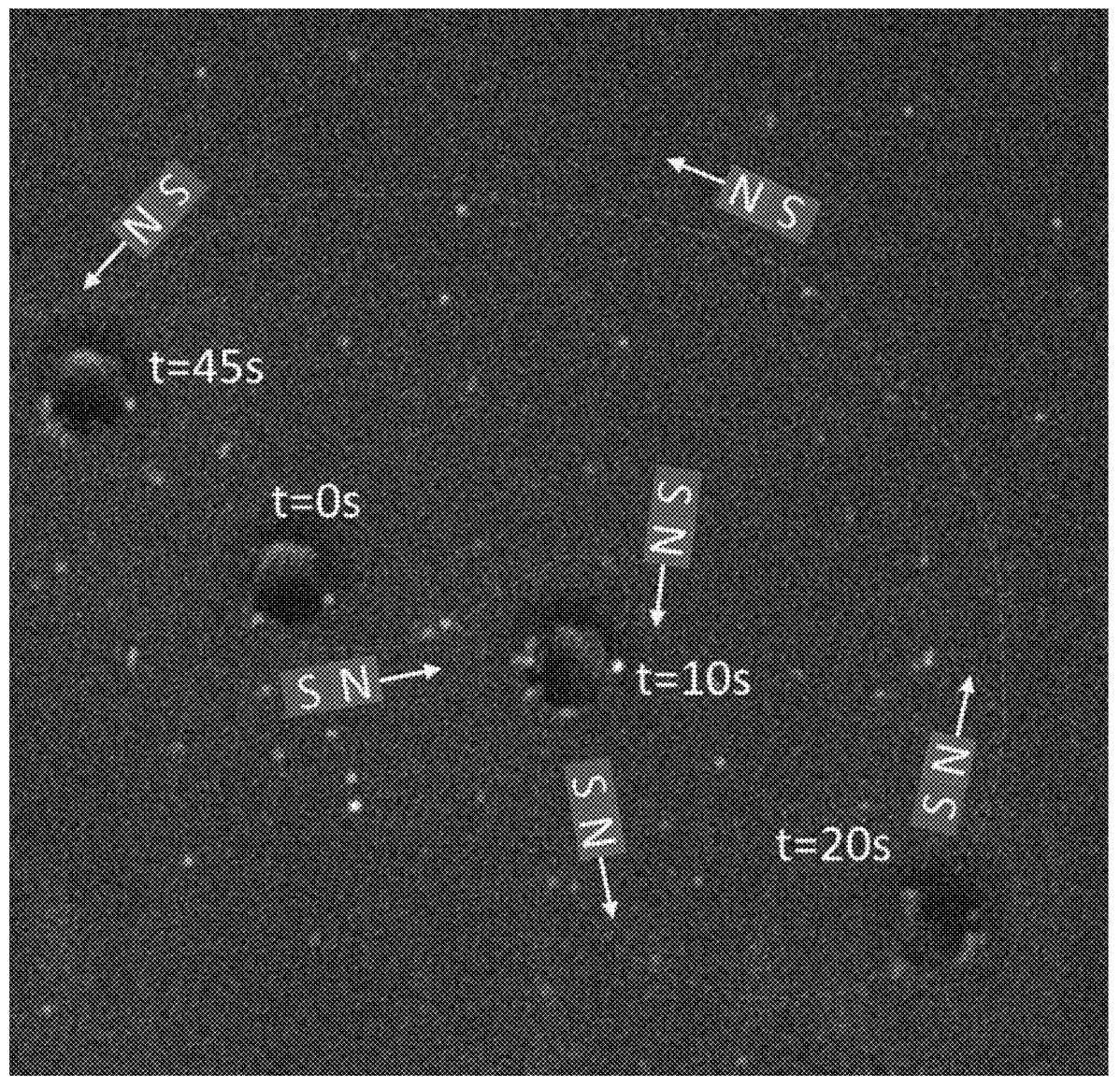
FIG. 11 shows JP (10 µm) path during the trapping process of *E. coli*, as obtained by superimposing microscope images at different times, operated under 10V and 200 kHz. Steering of the JP is achieved by rotating a permanent magnet.

As the voltage increased, the number of *E. coli* trapped between the JP and the ITO substrate and on the equator of the polystyrene side also increased (FIG. 9D), as was expected due to the increased DEP force. In the low-frequency case (50±20 k Hz), the number of trapped *E. coli* increased with time. This was due to the induced-charge electro-osmotic flow (ICEO) generated at the metallic hemisphere in the form of jetting, which brought more *E. coli* from the polystyrene side of the JP. In contrast, in the high-frequency case (5M Hz), where there was no electro-convection since the frequency was significantly higher than the RC frequency of the induced-charge, the number of *E. coli* trapped at the JP remained un-changed.

During the release stage (electric field is turned off), a large number of *E. coli* that were trapped above the JP but could not be visualized during the field operation were released. Hence, this Example concentrates on the electroporation efficiency of the *E. coli* trapped between the JP and ITO substrate as well as those trapped at the equator of the polystyrene side as these could be visualized during the entire process.

Local and Selective Electroporation Under Continuous AC Field

FIGS. 3A-C depict the micrographs of the PI-stained *E. coli* within the ITO chamber under various AC field parameters and operation times. The PI uptake for trapped *E. coli* increased with the voltage, due to the increased voltage drop across the cell membrane (i.e., transmembrane potential $\Delta\psi_{member}$), which in turn, resulted in increased electroporation, in accordance with Schwan's equation.

Figure 4B:
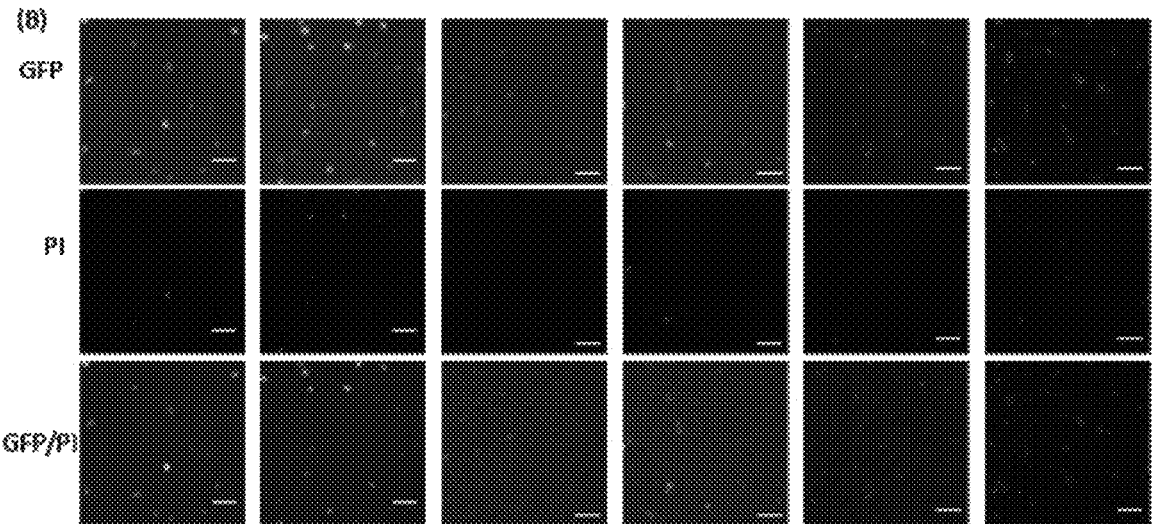
Figure 4C:
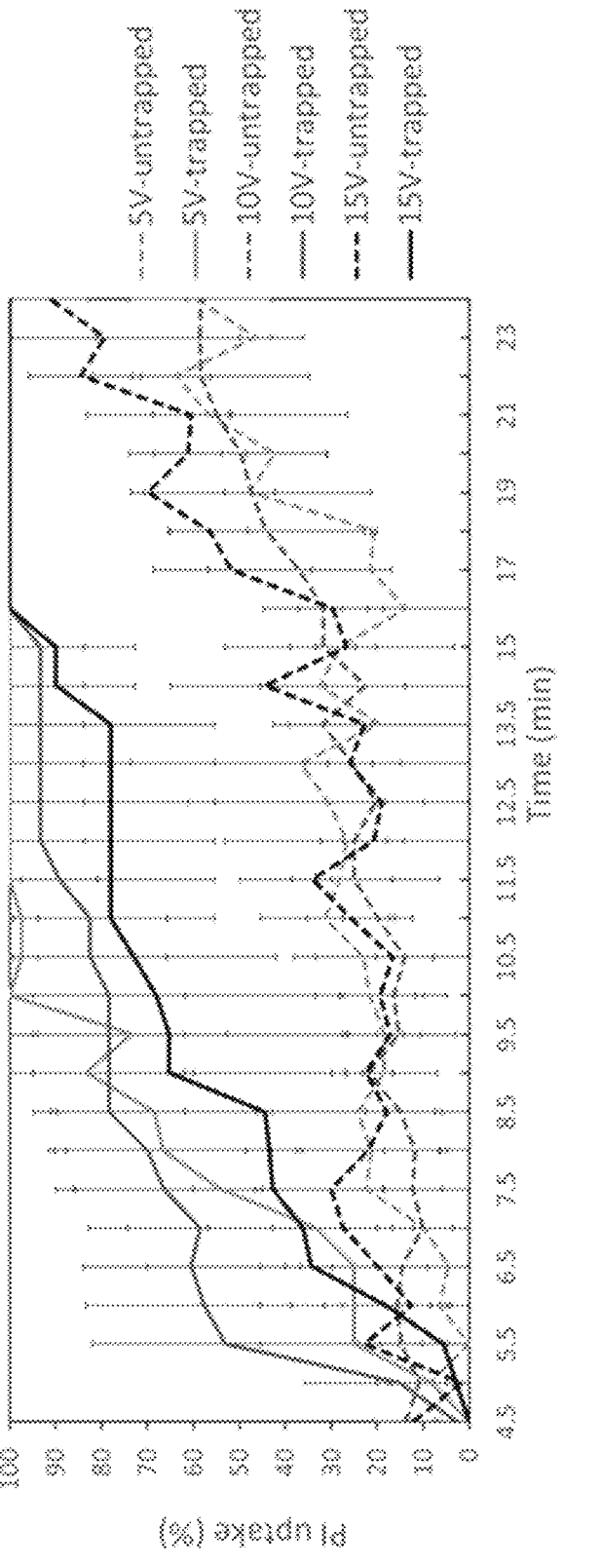

PI uptake rate was significantly higher in the trapped versus un-trapped *E. coli*. For example, under low frequency (50±20 k Hz, 10 V), 80% of the trapped *E. coli* were stained at 10 min, whereas, most of the un-trapped *E. coli* were still intact (20% PI uptake). Under high frequency (5M Hz, 10 V), 45% of the trapped *E. coli* were stained at minute 10, whereas, only ~18% of the un-trapped *E. coli* were stained. However, while at high frequency, PI uptake increased monotonically with increasing voltage, at low frequency, PI uptake at 5 V was higher than at 15 V from minutes 4-17. This unexpected result might partly stem from the fact that there were multiple layers of *E. coli* trapped at 15V (see also the transition from a single layer to multiple layers of trapped polystyrene 2 μm particles upon increase of the voltage from 5V to 15V as depicted in FIGS. 10A and 10B), where the bacteria located at the outer layers were less affected by the intensified electric fields as they were located further away from the center of the JP and because the electric fields were screened by the cells within the inner layers. In addition, the induced electroconvective flow generated by the metallic hemisphere of the JP may have continuously pumped intact *E. coli* from the bulk region from the JP dielectric side. Furthermore, the PI uptake rate of trapped *E. coli* at high frequency was lower than at low frequency. For example, at 5V, up to about 75% of the cells were stained at the high frequency (FIGS. 4A-C) and 100% at low frequency (FIGS. 4A-C). This is because the transmembrane potential decreased with increasing frequency, according to EQs. 1.2 and 1.3 (see also Table 1.1).

Viability Test of Local and Selective Electroporation Under Continuous AC Field

Figure 6A:
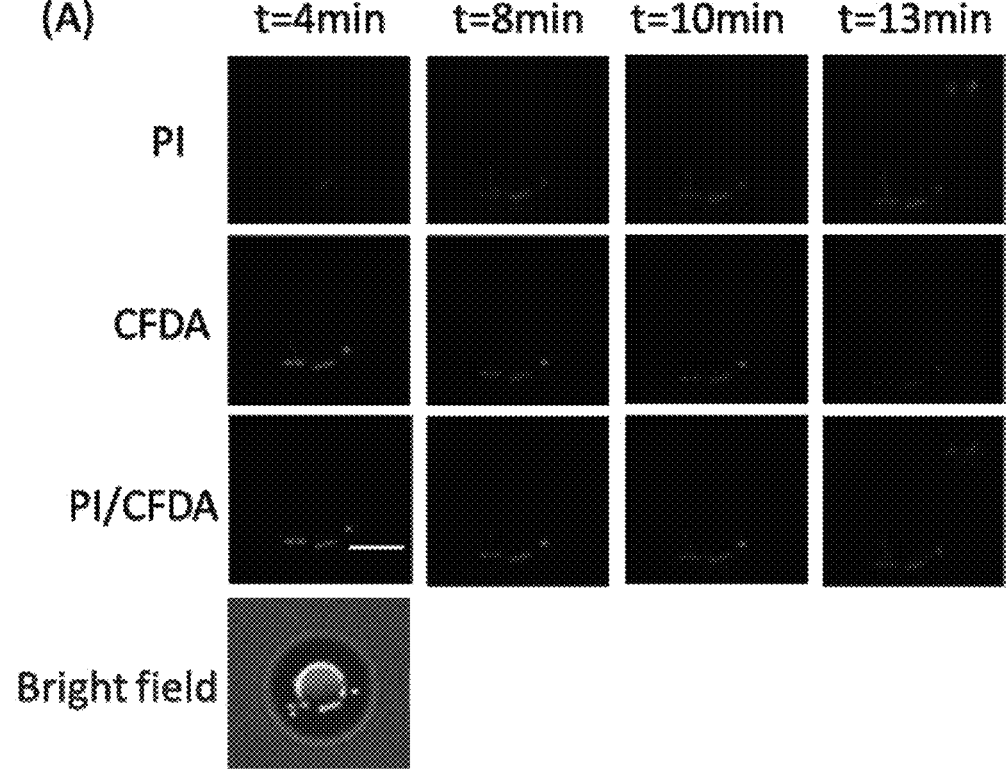
FIGS. 6A-D show microscope images of CFDA and PI-stained trapped *E. coli*, at both low (33 kHz) and high (5M Hz) frequency, 10V and various operation times. CFDA (green fluorescence) indicates cell viability and PI uptake (red fluorescence) indicates cell electroporation. (A) Low frequency (33 kHz) and (B) High frequency (5 MHz) trapped *E. coli*. (C-D) Normalized fluorescence intensity (i.e. ratio of the overall fluorescent intensity within a circle of 3 µm in diameter around each bacteria to its maximum overall fluorescent intensity value) of trapped *E. coli* in (C) CFDA channel and (D) PI channel for both low (33 kHz) and high (5 MHz) frequency. Continuous lines represent averaged values of the individual bacteria depicted as points. Janus particles of 10 µm in diameter were used. Scale bar=5 µm. *E. coli* strain XL 1-Blue bacteria without GFP labelling was used.
Figure 6B:
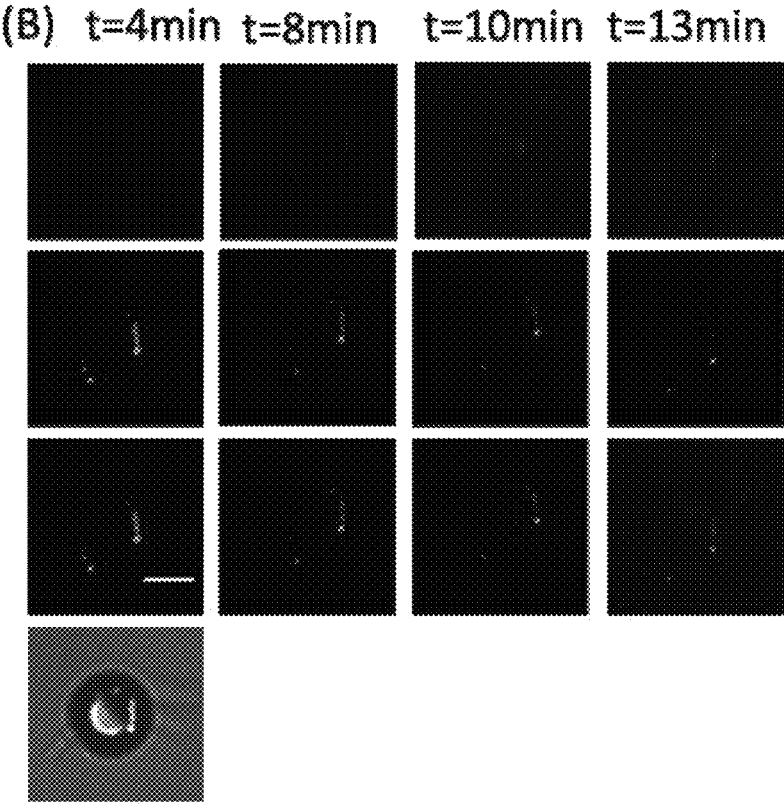
Figures 6C, 6D:
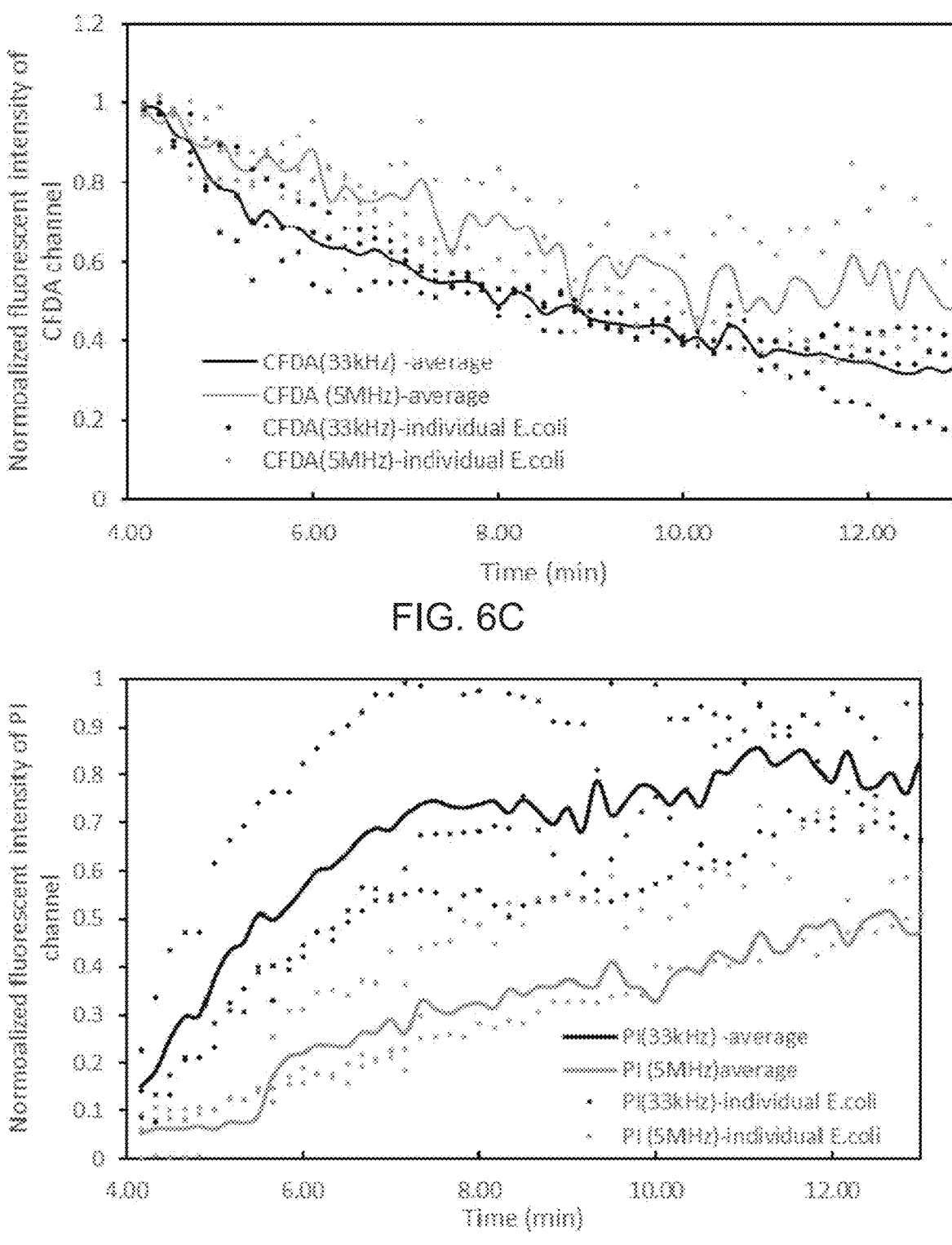
Figure 7A:
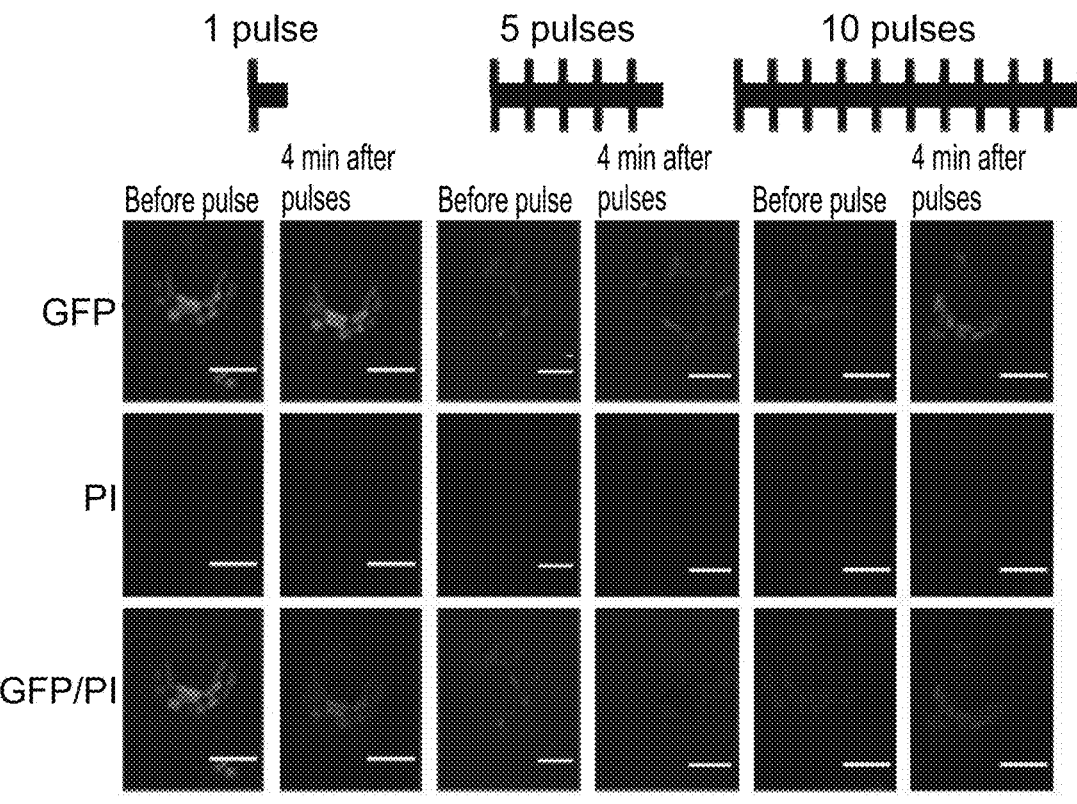
FIGS. 7A-D show microscope images of PI-stained trapped versus non-trapped *E. coli*, under an AC pulse train, various number of pulses, and operation times. PI uptake (red fluorescence) indicates cell electroporation. (A) Trapped and (B) untrapped *E. coli*. (C) Percentage of both trapped and un-trapped PI-stained *E. coli*, 4 minutes after pulses (frequency: 2M Hz, voltage: 10 V, duration: 0.5 ms) Insert: Percentage of PI-stained cells over time, following a train of 10 pulses. (D) Variation of AC voltage and frequency across the experiment chamber and over time. Janus particle of 10 µm in diameter was used. *E. coli* strain XL 1-Blue bacteria with GFP labelling was used. Scale bar=5 µm.
Figure 7B:
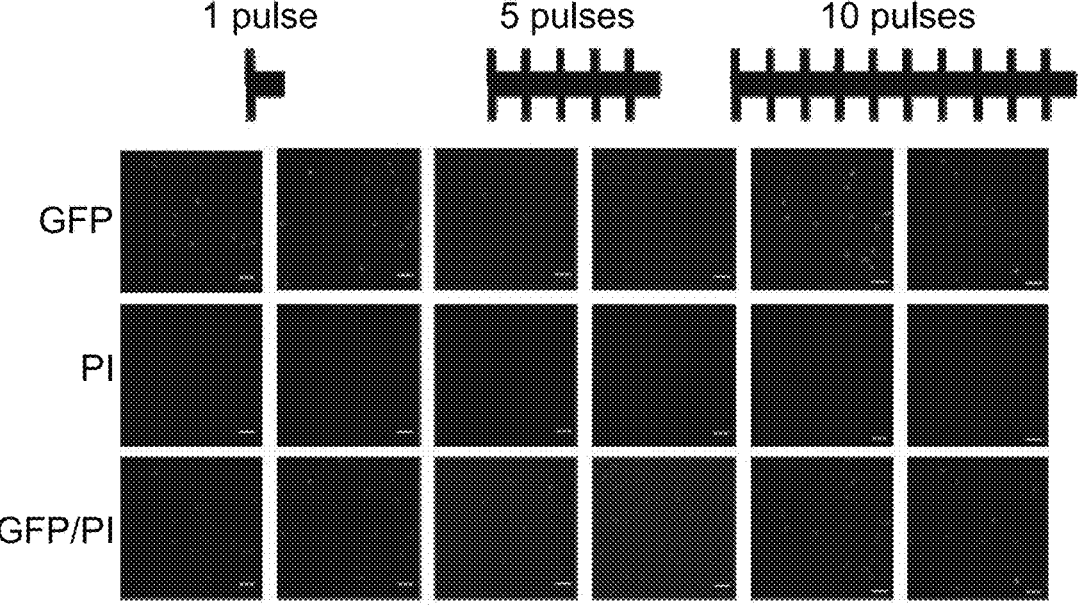
Figure 7C:
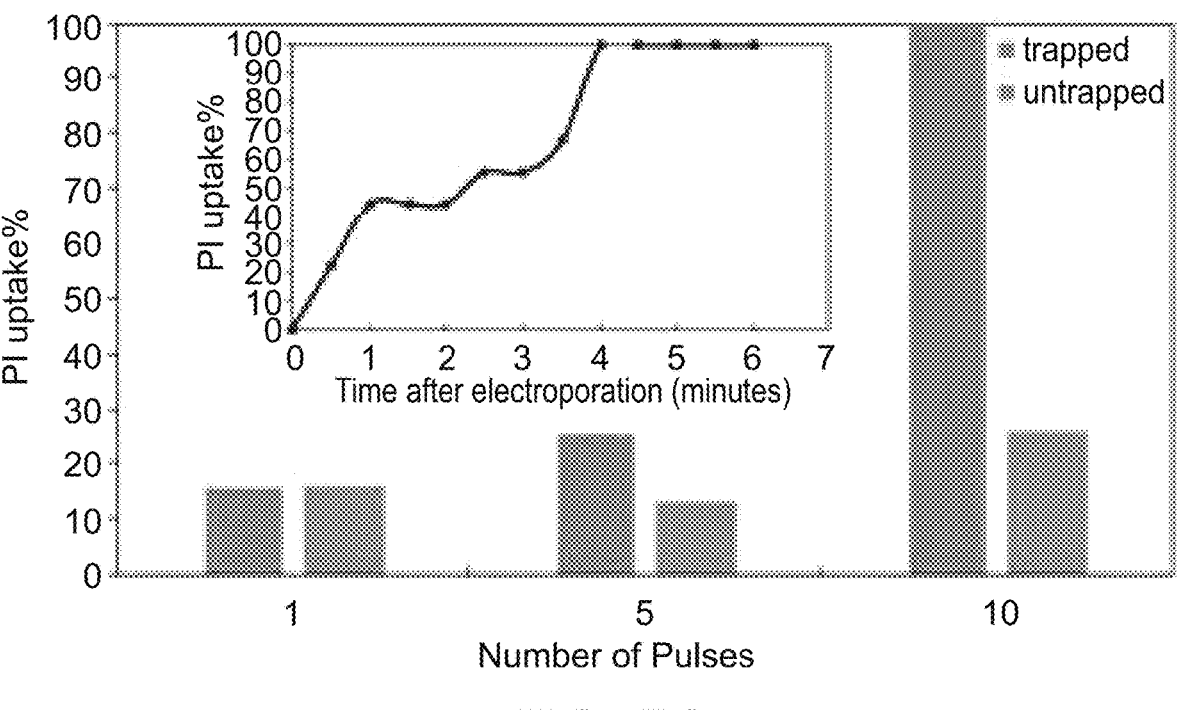
Figure 7D:
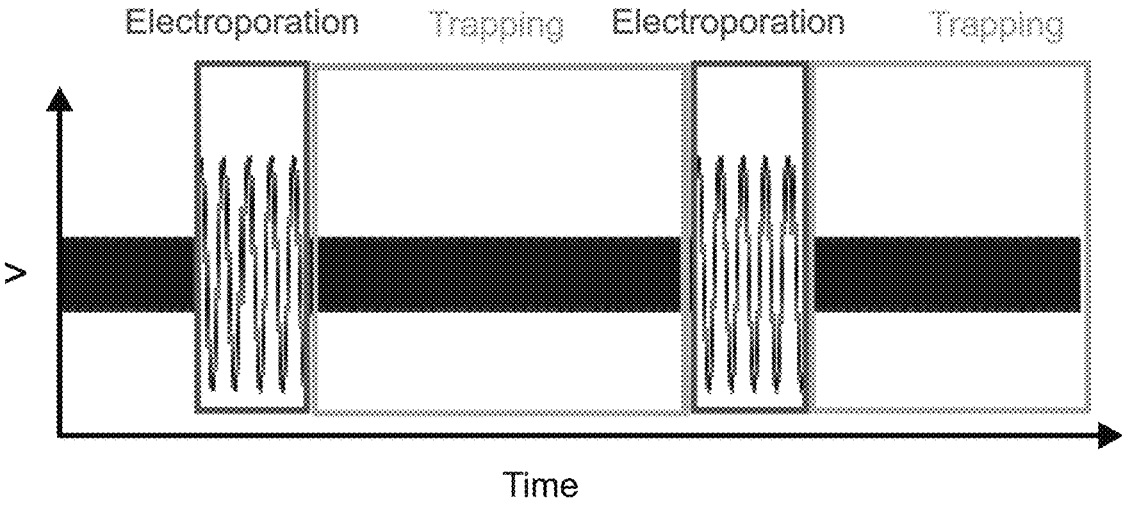

CFDA and PI-stained *E. coli* were used to demonstrate that the micromotor of the present embodiments allows both reversible (i.e. cell viability is retained) and irreversible electroporation (i.e. electrical lysis of cells) electroporation. While PI is an indication of electroporation, CFDA is an indication of cell viability. As shown in FIGS. 6A-B, while the fluorescent intensity of PI increases, the fluorescent intensity of CFDA decreases for both low and high frequency electroporation, indicating that cell viability is decreasing during the electroporation process. PI increased faster in low frequency (33 kHz) electroporation than in high frequency (5 MHz), while CFDA decreased similarly at both frequencies. This result further confirms that electroporation efficiency is strongly dependent on the frequency and is more efficient at the lower frequency. In contrast, cell death seems to be less dependent on the frequency. As shown in FIG. 6C, a successful reversible electroporation of PI was achieved (>50% intake efficiency) without inducing significant *E. coli* damage as revealed by about 80% CFDA retention when the electroporation is conducted at 33 kHz and 10V for less than one minute.

Local and Selective Electroporation Under AC Pulses

In order to suppress continuous electroporation while holding the bacteria, it is preferred to use high frequency, which maintains a lower transmembrane potential (e.g., 5M Hz instead of 50±20 k Hz). In this manner, on-demand electroporation can be achieved by combining short pulses with a continuous AC signal. Moreover, the electroconvection flow which occurs under the low frequency regime and may adversely influence the cell status (e.g., bringing new bacteria, shearing trapped bacteria etc.), is completely suppressed. When applying an AC pulse train, the JP remained on the substrate in contrast to the case of DC pulse, which seemed to levitate the JP and in this manner, lose the trapped cells. In addition, AC signals tend to reduce electrolysis relative to DC signals. As shown in FIGS. 6A-D, application of a train of 10 AC pulses yielded a significantly higher percentage of PI-stained cells (100% b) compared with a train of 5 (25%) or 1 AC pulse (15%) applied over the same incubation time (4 min). Moreover, after 10 pulses and 4 minutes of incubation, most of the untrapped *E. coli* were still intact (<25% PI uptake). In this Example, no attempt was made to optimize the parameters (e.g., duration, peak intensity, interval between pulses etc.) of the pulses and still obtained a clear differentiation in the electroporation response between the conditions at the JP versus the untrapped *E. Coli*. Such parameters can be tuned according to some embodiments of the present invention when reversible or non-reversible electroporation conditions are required.

Discussion

An electrokinetically driven JP can function as a mobile microelectrode, capable of manipulating cargo via DEP, and serve as a platform for electroporation of cells, due to locally intensified electrical field. This Example successfully unified the selective transport, loading and electroporation of biological cargo by simply changing the frequency and amplitude of the applied electric field.

Regarding the trapping capacity of the JP, it was shown that at a frequency of 300 k Hz, the number of trapped *E. coli* increased with increasing voltage. The *E. coli* trapped at low frequency versus high frequency showed distinct orientations resulting from the different electric field streamlines obtained under the different frequency regime. This observation was due to the non-spherical (rod) shape of the bacteria. At frequencies much lower than the relaxation frequency of the induced electric double layer (EDL), the metallic hemisphere is electrically screened and the electric field lines outside the EDL are mostly tangential to the JP surface, resembling the electrostatic solution around an insulator. At very high frequencies, wherein there isn't sufficient time for the charging of the induced EDL, the metallic hemisphere is not screened and the electric field lines are perpendicular to it, resembling the electrostatic solution around a conductor.

The JP is capable of selectively electroporate the trapped cells due to the local electric field intensification, induced by the JP itself, at two locations: 1) under the metallic surface and 2) at the equator of the polystyrene surface. Electroporated cells were stained with PI and their percentage increased with increasing voltages, at all frequencies. For the same applied voltage, the PI uptake rate was higher at the lower frequency (50±20 k Hz), in agreement with the Schwan's equation for the transmembrane potential. It was found that at the end of the trapping stage (2 minutes), less than 10% of the trapped cells were electroporated, which allowed the collection and transport of intact *E. coli* to a secondary location, where they were then electroporated and further analyzed.

Figures 12A, 12B:
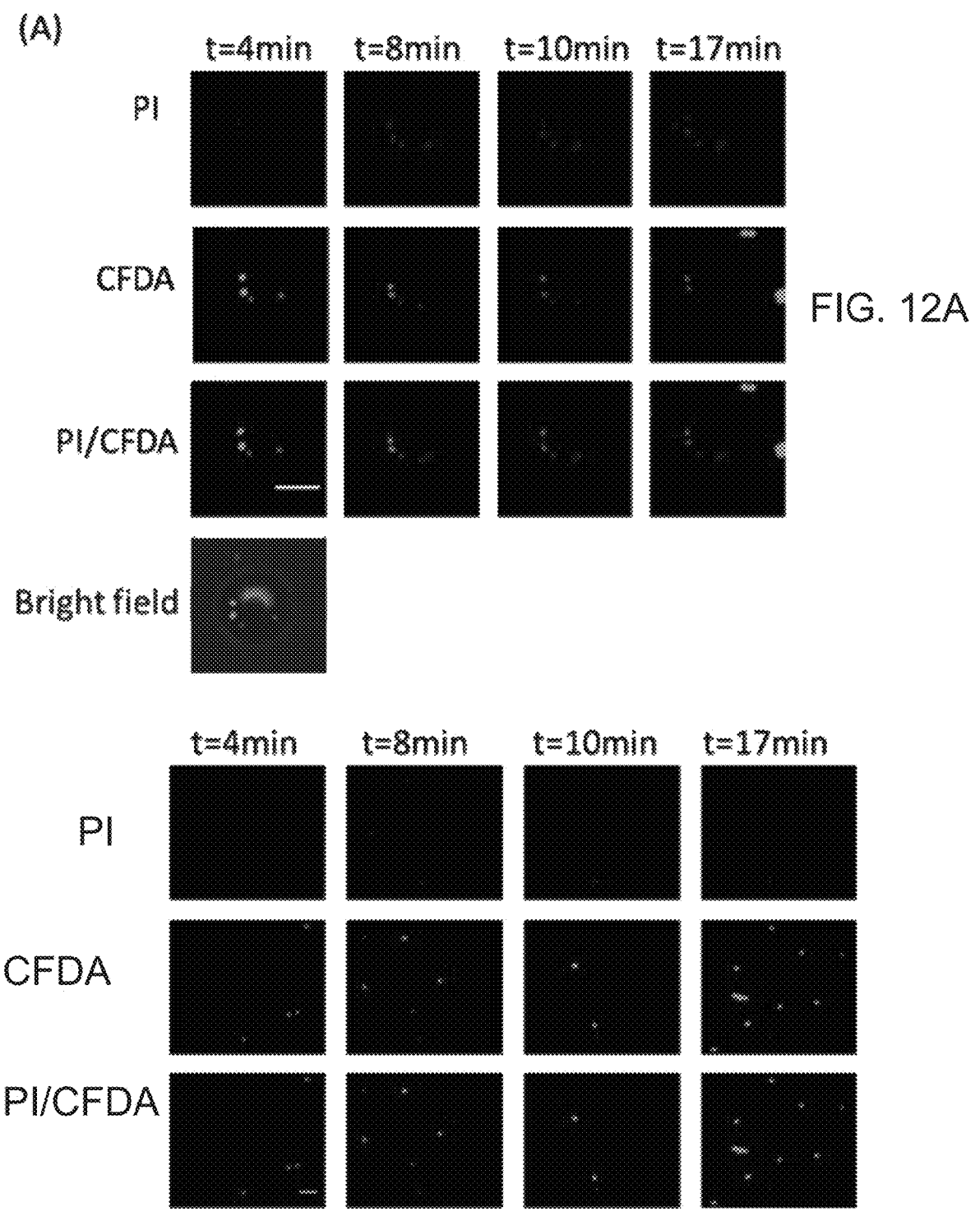
FIGS. 12A-D show microscope images of PI and CFDA-stained trapped versus non-trapped *Rhodococcus*, at low frequency of 33 Hz, 10V, and various operation times. PI (red fluorescence) indicates cell electroporation and CFDA (green fluorescence) indicates cell viability. Microscopic images of (A) trapped *Rhodococcus* and (B) untrapped *Rhodococcus*. Normalized fluorescent intensity (i.e. ratio of the overall fluorescent intensity within a circle of 3 µm in diameter around each bacteria to the maximum overall fluorescent intensity value obtained for the trapped bacteria) in CFDA channel (C) and PI channel (D) of both trapped and untrapped *Rhodococcus* versus time. Continuous lines represent averaged values of the individual bacteria depicted as points. Janus particle of 10 µm in diameter was used. Scale bar=5 µm.
Figure 12C:
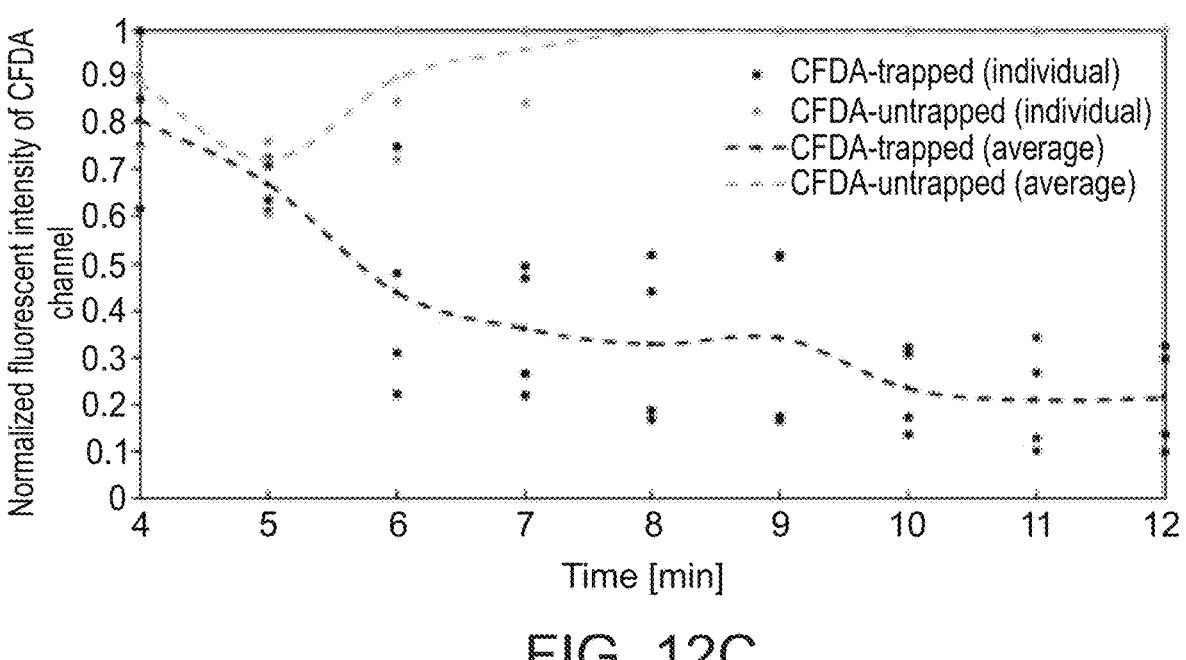
Figure 12D:
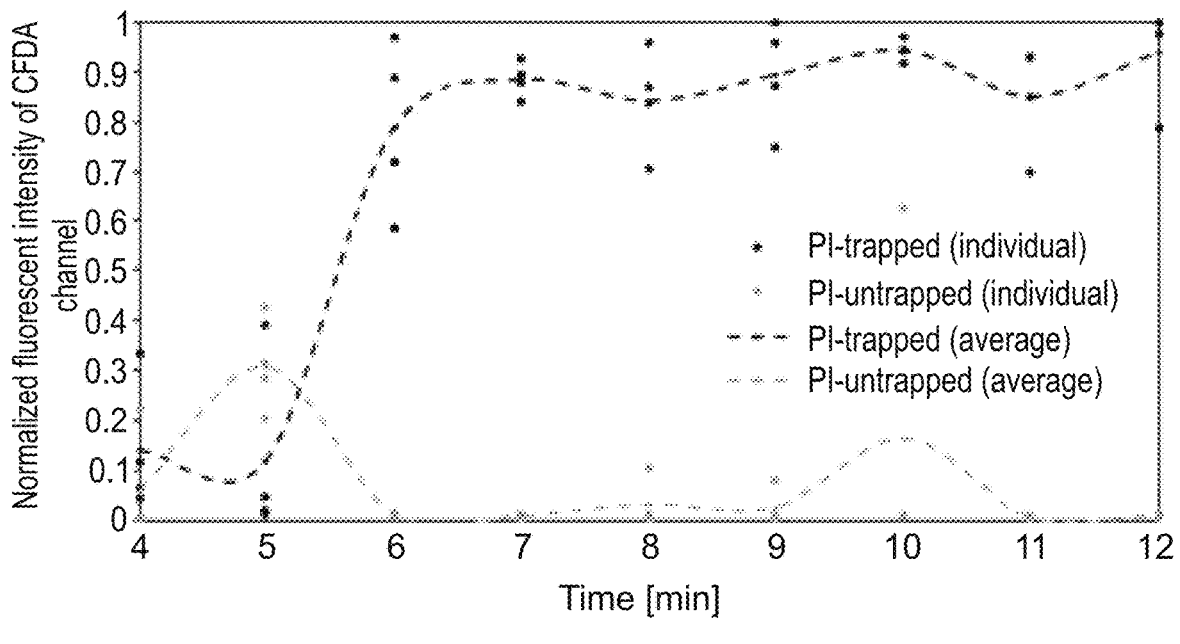

Since both DEP and electroporation apply to any type of cell (regardless of its size, shape and surface properties) and are not restricted to a specific design of electrodes (e.g., mobile microelectrodes, such as, but not limited to, JP, or fixed electrodes, such as, but not limited to, in a chip designs), the mechanisms demonstrated herein can be used for any electrode and any electroporatable particle. Specifically, although the DEP response the Clausius-Mossotti factor) of different cell types maybe different, it can be controlled by tuning the frequency to achieve the desired behavior (e.g., positive DEP as in the current study). The same applies for the electroporation where by tuning the continuous AC field or train of pulses parameters (e.g., number, intensity, duration) one can achieve desired electroporation conditions for different cell types. To further demonstrate its applicability to other types of bacteria an experiment was performed with *Rhodococcus erythropolis* ATCC 4277 of spherical shape (unlike the rod shape of *E. coli*). As shown in FIGS. 12C-D, successful trapping and reversible electroporation of PI was achieved (>80% intake efficiency) for the trapped *Rhodococcus* without inducing significant cell damage as revealed by about 50% CFDA retention when the electroporation is conducted at 33 kHz and 10V for less than two minutes. The untrapped cells showed no significant PI uptake.

Taken together, the JP can be applied to pre-concentrate and electroporate trace amounts of bacteria in samples, which can then be analyzed in a short time period. This application is useful in water safety monitoring, health surveillance, and clinical diagnosis, where detection and identification of trace amounts of viable bacterial pathogens is in high demand. It is expected that the described biological cargo carrier and targeted electroporation can be used in applications integrating single-cell analysis methods, such as PCR, gene sequencing, fluorescence in situ-hybridization and immunofluorescence staining, where the carrier selectively picks up a target and transport it to a secondary chamber to be lysed for further analysis of its genomics, transcriptomics, proteomics, and/or metabolomics. The selective trapping and single-cell lysis system also allows investigation of cell heterogeneity.

Since an AC pulse train can electroporate cells, while keeping them trapped, the present embodiments can be used for introducing large molecules and plasmid DNA into a bacteria. This can be useful in gene cloning and research of molecular biology. The JP can accurately trap the desired number of DNA plasmids to be transfected into the target cell.

Since the active particle achieved its highest velocity and pDEP force in medium with low conductivities (<0.09 S/m), in some embodiments of the present invention solution of low ionic conductivity but of osmolality that is similar to a physiological solution is used. This is particularly useful when the particles are mammalian cells. Also contemplated is the use of physiological medium by combining a non-electrokinetic propulsion mechanism, in combination with electrical-based DEP for manipulation (load, release) of the biological cargo and electroporation.

Similarly to nanochannel electroporation the mobile microelectrode of the present embodiments is able to perform electroporation on a smaller portion of the cell and hence is expected to result in significantly higher reversible electroporation yield as the locally electroporated cells can be more easily recovered relative to standard electroporation. The latter is not only not selective, wherein many of the bacteria in the chamber are uniformly electroporated, but also result in the entire cell membrane being electroporated due to the uniform electric field conditions on the cell membrane. Moreover, due to the ability to preconcentrate not only the targeted cells but also large molecules (e.g., plasmids) to be electroporated onto the same JP—then the electroporation yield for the targeted cells (e.g., bacteria) is increased. In bacteria there is also a cell wall in addition to cell membrane, where both are affected by the electric field. However, while small molecules (e.g., PI), introduced into the cell through the electroporated cell membrane, are not affected by the cell wall, large molecules (e.g., plasmids) can be trapped within the cell wall.

REFERENCES FOR EXAMPLE 1

1. W. Gao et al., Artificial Micromotors in the Mouse's Stomach: A Step toward in Vivo Use of Synthetic Motors. ACS Nano. 9, 117-123 (2015).
2. J. Orozco et al., Micromotor-Based High-Yielding Fast Oxidative Detoxification of Chemical Threats. Angew. Chemie Int. Ed. 52, 13276-13279 (2013).
3. W. Gao et al., Seawater-driven magnesium based Janus micromotors for environmental remediation. Nanoscale. 5, 4696 (2013).
4. J. Li et al., Self-Propelled Nanomotors Autonomously Seek and Repair Cracks. Nano Lett. 15, 7077-7085 (2015).
5. K. Han, C. W. Shields, O. D. Velev, Engineering of Self-Propelling Microbots and Microdevices Powered by Magnetic and Electric Fields. Adv. Funct. Mater. 28, 1705953 (2018).
6. S. Gangwal, O. J. Cayre, M. Z. Bazant, O. D. Velev, Induced-Charge Electrophoresis of Metallodielectric Particles. Phys. Rev. Lett. 100, 058302 (2008).
7. Z. Wu et al., A swarm of slippery micropropellers penetrates the vitreous body of the eye. Sci. Adv. 4, eaat4388 (2018).
8. Y. Wu, T. Si, J. Shao, Z. Wu, Q. He, Near-infrared light-driven Janus capsule motors: Fabrication, propulsion, and simulation. Nano Res. 9, 3747-3756 (2016).
9. T. Xu, W. Gao, L.-P. Xu, X. Zhang, S. Wang, Fuel-Free Synthetic Micro/Nanomachines. Adv. Mater. 29, 1603250 (2017).
10. T. Mirkovic, N. S. Zacharia, G. D. Scholes, G. A. Ozin, Nanolocomotion-Catalytic Nanomotors and Nanorotors. Small. 6, 159-167 (2010).
11. B. P. Nadappuram et al., Nanoscale tweezers for single-cell biopsies. Nat. Nanotechnol. 14, 80-88 (2019).
12. S. Sundararajan, P. E. Lammert, A. W. Zudans, V. H. Crespi, A. Sen, Catalytic Motors for Transport of Colloidal Cargo. Nano Lett. 8, 1271-1276 (2008).
13. J. Orozco et al., Dynamic Isolation and Unloading of Target Proteins by Aptamer-Modified Microtransporters. Anal. Chem. 83, 7962-7969 (2011).
14. A. M. Boymelgreen, T. Balli, T. Miloh, G. Yossifon, Active colloids as mobile microelectrodes for unified label-free selective cargo transport. Nat. Commun. 9, 760 (2018).
15. R. Pethig, Review—Where Is Dielectrophoresis (DEP) Going? J. Electrochem. Soc. 164, B3049-B3055 (2017).
16. A. M. Boymelgreen, T. Balli, T. Miloh, G. Yossifon, Active colloids as mobile microelectrodes for unified label-free selective cargo transport. Nat. Commun. 9 (2018), doi:10.1038/s41467-018-03086-2.
17. A. Boymelgreen, G. Yossifon, T. Miloh, Propulsion of Active Colloids by Self-Induced Field Gradients. Langmuir. 32, 9540-9547 (2016).
18. N. L. Abbott, O. D. Velev, Active particles propelled into researchers' focus. Curr. Opin. Colloid Interface Sci. 21, 1-3 (2016).
19. S. J. Ebbens, Active colloids: Progress and challenges towards realising autonomous applications. Curr. Opin. Colloid Interface Sci. 21, 14-23 (2016).
20. J. Yan et al., Reconfiguring active particles by electrostatic imbalance. Nat. Mater. 15, 1095-1099(2016).
21. T. M. Squires, M. Z. Bazant, Breaking symmetries in induced-charge electro-osmosis and electrophoresis. J. Fluid Mech. 560, 65 (2006).
22. A. F. Demirörs, M. T. Akan, E. Poloni, A. R. Studart, Active cargo transport with Janus colloidal shuttles using electric and magnetic fields. Soft Matter. 14, 4741-4749 (2018).
23. R. B. Brown, J. Audet, Current techniques for single-cell lysis. J. R. Soc. Interface. 5 (2008), doi:10.1098/rsif.2008.0009.focus.

24. M. Hilgle et al., A lab-on-a-chip for preconcentration of bacteria and nucleic acid extraction. RSC Adv. 8, 20124-20130 (2018).

25. P. Vulto et al., A microfluidic approach for high efficiency extraction of low molecular weight RNA. Lab Chip. 10, 610-6 (2010).

26. J. Olofsson et al., Single-cell electroporation. Curr. Opin. Biotechnol. 14, 29-34 (2003).

27. C. Xie, Z. Lin, L. Hanson, Y. Cui, B. Cui, Intracellular recording of action potentials by nanopillar electroporation. Nat. Nanotechnol. 7, 185-190 (2012).

28. H. Lu, M. A. Schmidt, K. F. Jensen, A microfluidic electroporation device for cell lysis. Lab Chip. 5, 23 (2005).

29. L. Chang et al., Magnetic tweezers-based 3D microchannel electroporation for high-throughput gene transfection in living cells. Small. 11, 1818-1828 (2015).

30. L. Chang et al., Dielectrophoresis-assisted 3D nanoelectroporation for non-viral cell transfection in adoptive immunotherapy. Lab Chip. 15, 3147-3153 (2015).

31. J. A. Lundqvist et al., Altering the biochemical state of individual cultured cells and organelles with ultramicroelectrodes. Proc. Natl. Acad. Sci. U.S.A 95, 10356-60 (1998).

32. E. N. T6th et al., Single-cell nanobiopsy reveals compartmentalization of mRNAs within neuronal cells. J. Biol. Chem. 293, 4940-4951 (2018).

33. S. Homhuan, B. Zhang, F.-S. Sheu, A. A. Bettiol, F. Watt, Single-cell electroporation using proton beam fabricated biochips. Biomed. Microdevices. 14, 533-540 (2012).

34. H. Sedgwick, F. Caron, P. B. Monaghan, W. Kolch, J. M. Cooper, Lab-on-a-chip technologies for proteomic analysis from isolated cells. J. R. Soc. Interface. 5 Suppl 2, S123-30 (2008).

35. C. Lyu, J. Wang, M. Powell-Palm, B. Rubinsky, Simultaneous electroporation and dielectrophoresis in non-electrolytic micro/nano-electroporation. Sci. Rep. 8, 2481 (2018).

36. A. Boymelgreen, G. Yossifon, Observing Electrokinetic Janus Particle-Channel Wall Interaction Using Microparticle Image Velocimetry. Langmuir. 31, 8243-8250 (2015).

37. D. Ben-Bassat, A. Boymelgreen, G. Yossifon, The influence of flow intensity and field frequency on continuous-flow dielectrophoretic trapping. J. Colloid Interface Sci. 442, 154-161 (2015).

38. A. Boymelgreen, G. Yossifon, T. Miloh, Propulsion of Active Colloids by Self-Induced Field Gradients. Langmuir. 32, 9540-9547 (2016).

39. T. Batista Napotnik, D. Miklavčič, In vitro electroporation detection methods—An overview. Bioelectrochemistry. 120, 166-182 (2018).

40. A. Boymelgreen, G. Yossifon, Observing Electrokinetic Janus Particle-Channel Wall Interaction Using Microparticle Image Velocimetry. Langmuir. 31, 8243-8250 (2015).

41. E. Neumann, A. E. Sowers, C. A. Jordan, Eds., Electroporation and Electrofusion in Cell Biology (Springer US, Boston, MA, 1989;

42. P. Marszalek, D. S. Liu, T. Y. Tsong, Schwan equation and transmembrane potential induced by alternating electric field. Biophys. J. 58, 1053-8 (1990).

43. A. Baumstummler et al., Development of a nondestructive fluorescence-based enzymatic staining of microcolonies for enumerating bacterial contamination in filterable products, 69-79 (2010).

44. Y. Zhan et al., Low-frequency ac electroporation shows strong frequency dependence and yields comparable transfection results to dc electroporation. J. Control. Release. 160, 570-576 (2012).

45. L. Wu et al., Trace Detection of Specific Viable Bacteria Using Tetracysteine-Tagged Bacteriophages. Anal. Chem. 86, 907-912 (2014).

46. F. Lan, B. Demaree, N. Ahmed, A. R. Abate, Single-cell genome sequencing at ultra-high-throughput with microfluidic droplet barcoding. Nat. Biotechnol. 35, 640-646 (2017).

47. R. J. Kimmerling et al., A microfluidic platform enabling single-cell RNA-seq of multigenerational lineages. Nat. Commun. 7, 10220 (2016).

48. R. D. Pedde, H. Li, C. H. Borchers, M. Akbari, Microfluidic-Mass Spectrometry Interfaces for Translational Proteomics. Trends Biotechnol. 35, 954-970 (2017).

49. L. J. Barkal et al., Microbial metabolomics in open microscale platforms. Nat. Commun. 7, 10610 (2016).

50. W. Jing, B. Camellato, I. J. Roney, M. Kaem, M. Godin, Measuring Single-Cell Phenotypic Growth Heterogeneity Using a Microfluidic Cell Volume Sensor. Sci. Rep. 8, 17809 (2018).

51. M. Kanduser, D. Miklavčič, in Electroporation in Biological Cell and Tissue: An Overview (Springer, New York, NY, 2009;

52. J. S. Wiegert, C. E. Gee, T. G. Oertner, Single-Cell Electroporation of Neurons. Cold Spring Harb. Protoc. 2017, 135-138 (2017).

53. P. Ruzgys, M. Jakutavičiūtė, I. Šatkauskienė, K. Čepurnienė, S. Šatkauskas, Effect of electroporation medium conductivity on exogenous molecule transfer to cells in vitro. Sci. Rep. 9, 1436 (2019).

54. Y.-L. Chen, C.-X. Yang, H.-R. Jiang, Electrically Enhanced Self-Thermophoresis of Laser-Heated Janus Particles under a Rotating Electric Field. Sci. Rep. 8, 5945 (2018).

55. K. Gao et al., Design of a Microchannel-Nanochannel-Microchannel Array Based Nanoelectroporation System for Precise Gene Transfection. Small. 10, 1015-1023 (2014).

56. D. C. Chang, T. S. Reese, Changes in membrane structure induced by electroporation as revealed by rapid-freezing electron microscopy. Biophys. J. 58, 1-12 (1990).

57. J. F. Miller, W. J. Dower, L. S. Tompkins, High-voltage electroporation of bacteria: genetic transformation of *Campylobacter jejuni* with plasmid DNA. Proc. Natl. Acad. Sci. U.S.A 85, 856-60 (1988).

58. H. Kimoto, A. Taketo, Initial Stage of DNA-Electrotransfer into *E. coli* Cells. J. Biochem. 122, 237-242 (1997).

59. C.-Y. Wu, K. T. Roybal, E. M. Puchner, J. Onuffer, W. A. Lim, Remote control of therapeutic T cells through a small molecule-gated chimeric receptor. Science (80-.). 350, aab4077-aab4077 (2015).

60. S. V. Puttaswamy et al., Enhanced cell viability and cell adhesion using low conductivity medium for negative dielectrophoretic cell patterning. Biotechnol. J. 5, 1005-1015 (2010).

Example 2

Micromotor-Based Biosensing

This Example demonstrates the use of the same micromotor system for sensing of varying targets via different functionalized beads, demonstrating the use of micromotors as a practical and versatile means for biosensing. This Example also describes a simplified microfluidic design that can be used for immunosensing or DNA binding tests without necessity for complicated fluid handling steps, such as buffer exchange, washing etc.

Active particles, that convert energy at the particle level from the surrounding environment (e.g. chemical fuel, light, ultrasound, magnetic and electric field) into autonomous self-propulsion, allows efficient coverage of large areas and volumes while operating under uniform ambient conditions without the need to generate field gradients for driving the particles.

By using different materials and surface coating techniques (e.g. molecularly imprinted polymers, biodegradable and biocompatible polymers, biomimetic material, etc.) the active particles coated with biodegradable materials or functionalized with bioreceptors have been used for various tasks such as antibacterial activity, protein detection, and intracellular biosensing of a target miRNA expressed in intact cancer cells. Known in the art is a micromotor-based immunoassay employing self-propelled antibody-functionalized micromotors where the different immunoassay steps are obtained via the mobile particle translating between different reservoirs connected using microfluidic channels [Garcia et al., Nanoscale 2013, 5 (4), 1325-1331]. This concept eliminates the need to manipulate fluids as common to lab-on-a-chip devices, thus, the washing step is obtained by the motion of the particle itself within stagnant fluid. However, the coating of the active particle with antibodies makes these micromotor specific and less generic in application.

This Example demonstrates a generic approach using a non-labeled micromotor that can selectively load, transport and release functionalized beads that are treated as cargo, singularly controlled by an external alternating electric field. In this Example, spherical metallodielectric Janus particle (JPs) are used as the micromotor, where under applied electric field, the imbalanced polarization at metallic and dielectric hemispheres results in self-propulsive behavior referred to induced-charge electrophoresis (ICEP) and self-dielectrophoresis (sDEP). Both speed and direction of the JP are controlled by the applied electric field frequency with the JP propelling either with its dielectric (ICEP) or metallic (sDEP) hemisphere forward.

The underlying mechanism of the cargo manipulation used in current work is dielectrophoresis (DEP) which enables label-free loading and release of a broad range of organic and inorganic cargos. Under a uniform external electric field, the field gradients, necessary for DEP force, are induced at the JP level. By varying the electric field frequency, a cargo particle can shift between attraction (positive DEP, pDEP) and repulsion (negative DEP, nDEP) at regions of high electric field intensity according to its geometry and material properties. Thus, combining electrically powered micromotor and DEP-based cargo manipulation allows using a uniform electric field to singularly control the selective loading, transport and release of the functionalized beads in a simple and robust manner. Adding magnetic steering, using a ferromagnetic-coating of the JPs with an externally rotating static magnet, also allows precisely navigating the micromotor.

Figures 13A, 13B:
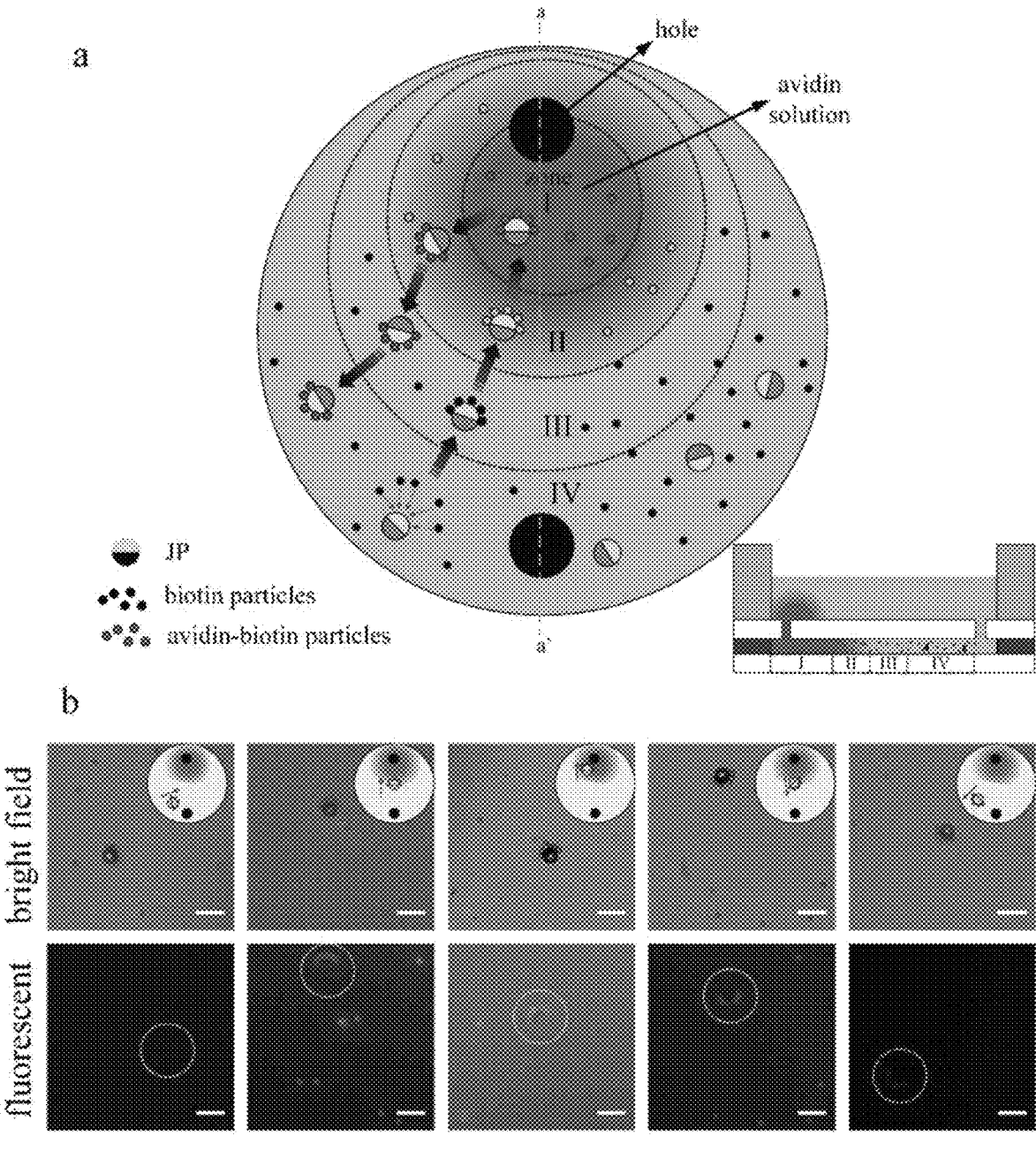
FIGS. 13A and 13B show transport of biotin-functionalized cargos using a micromotor for sensing of avidin within a single chamber system. (a) Schematics of the biosensing procedure including: i) micromotor loading several cargos while transporting them from zone IV to zone I for binding with avidin, ii) incubation time of 5 min, iii) transport of cargo to avidin-free region (zone I to IV) for washing nonspecifically bound molecules and detection of avidin-biotin binding. The inset depicts the cross-sectional side view of the system along the orange dashed line a-a'. (b) time-lapse microscope bright field (top row) and fluorescent (2nd row) images showing the micromotor based transport of cargos across the different zones. The applied electric field is 500 kHz and 10 $V_{pp}$ with sDEP and nDEP cargo trapping mode. The inset schematics in bright field images indicate the approximate location of transport of the micromotor with cargos within the entire chamber while the yellow dotted circles indicate the location of the active carrier with cargos in the fluorescent field images. The bright and fluorescent field images were taken at similar times but with a small time difference of 1-3 seconds between them. White scale bar: 15 μm.
Figure 14A:
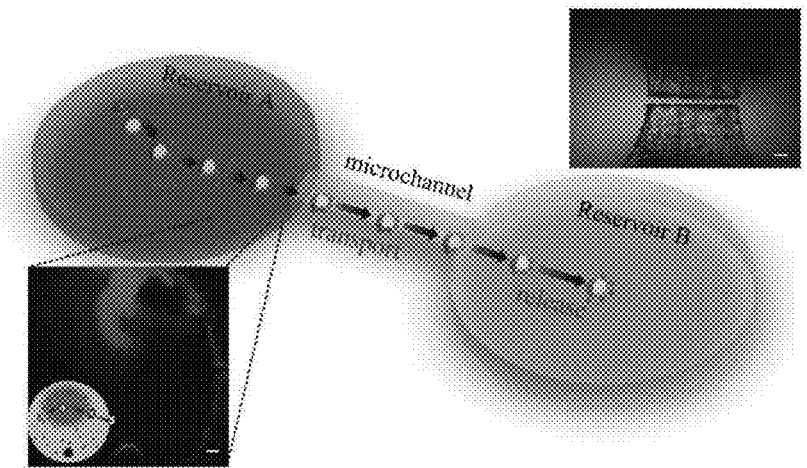
FIGS. 14A-E show transport of biotin-functionalized beads using a micromotor in a two chamber microfluidic system. (A) Schematics and a microscope image of the microfluidic system (top right inset). In reservoir A, similarly to the format in FIGS. 13A-B, the avidin molecules (200 μg mL$^{-1}$) are introduced into one of the inlet holes for binding biotin-functionalized particles for 20 min of incubation time. (B) Following incubation a micromotor in reservoir A picks up avidin-bound biotin-particles and transport them towards reservoir B. (C) Crossing the connecting microchannel (3.5 mm long) between the two reservoirs. The time interval between two superimposed images in b and c is 1 sec. The block arrow indicates the direction of motion. (D-E) Bright field and fluorescent images of transported cargos at reservoir B. Scale bars: 500 (FIGS. 14A-B), 100 (FIG. 14C) and 10 m ((FIG. 14D).
Figure 14B:
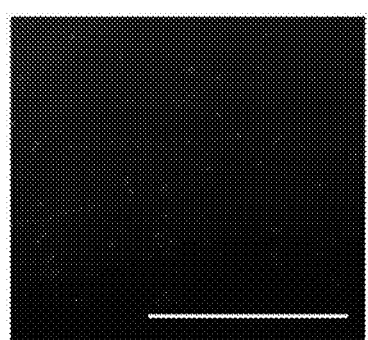
Figure 14C:
Figures 14D, 14E:
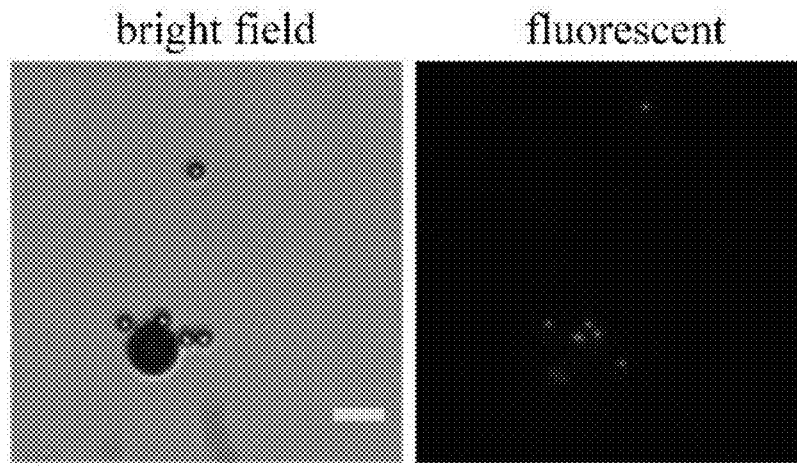
Figures 15A, 15B:
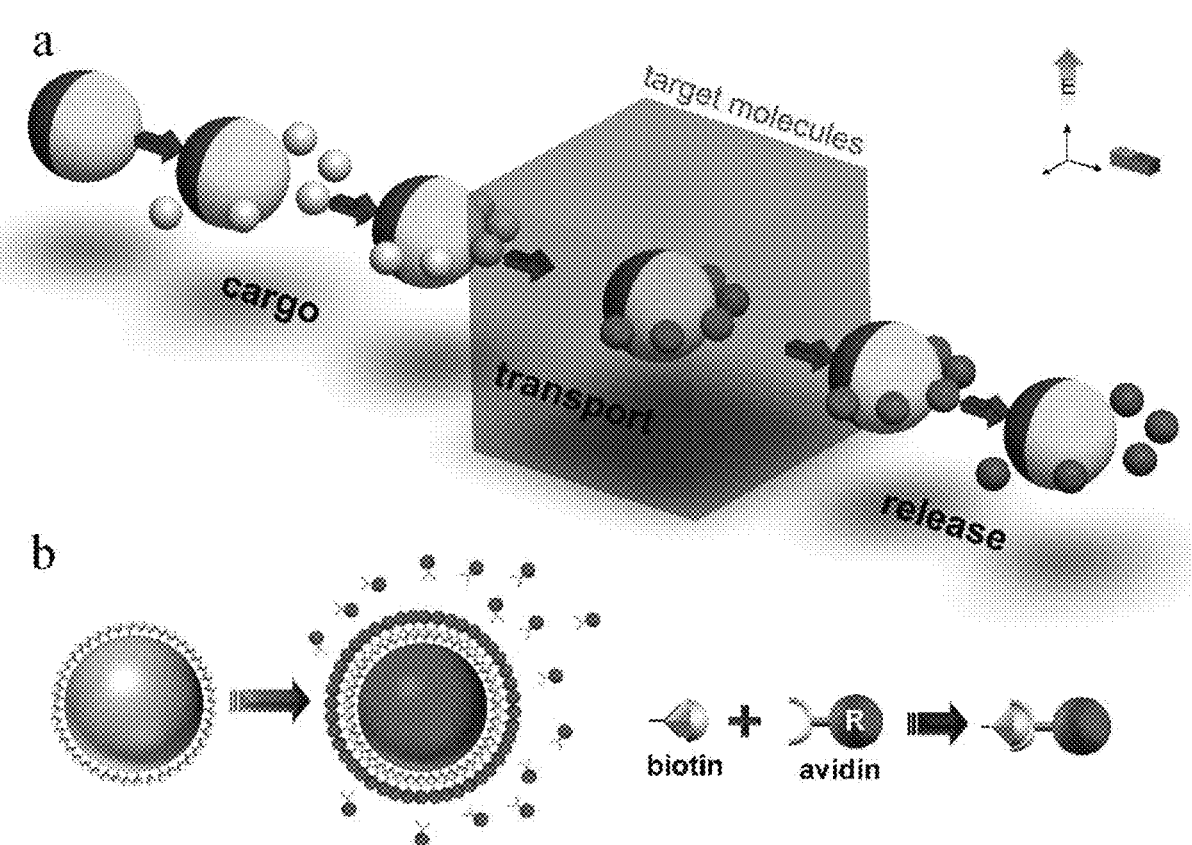
FIGS. 15A and 15B are schematic illustration of a concept of a micromotor-based biosensing by cargo manipulation and transport of functionalized beads. a) A Janus particle picks up biotin-functionalized beads and transports them to selected regions. Electric field is used for both JP propulsion and cargo manipulation (negative DEP trapping), while magnetic field is used for steering the JP. The metallic coated (Cr/Ni/Au) is colored yellow while the non-fluorescent bare polystyrene hemisphere is colored dark grey. The red and grey colored cargos indicate the biotin-functionalized particles with and without avidin-biotin binding, respectively; b) biotin-avidin reactions are used as a simplified model of immunosensing and DNA biosensing wherein the biotin coated beads binds to avidin molecules that are introduced into the sample solution.

This Example presents a micromotor-based biosensing using simplified microfluidic devices consisting of either a single chamber (FIGS. 13A-B) or two chambers with connecting microchannel (FIGS. 14A-E). As described in the schematics of FIGS. 15A and 15B the micromotor first loads the functionalized beads as cargos and then transport them towards the sample of the target analyte for some certain incubation time for its "on the fly" binding with specific molecular probes that are functionalized on the surface of the beads. This is followed by a washing step wherein the beads are transported into a region free of the target analyte for visualization of the binding before release. The micromotor can be reused to load and transport new cargos following release of the previously transported cargos. Without loss of generality, biotin-avidin with high affinity was used as a simplified model for immunosensing or protein and nucleic acid detection. While micromotor based cargo loading was previously studied, this example investigates its applicability for biosensing using functionalized microbeads. This involves consideration of the diffusion of the analyte within the microfluidic chamber as well as the dependency of the bimolecular binding between target analyte and surface immobilized probes on the analyte concentration as well as the retention time within the region where the analyte is introduced.

Materials and Methods

Preparation of Magnetic Janus Particles (JPs)

Janus particles (10 μm in diameter) were fabricated by coating non-fluorescently tagged polystyrene (Ps) particles (Sigma Aldrich) with 15 nm Cr, followed by 50 nm Ni and 15 nm Au layers using electron-beam evaporator, as described in the protocol in Ref 19. Before releasing the JPs from the glass slides, the JPs were magnetized by placing the slide in between two neodymium magnetic blocks with opposite dipoles. The released JPs by sonication in Deionized (D.I) water were further rinsed three times by DI water with 0.02% v/v of non-ionic surfactant, Tween 20 (Sigma Aldrich). The concentration of JPs within the microchamber was diluted so as to minimize the possible interaction between the JPs.

Microfluidic Chip Fabrication and Experimental Setup

The single microchamber device consisted of a circular microfluidic chamber made of spacer (120 μm in height, 9 mm in diameter, Grace-Bio) sandwiched between two Indium Tin Oxide (ITO)-coated glass slides (Delta Technologies). The bottom ITO-coated glass slide was further coated with 15 nm-thick silicon dioxide using sputter (AJA international Inc., ATC 2200) to suppress adsorption of the particles onto the substrate. Two inlet holes (about 1 mm in diameter, 6.5 mm in distance) were drilled at the top of chamber, to introduce JPs, functionalized particles and target sample analyte via manual pipetting. Above the holes, additional PBS solution was filled within a surrounding silicone reservoir (2 mm in height, 9 mm in diameter, Grace-Bio) to prevent evaporation of solution within the chamber and to minimize possible flow within the microfluidic chamber during experiment (see the side view of FIG. 13A). The two microchamber device consist of microchambers identical to the one described above and a connecting microfluidic channel (250 μm in height, 3.5 mm in length), which was fabricated using a laser cutting machine (FIG. 14A).

The AC electric field was applied between the two ITO surfaces using a function generator (TTi TGA 12104 series) and monitored by an oscilloscope (Tektronix, TPS-2024). The steering of JP motion was controlled using a rotating external permanent magnet (neodymium, 14×12×19 mm$^3$, 48.8 of (BH)max/MGOe). The magnet was kept about 15 cm away from the center of the device in order to minimize the effect of magnetic force (via magnetophoresis due to field gradients) on JP's motion. All experiments were recorded using Andor Neo sCMOS camera attached to an inverted epi-fluorescent microscope (Nikon, Eclipse Ti-U) with 10× or 20× objective lens. The motions of the JPs and the fluorescent intensities of the cargos after binding events were further analyzed using image J software.

Binding of Avidin and Biotin-Conjugated Particles

As for functionalized beads, commercially available 3.05 μm-diameter biotin-conjugated polystyrene particles (Spherotech) were used and Rhodamine-tagged avidin D (Vector Laboratories) served as the target molecules. The Biotin-conjugated particles (0.02% w/v) were rinsed three time using 0.01× diluted Phosphate-buffered saline, PBS (σ=170 μS cm$^{-1}$) with 0.01% v/v Tween 20 in order to minimize adhesion to the substrate before being injected into the microfluidic chamber. A volume of 3 μL of the biotin-conjugated particles mixed with JPs in 0.01× PBS was introduced into the microchamber, followed by the gentle introduction of 2 μL solution of various concentrations of avidin molecules within one of the holes. The biotin-conjugated particles, which located or transported by JPs at the area where avidin analyte exists, were incubated with avidin (2-200 μg mL$^{-1}$), for 5 to 20 min, at room temperature. After binding, the cargos followed a washing step by being transported via JPs to a region which is free of avidin analyte. Their binding with biotin (affinity of $K_d$ of about 10$^{-15}$M) was detected by measuring the fluorescence intensity. As a control, non-specific binding between avidin molecule (200 μg mL$^{-1}$) and the non-biotin-functionalized Ps particles (3 μm in diameter, Thermoscientific) was examined using same protocol with incubation time of 25 min.

Numerical Simulations

Asymmetric electric field distribution in the proximity of a Janus sphere near conducting surface, via two-dimensional (2D), stationary electrostatic model was simulated using COMSOL 5.3. 2D geometry consists of a rectangular environment (100 μm in height, 200 μm in width) with a 10 μm-diameter circular Janus particle, which is placed 1 μm above bottom substrate. The system was supplemented by the following boundary and interface conditions: at the bottom substrate, the electric potential was V (10 V), while top wall was set as ground. At the metallic and dielectric hemispheres of the JP, a floating electrode and insulating boundary were respectively assumed. This is valid for high frequencies, much beyond the RC time of the induced charge, hence, its screening effect of the metallic hemisphere can be neglected.

Results

Cargo Loading and Transport

The cargo (biotin-coated beads) manipulation (loading, transport and release) was characterized. A 10 μm-diameter Ni-Au coated-Janus particle was used as a micromotor within an Indium Tin Oxide(ITO)-sandwiched microchamber wherein the bottom ITO-coated glass slide was covered with thin silicon dioxide layer to suppress adsorption of particles onto the substrate. The effect of the conductivity of a Phosphate-buffered saline (PBS) solution on the micromotor velocity (FIGS. 16B, 17) was examined. As seen the electrokinetic propulsion of the JP becomes ineffective at high solution conductivities (>1 mS/cm). The chosen solution conductivity at which the study was performed was 0.01% (v/v) PBS at which the JPs moves fast enough to shorten the translocation time between the different regions but also enables sufficiently strong biotin-avidin binding affinity.

Figure 16A:
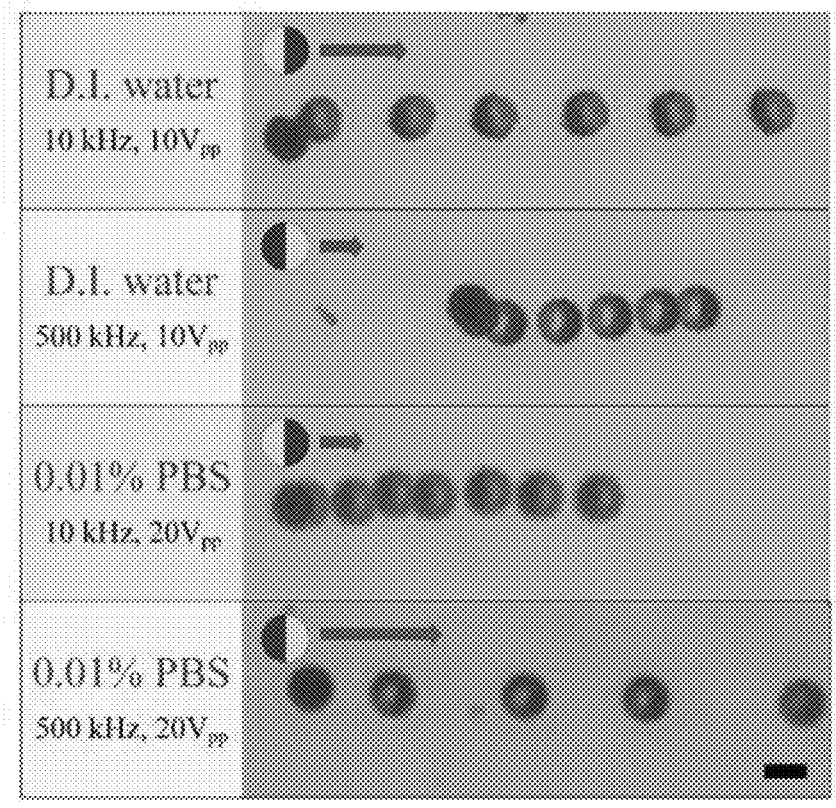
FIGS. 16A-D show characterization of self-propulsion of Janus particle and cargo transport of biotin-coated particles. (a) Superimposed sequential microscope images showing the transport of 10 μm (in diameter) Cr/Ni/Au coated Janus particle suspended in Deionized (D.I) water and 0.01% diluted PBS with conductivity (σ=180 μS cm$^{-1}$). The JP motion is due to ICEP (Polystyrene (PS) hemisphere forward) and sDEP (Au hemisphere forward) at electric field frequencies of 10 kHz and 500 kHz, respectively. The red arrows indicate the direction of motion of the JP and time interval between superimposed images is 2 s. (b) Frequency dispersion of the Janus particle mobility at various solutions. The black line indicates the Clausius-Mossotti (CM) factor of a 3.5 μm (in diameter) biotin-coated particles (cargos) in 0.01% PBS (σ=170 μS cm$^{-1}$) as extracted from their DEP response. (c) Superimposed images showing the pickup process of cargos by a single JP suspended in 0.01% diluted PBS. The applied electric field is 500 kHz, 20 $V_{pp}$, which results in sDEP dominated JP propulsion and nDEP trapped cargos that assemble on the equator of the JP. The red arrow indicates the direction of the JP steered by magnetic force. (d) Carrier velocity vs. the number of cargos under electric field of 500 kHz and 10 $V_{pp}$. The bottom insets depicts the distribution of the electric field around the JP as obtained from the numerical simulations and corresponding locations where positive and negative DEP trapping of cargo can occur. Microscope images in the insets depict varying number of nDEP trapped cargos. Scale bars: 10 μm.
Figure 16B:
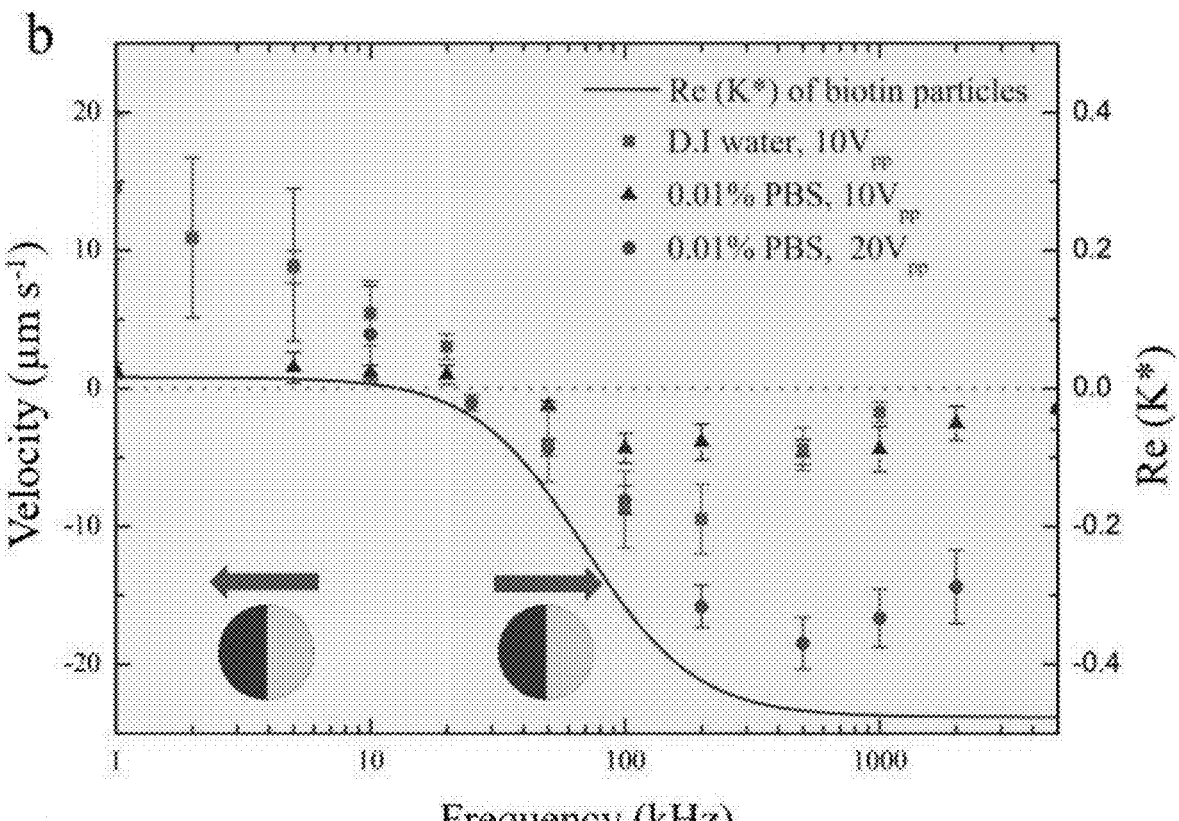

As seen in FIGS. 16A-B there are two modes of self-propulsion, where the JP moves with its dielectric end forward under induced-charge electro-phoresis (ICEP) at low frequencies and with its metallic end forward (sDEP) beyond a certain critical frequency. Also, the applied electric field frequency affects the dielectrophoretic response of the cargos, which transition from pDEP to nDEP response with increasing frequency beyond the crossover frequency (COF) between 5 to 10 kHz (FIG. 16B).

Figure 16C:
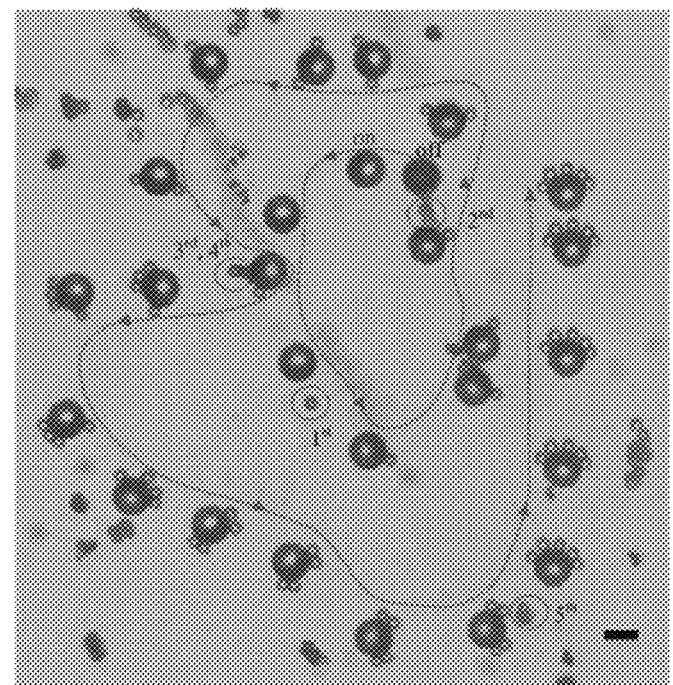
Figure 16D:
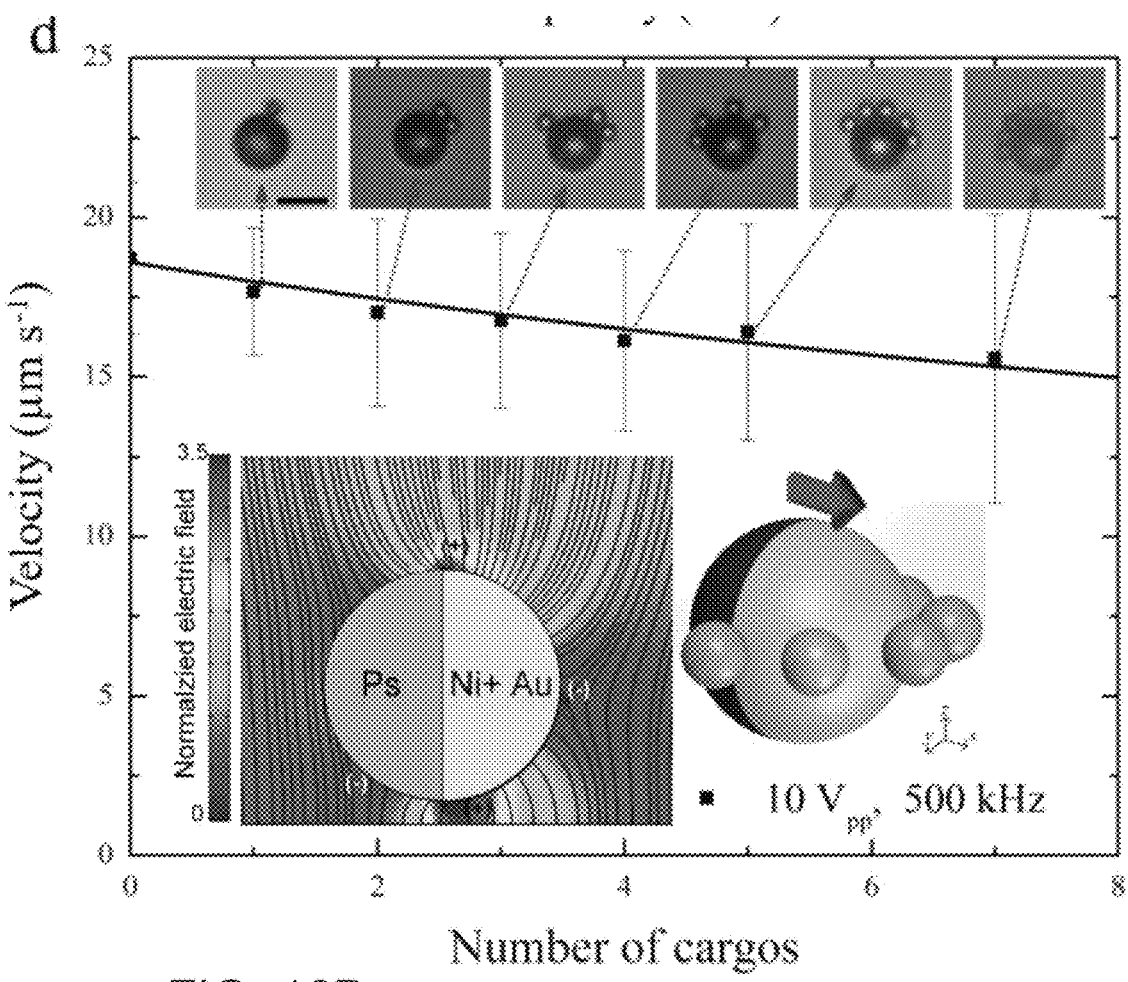
Figure 17:
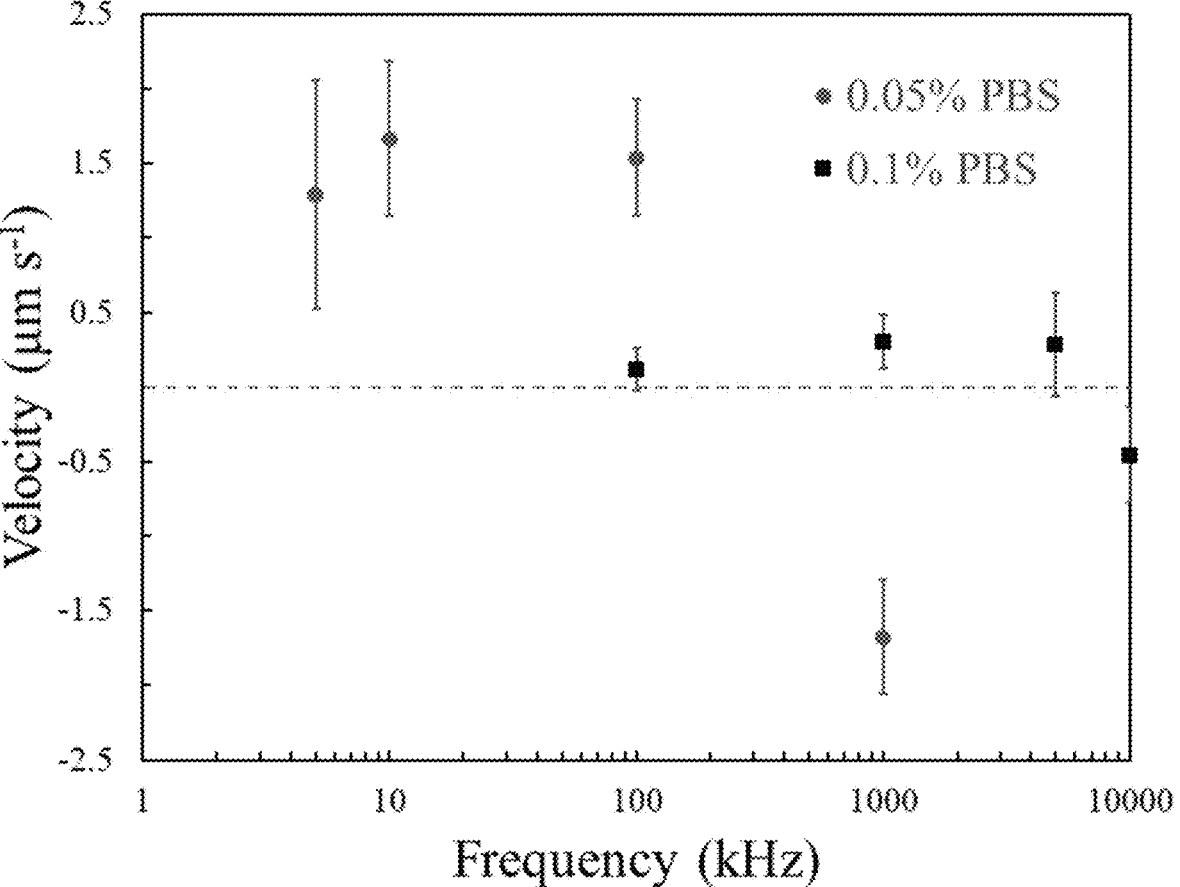
FIG. 17 shows frequency dispersion of the Janus particle mobility within solutions of higher conductivity, 0.1% and 0.05% PBS with corresponding conductivity of 1.68 and 0.87 mS cm$^{-1}$.
Figure 18A:
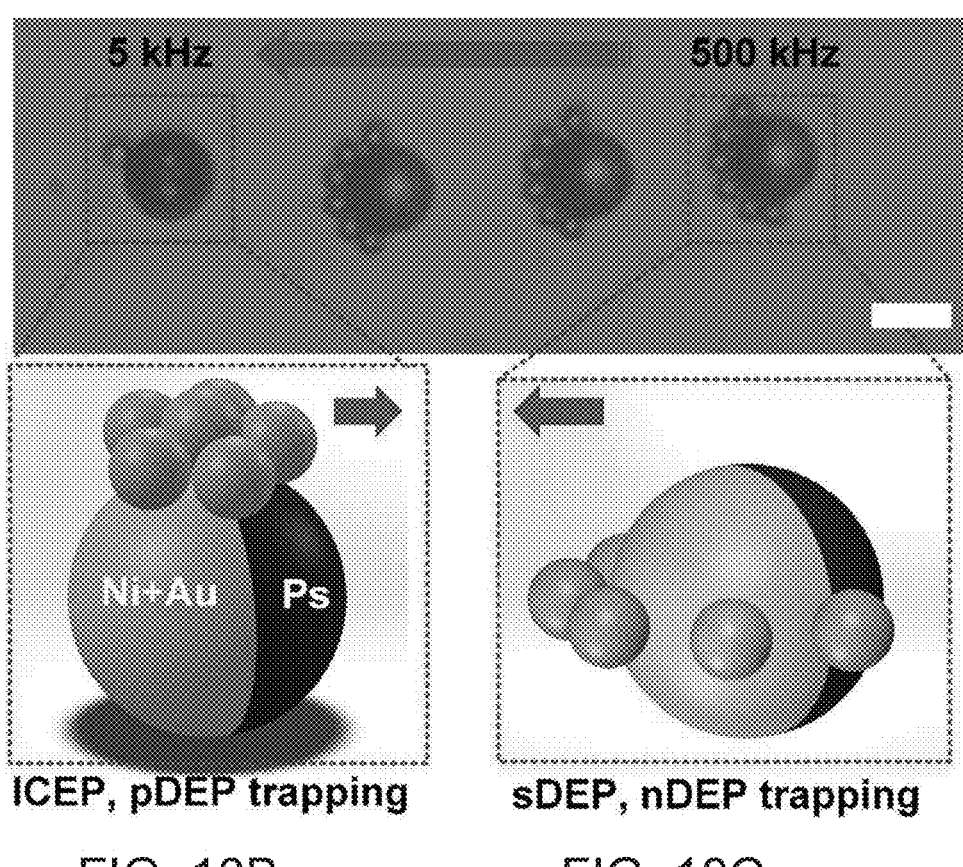

The sDEP propulsion mode with nDEP cargo trapping (500 kHz) was chosen due to the larger cargo loading capacity (there is less hydrodynamic shear since electro-convection is significantly reduced at such high frequencies) and the relatively large carrier mobility. At lower frequency (5 kHz) with ICEP propulsion and pDEP cargo trapping mode, the cargos were trapped only at the top of the JP (see simulation inset in FIG. 16D) due to its inability to penetrate underneath the JP due to size limitation, but transported with a non-smooth motion due to abrupt stops as a result of the loaded cargo (FIG. 17). At the mode of sDEP and nDEP cargo trapping, the micromotor with magnetic steering is directed to capture functionalized beads in a consecutive manner with particles trapped on the equator of its metallic hemisphere as seen in (FIG. 16C, inset of FIG. 16D). FIG. 16D depicts how the increased number of loaded cargo is decreasing the mobility of the micromotor. This can be explained due to the increased Stokes drag resulting from the enlarged areal cross-section of the loaded carrier due to the trapped cargos. The maximal cargo loading capacity the micromotor is able to pick up was about 7 for the current operating conditions. However, the maximal loading capacity can be changed depending on the JP size and operating conditions (see FIGS. 18A-C).

A Single Microfluidic Chamber Setup

Figures 19A, 19B:
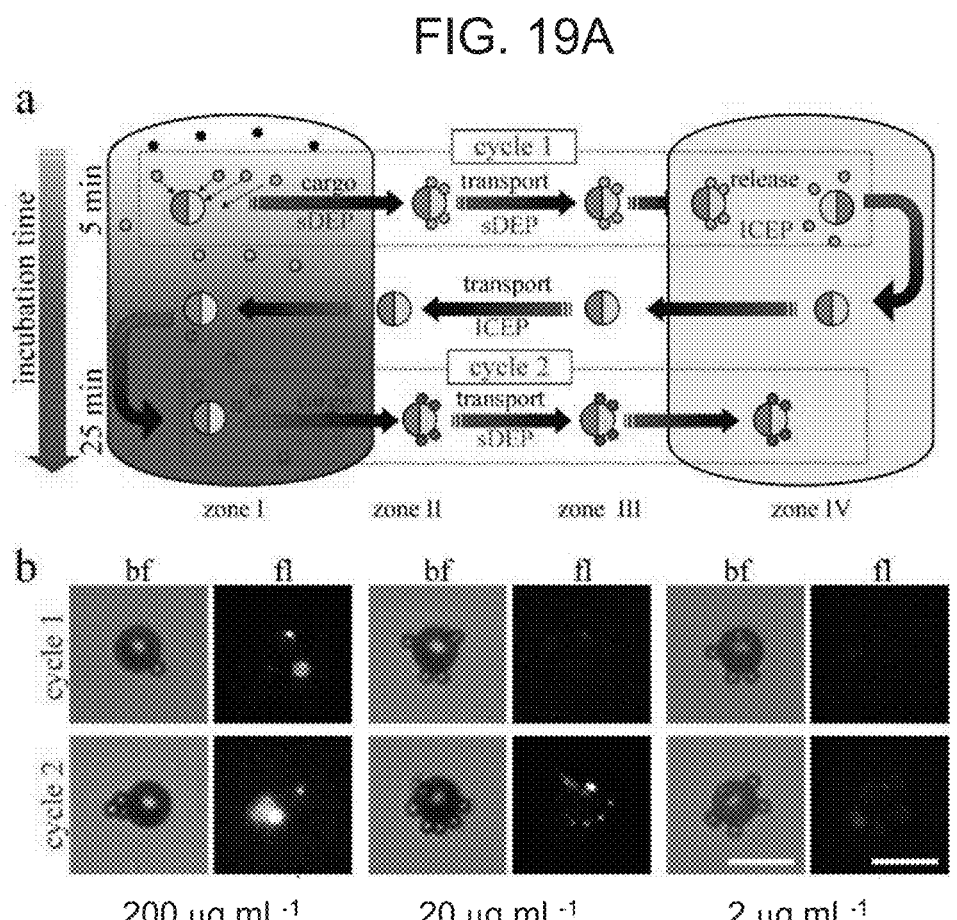
FIGS. 19A-C show several cycles of transport of bio-functionalized cargos within a single chamber system. (A) Schematics describing 2 cycles of cargo transport from zone I to zone IV (see FIGS. 13A-B). The color change from orange to red indicates qualitatively the enhanced binding between avidin and biotin-particles with increasing incubation time in zone I. After releasing the cargos at the end of first cycle, the JP went back to zone I with propulsion mode of ICEP (10 kHz, 20 $V_{pp}$) in order to prevent loading cargos on the way. The incubation times of avidin-biotin binding are 5 and 25 min at cycle 1 and 2, respectively. (B) Microscope images of the transported cargo at zone IV with bright field and fluorescent mode for various initial avidin concentrations loaded at zone I. (C) Fluorescent intensity of avidin bound to biotin-coated cargos vs. various initial avidin concentrations and two transport cycles. Microscope images in the inset show non-biotin coated beads (cargos) at zone IV under 200 μg mL$^{-1}$ of initial avidin concentration and 25 minutes incubation time as a control test. White scale bar: 15 μm.
Figure 19C:
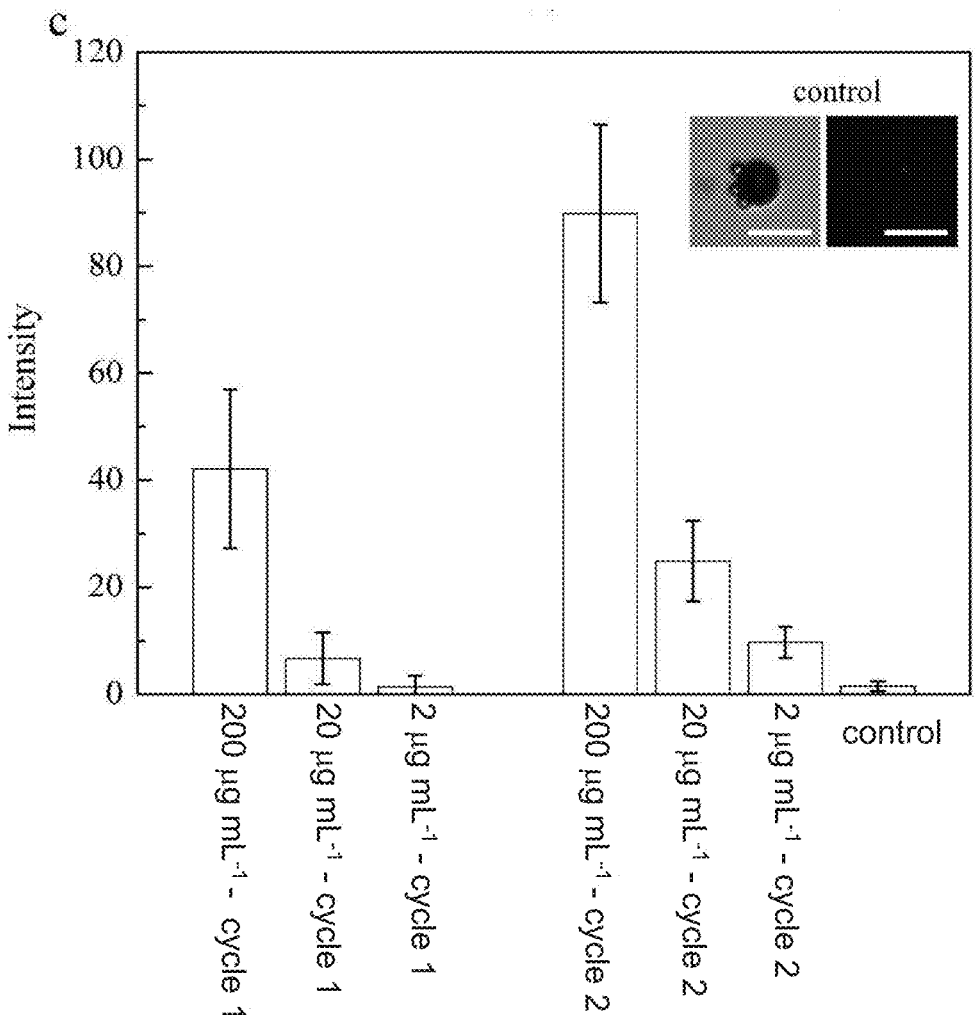
Figures 20A, 20B, 20C, 20D, 20E, 20F:
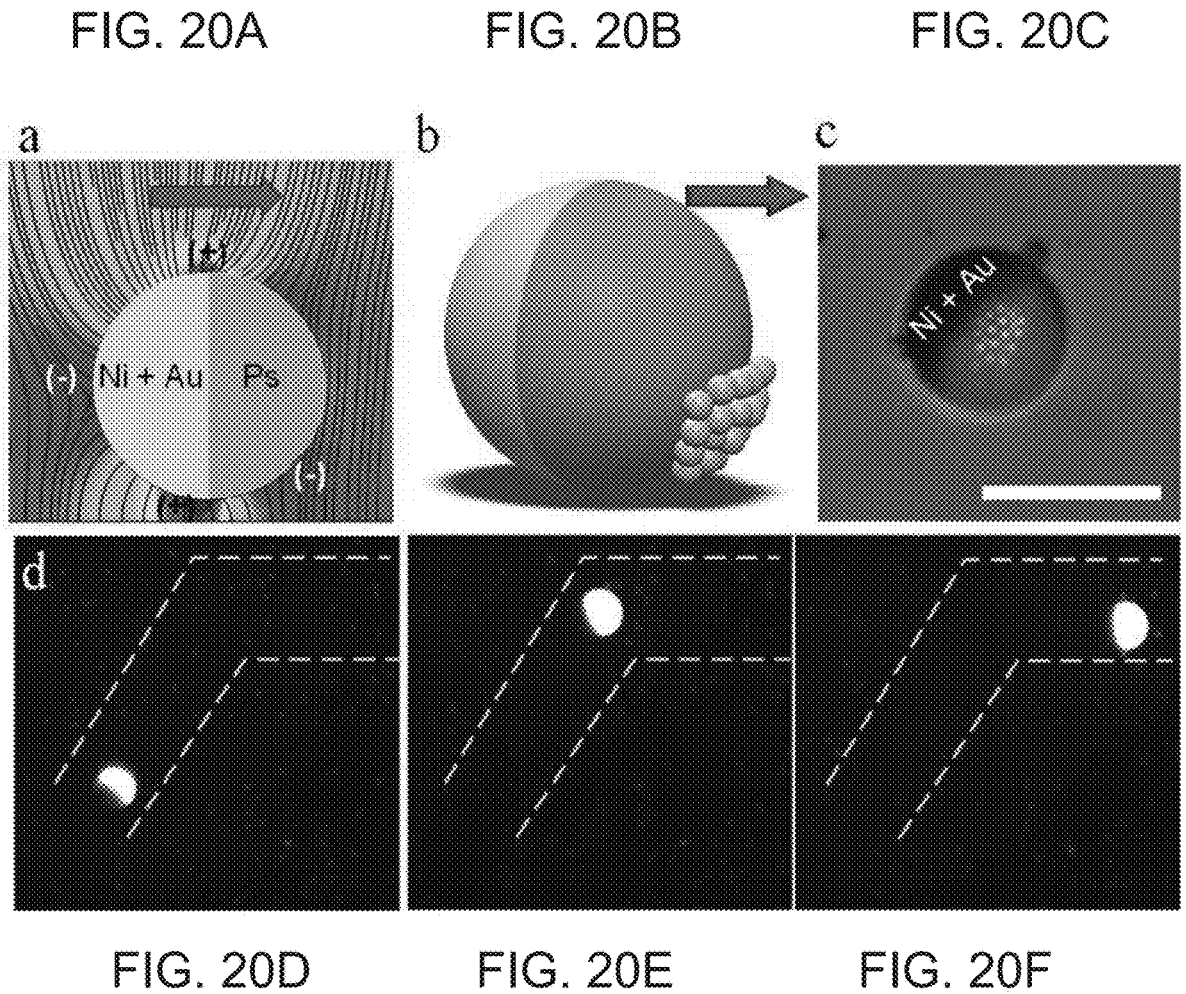
FIGS. 20A-F shows cargo loading and transport using a 27 μm-diameter Janus particle micromotor at low frequency (20 kHz, 20 $V_{pp}$). (A) Numerical simulation of the electric field distribution indicating the regions (red-dot circle) where negative DEP trapping of cargos occurred. A 3D schematic (B) and microscopic image (C) show that the micromotor translates with its dielectric (green color) hemisphere forward by ICEP and biotin-coated particles undergo nDEP trapping. The white scale bar is 30 μm. (D-F) time-lapse images showing transport of the micromotor and the trapping of the avidin bound biotin-particles placed along the way.

The sensing of the present embodiments was demonstrated using a very simplified microfluidic setup consisting of a single chamber made of a spacer and two drilled inlet holes for introduction of the solution, functionalized beads, micromotor and sample analyte (FIGS. 13A-B). One can qualitatively differentiate between several zones in between one of the inlets where the target sample analyte is gently introduced and the other inlet which is free of target analyte. Note that the distance between the two holes (6.5 mm) is far enough for the target analyte not to reach the other channel by diffusion during the whole process, (about 180 hours with avidin molecule diffusion coefficient D of about 6.5×10$^{-7}$ cm$^2$s$^{-1}$). The micromotors and cargos (functionalized beads) were first introduced uniformly within the chamber before introducing the target analyte, although, could be as well introduced only into the inlet far from the analyte after filling the chamber with the solution. The micromotor was then used to trap the cargos to follow a path along the avidin molecule concentration gradients for binding followed by a washing step. The binding of avidin molecules to the biotin coated beads did not seem to change their DEP behavior in a way that necessitates readjusting the operating parameters. The time of incubation can be then controlled by either increasing the retention time of the micromotor with loaded cargos within region I of the highest avidin concentration or by simply picking up the beads within region I after some desired time (FIGS. 19A-C). As shown in FIG. 13B, a clear binding event occurred between the avidin and the biotin-coated cargos following an incubation time of ~5 minutes. This shortened detection time, relative to the long diffusion time of avidin within the chamber, is clearly due to motion of the trapped cargos, via the micromotor, to the region of high analyte concentration. This is further quantified using different avidin concentrations to test the limit of detection of the system which proves that for two cycles concentration as low as 2 μg/mL can be detected. It is expected that this can be further improved by simply increasing the incubation time (FIG. 19C). As a control, a non-biotin coated microparticles of the same size which showed no fluorescent signal when compared to the functionalized beads were used (inset of FIG. 19C).

Extension to More Complicated Microchannel Geometries

In some embodiments of the present invention additional chambers are employed, for example, to perform multiplex (involving different functionalized beads), sandwich immunoassay or several washing/buffer exchange/chemical reaction steps. For proving the applicability of the generic micromotor based functionalized-cargo transport of the present embodiments to these realizations of biosensing, a two microchamber device with connecting microfluidic was fabricated using direct laser cutting (FIGS. 14A-E). It is demonstrated that the JP can travel very long distances (through the connecting microchannel) while transporting cargo.

This Example successfully demonstrated the ability to perform label-free and dynamic manipulation and transport of biotin coated beads used as cargo via a JP acting as an active carrier. The ability to perform cargo loading under various solution conductivities was examined, including one (PBS) that is can be used for the binding of biotin-avidin. It was demonstrated that using a single microfluidic chamber a simple and robust biosensing could be realized with the advantages of a micromotor based approach avoiding the need for fluid handling as incubation time and washing steps can be simply controlled by moving the carrier itself. The inventors demonstrated the ability of transporting such loaded carrier for very long distances through a microchannel connecting between two microchambers which may be important for realizations of several buffer exchange and/or washing steps and/or multiplex sensing. This approach is applicable for a broad range of cargos from diameters of about 100 nm size to diameters of several microns. Also contemplated is the use of mixed population of cargos for multiplex biosensing where their loading/release can be controlled individually by taking advantage of their unique polarizability relative to the medium (Clausius-Mossotti factor) and the associated different cross-over frequencies (COFs) at which the cargo switches between positive- and negative-DEP responses.

Although this Example used biotin-avidin reaction, the technology of the present embodiments can be applied for any antibody-antigen or DNA-probe combination. It can also include more microchambers for several reagents and washing steps as for example in a sandwich immunoassay where a reporting antibody is used for the fluorescent signal following the antigen binding to the antibodies immobilized on the surface of the cargos. Although there was no observed significant effect of the binding on the DEP behavior of the cargos, such that necessitates tuning of the operating conditions, the operating frequency can be tuned if there is such an effect. The method of the present embodiments is particularly useful for low concentration of the target analytes where the fast transportation of the carrier and trapped cargo towards the analyte region and away from it (washing step) enables fast detection that otherwise would be long due to the slow diffusion processes. Also, while this Example demonstrated this using a single JP guided using magnetic steering so as to precisely control its translocation between the different regions and its incubation time within the region into which the analyte is introduced (region I), an operation mode where several such carriers are operating autonomously (without magnetic steering) so as to enhance sampling of the analyte (e.g., reducing the otherwise long diffusion time) is also contemplated.

The current study used a relatively low conductivity 0.01% (v/v) PBS solution at which the JP moves fast with a sufficiently strong biotin-avidin binding affinity. This is because electrokinetic propulsion is typically effective with solution conductivities lower than about 1 mS/cm. However, the cargo manipulation via DEP on the surface of the JP of the present embodiments can also be applied with physiological solutions of higher conductivity. The propulsion mechanism can be ensured, for example, by utilizing a rotating magnetic field. Also contemplated are embodiments in which the quenching of the EDL is suppressed to higher solution conductivity using ion conductive polyelectrolyte coating.

REFERENCES FOR EXAMPLE 2

(1) Sadik, O. A.; Van Emon, J. M. Applications of Electrochemical Immunosensors to Environmental Monitoring. Biosens. Bioelectron. 1996, 11 (8), i-x.
(2) Xu, D.; Wang, Y.; Liang, C.; You, Y.; Sanchez, S.; Ma, X. Self-Propelled Micro/Nanomotors for On-Demand Biomedical Cargo Transportation. Small 2019, 1902464.
(3) Kherzi, B.; Pumera, M. Self-Propelled Autonomous Nanomotors Meet Microfluidics. Nanoscale 2016, 8 (40), 17415-17421.
(4) Xu, T.; Gao, W.; Xu, L. P.; Zhang, X.; Wang, S. Fuel-Free Synthetic Micro/Nanomachines. Adv. Mater. 2017, 29 (9).
(5) Chen, C.; Soto, F.; Karshalev, E.; Li, J.; Wang, J. Hybrid Nanovehicles: One Machine, Two Engines. Adv. Funct. Mater. 2019, 29 (2), 1-10.
(6) Sanchez, S.; Soler, L.; Katuri, J. Chemically Powered Micro- and Nanomotors. Angew. Chemie—Int. Ed. 2015, 54 (5), 1414-1444.
(7) Kong, L.; Guan, J.; Pumera, M. Micro- and Nanorobots Based Sensing and Biosensing. Curr. Opin. Electrochem. 2018, 10, 174-182.
(8) Garcia, M.; Orozco, J.; Guix, M.; Gao, W.; Sattayasamitsathit, S.; Escarpa, A.; Merkoei, A.; Wang, J. Micromotor-Based Lab-on-Chip Immunoassays. Nanoscale 2013, 5 (4), 1325-1331.
(9) Sanchez, S.; Solovev, A. A.; Harazim, S. M.; Schmidt, O. G. Microbots Swimming in the Flowing Streams of Microfluidic Channels. J. Am. Chem. Soc. 2011, 133 (4), 701-703.
(10) Baraban, L.; Tasinkevych, M.; Popescu, M. N.; Sanchez, S.; Dietrich, S.; Schmidt, O. G. Transport of Cargo by Catalytic Janus Micro-Motors. Soft Matter 2012, 8 (1), 48-52.
(11) Brooks, A. M.; Tasinkevych, M.; Sabrina, S.; Velegol, D.; Sen, A.; Bishop, K. J. M. Shape-Directed Rotation of Homogeneous Micromotors via Catalytic Self-Electrophoresis. Nat. Commun. 2019, 10 (1), 495.
(12) Mirin, N. A.; Halas, N. J. Light-Bending Nanoparticles 2009. Nano Lett. 2009, 9 (3), 1255-1259.
(13) Maggi, C.; Saglimbeni, F.; Dipalo, M.; De Angelis, F.; Di Leonardo, R. Micromotors with Asymmetric Shape That Efficiently Convert Light into Work by Thermocapillary Effects. Nat. Commun. 2015, 6, 1-5.
(14) Wang, W.; Castro, L. A.; Hoyos, M.; Mallouk, T. E. Autonomous Motion of Metallic Microrods Propelled by Ultrasound. ACS Nano 2012, 6 (7), 6122-6132.
(15) Sinn, I.; Kinnunen, P.; Pei, S. N.; Clarke, R.; McNaughton, B. H.; Kopelman, R. Magnetically Uniform and Tunable Janus Particles. Appl. Phys. Lett. 2011, 98 (2), 024101.

35

(16) Fei, W.; Driscoll, M. M.; Chaikin, P. M.; Bishop, K. J. M. Magneto-Capillary Dynamics of Amphiphilic Janus Particles at Curved Liquid Interfaces. Soft Matter 2018, 14 (23), 4661-4665.

(17) Gao, W.; Kagan, D.; Pak, O.; Clawson, C. Cargo-Towing Fuel-Free Magnetic Nanoswimmers for Targeted Drug Delivery. small 2012, 8 (3), 460-467.

(18) Qiu, F.; Nelson, B. J. Magnetic Helical Micro- and Nanorobots: Toward Their Biomedical Applications. Engineering 2015, 1 (1), 021-026.

(19) Boymelgreen, A.; Yossifon, G.; Miloh, T. Propulsion of Active Colloids by Self-Induced Field Gradients. Langmuir 2016, 32 (37), 9540-9547.

(20) Boymelgreen, A. M.; Balli, T.; Miloh, T.; Yossifon, G. Active Colloids as Mobile Microelectrodes for Unified Label-Free Selective Cargo Transport. Nat. Commun. 2018, 9 (1), 760.

(21) Han, K.; Shields, C. W.; Velev, O. D. Engineering of Self-Propelling Microbots and Microdevices Powered by Magnetic and Electric Fields. Adv. Funct. Mater. 2018, 28 (25), 1-14.

(22) Orozco, J.; Cortés, A.; Cheng, G.; Sattayasamitsathit, S.; Gao, W.; Feng, X.; Shen, Y.; Wang, J. Molecularly Imprinted Polymer-Based Catalytic Micromotors for Selective Protein Transport. J. Am. Chem. Soc. 2013, 135 (14), 5336-5339.

(23) Delezuk, J. A. M.; Ramirez-Herrera, D. E.; Esteban-Fernindez de Ávila, B.; Wang, J. Chitosan-Based Water-Propelled Micromotors with Strong Antibacterial Activity. Nanoscale 2017, 9 (6), 2195-2200.

(24) Wu, Z.; Li, J.; De Avila, B. E. F.; Li, T.; Gao, W.; He, Q.; Zhang, L.; Wang, J. Water-Powered Cell-Mimicking Janus Micromotor. Adv. Funct. Mater. 2015, 25 (48), 7497-7501.

(25) Morales-Narváez, E.; Guix, M.; Medina-Sánchez, M.; Mayorga-Martinez, C. C.; Merkoçi, A. Micromotor Enhanced Microarray Technology for Protein Detection. Small 2014, 10 (13), 2542-2548.

(26) Esteban-Fernández De Ávila, B.; Martín, A.; Soto, F.; Lopez-Ramirez, M. A.; Campuzano, S.; Vásquez-Machado, G. M.; Gao, W.; Zhang, L.; Wang, J. Single Cell Real-Time MiRNAs Sensing Based on Nanomotors. ACS Nano 2015, 9 (7), 6756-6764.

(27) Yan, J.; Han, M.; Zhang, J.; Xu, C.; Luijten, E.; Granick, S. Reconfiguring Active Particles by Electrostatic Imbalance. Nat. Mater. 2016, 15 (10), 1095-1099.

(28) Lin, C. H.; Chen, Y. L.; Jiang, H. R. Orientation-Dependent Induced-Charge Electrophoresis of Magnetic Metal-Coated Janus Particles with Different Coating Thicknesses. RSC Adv. 2017, 7 (73), 46118-46123.

(29) Squires, T. M.; Bazant, M. Z. Breaking Symmetries in Induced-Charge Electro-Osmosis and Electrophoresis; 2006; Vol. 560.

(30) Gangwal, S.; Cayre, O. J.; Bazant, M. Z.; Velev, O. D. Induced-Charge Electrophoresis of Metallodielectric Particles. Phys. Rev. Lett. 2008, 100 (5), 1-4.

(31) Pethig, R. Review—Where Is Dielectrophoresis (DEP) Going? J. Electrochem. Soc. 2016, 164 (5), B3049-B3055.

(32) Honegger, T.; Berton, K.; Picard, E.; Peyrade, D. Determination of Clausius-Mossotti Factors and Surface Capacitances for Colloidal Particles. Appl. Phys. Lett. 2011, 98 (18), 181906.

(33) Jones, T. B. Liquid Dielectrophoresis on the Microscale. J. Electrostat. 2001, 51-52 (1-4), 290-299.

(34) Tottori, S.; Zhang, L.; Qiu, F.; Krawczyk, K. K.; Franco-Obregõn, A.; Nelson, B. J. Magnetic Helical

36

Micromachines: Fabrication, Controlled Swimming, and Cargo Transport. Adv. Mater. 2012, 24 (6), 811-816.

(35) Demirörs, A. F.; Akan, M. T.; Poloni, E.; Studart, A. R. Active Cargo Transport with Janus Colloidal Shuttles Using Electric and Magnetic Fields. Soft Matter 2018, 14 (23), 4741-4749.

(36) Huo, X.; Wu, Y.; Boymelgreen, A.; Yossifon, G. Analysis of Cargo Loading Modes and Capacity of an Electrically-Powered Active Carrier. 2019.

(37) Demirö, A. F.; Mehmet, ‡; Akan, T.; Poloni, E.; Studart, A. R. Active Cargo Transport with Janus Colloidal Shuttles Using Electric and Magnetic Fields †. Soft Matter 2018, 14, 4741.

(38) Wayment, J. R.; Harris, J. M. Biotin-Avidin Binding Kinetics Measured by Single-Molecule Imaging. Anal. Chem. 2009, 81 (1), 336-342.

(39) Yasukawa, T.; Suzuki, M.; Sekiya, T.; Shiku, H.; Matsue, T. Flow Sandwich-Type Immunoassay in Micro-fluidic Devices Based on Negative Dielectrophoresis. Biosens. Bioelectron. 2007, 22 (11), 2730-2736.

(40) Wagner, B.; Freer, H. Development of a Bead-Based Multiplex Assay for Simultaneous Quantification of Cytokines in Horses. Vet. Immunol. Immunopathol. 2009, 127 (3-4), 242-248.

(41) Yu, X.; Hartmann, M.; Wang, Q.; Poetz, O.; Schnei-derhan-Marra, N.; Stoll, D.; Kazmaier, C.; Joos, T. O. MFBI. A Microfluidic Bead-Based Immunoassay for Multiplexed Detection of Proteins from a ML Sample Volume. PLoS One 2010, 5 (10), e13125.

(42) Kaewsaneha, C.; Tangboriboonrat, P.; Polpanich, D.; Eissa, M.; Elaissari, A. Janus Colloidal Particles: Preparation, Properties, and Biomedical Applications. ACS Appl. Mater. Interfaces 2013, 5 (6), 1857-1869.

(43) Cui, J.; Huang, T. Y.; Luo, Z.; Testa, P.; Gu, H.; Chen, X. Z.; Nelson, B. J.; Heyderman, L. J. Nanomagnetic Encoding of Shape-Morphing Micromachines. Nature 2019, 575 (7781), 164-168.

(44) Zhan, X.; Wang, J.; Xiong, Z.; Zhang, X.; Zhou, Y.; Zheng, J.; Chen, J.; Feng, S. P.; Tang, J. Enhanced Ion Tolerance of Electrokinetic Locomotion in Polyelectro-lyte-Coated Microswimmer. Nat. Commun. 2019, 10 (1), 1-9.

(45) Park, S.; Yossifon, G. Combining Dielectrophoresis and Concentration Polarization-Based Preconcentration to Enhance Bead-Based Immunoassay Sensitivity. Nanoscale 2019, 11 (19), 9436-9443.

(46) Shimkus, M.; Levy, J.; Herman, T. A Chemically Cleavable Biotinylated Nucleotide: Usefulness in the Recovery of Protein-DNA Complexes from Avidin Affinity Columns. Proc. Natl. Acad. Sci. U.S.A 1985, 82 (9), 2593-2597.

Example 3

Transport, Release and Mechanical Probing of Cell Organelles

The experimental system shown in FIGS. 2A-C has been successfully applied to selectively transport, release and probe cell organelles. The selectivity is driven by the different dielectrophoretic (DEP) potential wells on the JP surface that are controlled by the frequency of the electric field, along with the hydrodynamic shearing and size of the trapped organelles. Such selective and directed loading enables purification of targeted organelles of interest from a mixed biological sample while their dynamic release enables their harvesting for further analysis such as gene/RNA sequencing or proteomics. Moreover, the electro-deformation of the trapped nucleus has been shown to be in correlation with the DEP force and hence, can act as a promising label-free biomechanical marker. Hence, the active carrier constitutes an ex vivo platform for manipulation and mechanical probing of subcellular components of potential for single cell analysis.

This Example demonstrates manipulation and transport of cell organelles within a closed microfluidic cell using an electric field-powered self-propelling active particle (termed micromotor) which serves as a cargo carrier. The closed microchamber environment and directed motion option allow for superb subcellular accuracy, precluding the need for invasive external manipulation of the electrode position. Electric field-powered active particles, similar to other external fields, allow a fuel free propulsion, thereby avoiding issues of finite life and/or non-bio-compatibility of commonly used fuels and offers the ability to externally control parameters such as speed and direction in real time. In the specific case of electrokinetically driven metallodielectric Janus spheres, variation of the frequency of applied electric field has been shown to alter both the speed and direction, as the particles transition from translating with dielectric hemisphere forward under ICEP to moving with the metallic hemisphere forward under sDEP.

Combination of DEP with electrically powered active particle propulsion yields an active carrier that can selectively load, transport and release a broad range of cargos, singularly controlled by an external electric field. This unification allows for significantly simpler and more robust operation when compared to the more traditional approach to cargo transport wherein propulsion of the active carrier and cargo manipulation were often considered as separate problems.

This Example demonstrates how the micromotor can also perform as a mobile probe for performing electro-deformation of a single targeted nucleus and hence constitutes an important mechanical bio-marker. This stands in contrast to previous studies of electro-deformation of cells, atom force microscope based deformation/elasticity tools and isolated organelles, where prefabricated electrodes of fixed geometry were used.

In this Example, three organelle types are examined as cargo: nucleus, mitochondrion, and lysosome (FIG. 21B). The three differ in size, with the nucleus of a diameter of 7-10 μm, the mitochondria typically being round to oval in shape and ranging in size (semi-major and semi-minor axis) from 0.5 to 10 μm, and the lysosome with a diameter of 0.1-1.2 μm. Organelles with sizes similar to those of the nucleus and lysosome include the endoplasmic reticulum and peroxisome (0.5-1.5 μm), respectively.

Experimental Section

Magnetic Janus Particle Fabrication

Polystyrene particles (diameter: 10 μm, 15 μm) (Sigma Aldrich) in isopropanol (IPA) were pipetted onto a glass slide to form a monolayer of particles upon solvent evaporation. The glass slide was coated with 15 nm Cr, followed by 50 nm Ni and 15 nm Au, as described by Pethig et al. and Wu et al. To magnetize the JPs, the substrates were placed in between two neodymium magnetic blocks (14×12×19 mm in size), with opposite dipoles facing each other. Next, the substrate was sonicated in deionized water (DIW) with 2% Tween 20 (Sigma Aldrich), to release the JPs. The JPs were then washed three times in DIW with 0.01% Tween 20 (Sigma Aldrich) and $7\times10^{-5}$M KCl prior to the experiment.

Magnetic Steering of Janus Particles

JPs were guided by placing the neodymium magnet block (14×12×19 mm in size) at a specific orientation close to the microchamber (see FIG. 2C). The magnet was kept at a horizontal distance of 3 cm from the focus of the objective and at the same height as the microchamber. In this setup, the magnet produced an approximately uniform field of <100 Gauss within the microchamber.

Cell Culture

Organelles were isolated from HeLacells. Nucleus were also isolated from MDA-MB-231 and MCF7 cells. Cells were grown in an incubator at 37'C with a $CO_2$ content of 5% v/v. Cells were passaged every three days, establishing a new batch by adding the appropriate amount of cell suspension to the culture medium. The culture medium consisted of Dulbecco's Modified Eagle Medium (DMEM) (Biological Industries), supplemented with 10% v/v heat-inactivated foetal bovine serum (FBS), 1% v/v penicillin-streptomycin (Biological Industries), and 2% v/v L-glutamine (Biological Industries).

Isolated Cell Organelles Preparation and Labelling

HeLa, MDA-MB-231 and MCF7 cells were stained with either the fluorescent dye DAPI (Sigma Aldrich) for nucleus, (to avoid the overlap of the fluorescent from Janus particle, Propidium Iodide (PI) (Sigma Aldrich) is also used to stain the cells.) MitoTracker Red (Thermofisher) for mitochondria or LysoTracker Red for lysosomes (Thermofisher), according to the manufacturer's instructions, and then pelleted at 800×g, for 3 min, and washed twice with phosphate-buffered saline (PBS) (Thermofisher). Cells were then homogenized, with a glass homogenizer, in PBS, until 70% of the cells were homogenized. The resulting cell homogenate was centrifuged at 800×g for 3 min, to remove unbroken cells. The supernatant was centrifuged at 1.5×g, for 5 min. The resulting pellet (nucleus) was fixed with 4% v/v paraformaldehyde, at room temperature, for 30 min and then washed three times with DIW with 0.05% Tween 20 (Sigma Aldrich). The resulting supernatant was centrifuged at 7000×g to harvest mitochondria in the pellet. The mitochondria was fixed with 4% v/v paraformaldehyde, at room temperature, for 30 min and then rinsed three times with DIW. The resulting supernatant was centrifuged at 14000×g to harvest lysosomes in the pellet. The supernatant was discarded. The pellet was then fixed with 4% v/v paraformaldehyde, at room temperature, for 30 min and then rinsed three times with DIW. All other steps were performed in 4'C.

Cell Organelle Mixture Preparation and Labelling

HeLa MDA-MB-231 and MCF7 cells were stained with the DAPI or PI, MitoTracker Green and LysoTracker Red, according to the manufacturer's instructions, and then rinsed twice with low-conductivity medium (9 μS/cm). Cells were then homogenized with a glass homogenizer in low-conductivity medium, until 70% of the cells were homogenized. The supernatant was centrifuged at 800×g, for 3 min, to remove unbroken cells as pellet. The supernatant contains nucleus, mitochondria, lysosomes and other cellular components.

Transmigration Assay

An in vitro Transwell assay was conducted to investigate the deformability of cancer cells as reported(55). In brief, MCF7, HeLa and MDA-MB-231 cell lines were collected from culture dish by trypsin. After quantify the cell density, cells were washed once with serum free medium and resuspended in serum free medium at a density of 1×105 cells/ml. Equal volume of 100 μL cell suspension was seeded in Millicell Hanging Cell Culture Inserts (Millipore) with two different pore sizes of 5 μm and 8 μm. The inserts were placed in a 24-well plate containing 500 μL complete medium with 10% FBS. After 24 hours incubation, the cells in the upper chamber were removed by cotton bugs. Inserts with transmigrated cells in the outside were fixed with 4% paraformaldehyde for 30 min. After wash twice with PBS, the transmigrated cells were stained with crystal violet for 10 min. After washing the inserts for three times in DI $H_2O$, the inserts membranes were cut down and mounted on glass slides with DPX Mountant. Images were captured from six different areas for each condition.

Experimental Set-Up

The experimental chamber consisted of a 120 μm-high, silicone reservoir (Grace-Bio), sandwiched between an ITO-coated, 1 mm glass slide (Delta Technologies) and an ITO-coated coverslip (SPI systems) (see FIGS. 2A-C). Two inlet holes (~1 mm in diameter) were drilled through the top 1 mm of the ITO slide, were surrounded by a silicone reservoir (2 mm in height and 9 mm in diameter), and filled with solution, to ensure the chamber remained wet and to enable the addition of the solution with the JPs, bacteria, fluorescent dyes and tracer particles into the channel via manual pumping. AC electrical forcing was applied using a signal generator (Agilent 33250A), and monitored by an oscilloscope (Tektronix-TPS-2024).

Microscopy and Image Analysis

Trapped and untrapped nuclei, mitochondria and lysosomes were observed using a Nikon Eclipse Ti-E inverted microscope, equipped with a Yokagawa CSU-X1 spinning disk confocal scanner and Andor iXon-897 EMCCD camera. The chamber was placed with the coverslip side down and images were taken using an ×60 oil immersion lens. Stained nuclei were observed with lasers of wavelength 375 nm and 473 nm. Ten images were taken at 1 μm increments. This image series was used to reconstruct the 3D shape of the nucleus using Imaris 5.0. Stained mitochondria and lysosomes were observed with lasers of wavelength 488 nm and 561 nm.

Numerical Simulations

The numerical simulation used to qualitatively verify the presence of asymmetric electric field gradients arising from the proximity of a Janus sphere near a conducting wall, was performed in COMSOL™ 5.3. A simple 2D geometry, consisting of a rectangular channel, 80 μm height and 200 μm width, with a 10 μm diameter circle placed 300 nm above the substrate, was used to model the experimental setup. The electrostatic equations were solved in the rectangular domain, with the following boundary conditions: at the lower substrate (y=0), a voltage of 5 V was applied while the upper wall was grounded, and the edges of the channel were given an insulating boundary condition. The Janus sphere was modelled by applying a floating electrode and insulating boundary conditions at the metallic (right) and dielectric (left) hemispheres, respectively.

Results

Overview of Micromotor-Based Organelle Loading and Transport Modes

The experimental system consists of a simple microfluidic chamber formed using a spacer of 120 μm in height, positioned between two parallel indium tin oxide (ITO)-coated glass substrates (see FIGS. 2A-C). Several 10 μm or 15 μm Janus particles (JPs) are then introduced into the chamber via two 1 mm-diameter holes, along with target cell organelles. The cargo manipulation and transport of the JPs are singularly controlled using the same externally applied electric field, while directed motion is achieved using a magnetic field realized via a rotating external static magnet. The uniformity of the applied electric field is broken by the JP itself, whereby electric field gradients with positive (locations 1, 2, 3 in FIG. 21C) and negative (locations 4 and 5 in FIG. 21C) dielectrophoretic (DEP) potential wells are created at different locations on the symmetry-broken JP.

The JP has different trapping locations (FIG. 21C) formed at either local maxima electric field (locations 1-3), corresponding to positive dielectrophoretic (pDEP) trapping, or local minima (locations 4-5), corresponding to negative dielectrophoretic (nDEP) trapping. The different trapping locations (FIG. 21C) enable trapping organelles of different sizes in distinctly different locations on the JP surface. For example, while the small organelles, e.g., mitochondria and lysosomes, are trapped at the intensified electric field located between the JP and the conducting substrate (location 2 in FIG. 21C), nuclei are too large to fill the trap and hence are only trapped above the JP (location 1 in FIG. 21C).

Figure 21D:
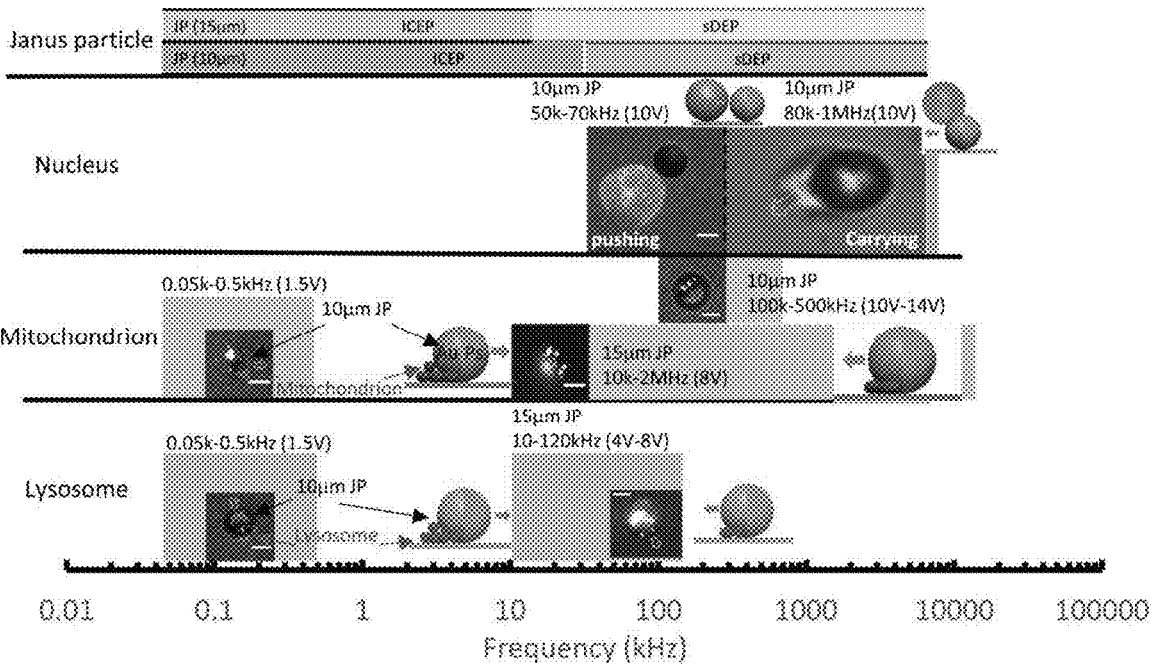

The trapping force acting on these organelles is a result of the competition between the DEP trapping force, which also depends on the location of the DEP trap, and the hydrodynamic shearing force arising from the propulsion of the micromotor. Since both the DEP force and self-propulsion strongly depend on the applied electric field frequency, this competition enables selective trapping (i.e., both location-wise and different frequency ranges) of the different organelles (see FIG. 21D). The different modes of self-propulsion and the DEP force for the various applied frequency and for different organelles (nucleus, mitochondria and lysosome) are listed in FIG. 21D. In low frequency regime (0.05 k-20 kHz), the 10 μm JP's propulsive mechanism is induced-charge electro-phoresis (ICEP), in which the polystyrene side moves forward. Mitochondria and lysosomes are trapped between the Au surface and the ITO substrate. In the higher frequency regime (20 k-5 MHz), the 10 μm JP's propulsive mechanism is self-dielectrophoresis (sDEP). All of the three organelles could be trapped at the different locations of the DEP traps on the surface of the JP as shown in FIG. 21D. Such variation of trapping modes allows realization of two different strategies of organelle manipulation and transport: 1) Organelle-specific manipulation: for example, at frequencies higher than 500 kHz and with 10 μm JPs, only nuclei are trapped at position 1 (FIG. 21C), while at frequencies between 100-500 kHz and 10 μm JPs, only mitochondria are trapped at position 2. 2) Multiple type organelle manipulation: for example, at frequencies between 100-500 kHz, mitochondria are trapped at position 2, while nuclei are simultaneously trapped at position 1.

Nucleus Manipulation. Transport and Electro-Deformation

When targeting the nucleus, it was found that the JP manipulates and transports nuclei in two different modes: 1) push mode (FIG. 22A), in which the JP pushes the nucleus that is located in front of it. This mode is predominant at relatively low frequencies (10-50 kHz for solution conductivity of 26 μS/cm, and 50-70 kHz for solution conductivity of 6 μS/cm) and the 2) carry-on-top mode (FIG. 22B), in which the JP carries the nucleus on its top, as seen at relatively high frequencies (100 kHz-1 MHz for solution conductivity of 26 μS/cm, and 80 kHz-1 MHz for solution conductivity of 6 μS/cm. The DEP response was examined using a quadrupolar array of the electrodes and was shown to exhibit a pDEP response throughout the examined frequency range (depicted in FIG. 22C in terms of the measured translational DEP velocity which corresponds to the Clausius-Mossotti factor) for both tested solution conductivities. The propulsion velocities with/without the loaded nucleus reversed from induced-charge electro-phoretic (ICEP) to self-dielectrophoretic (sDEP) propulsion mode at a critical frequency (30-40 kHz for 6 μS/cm and 60-70 kHz for 26 μS/cm) without cargo loading (FIG. 22D).

Figures 22A, 22B, 22C:
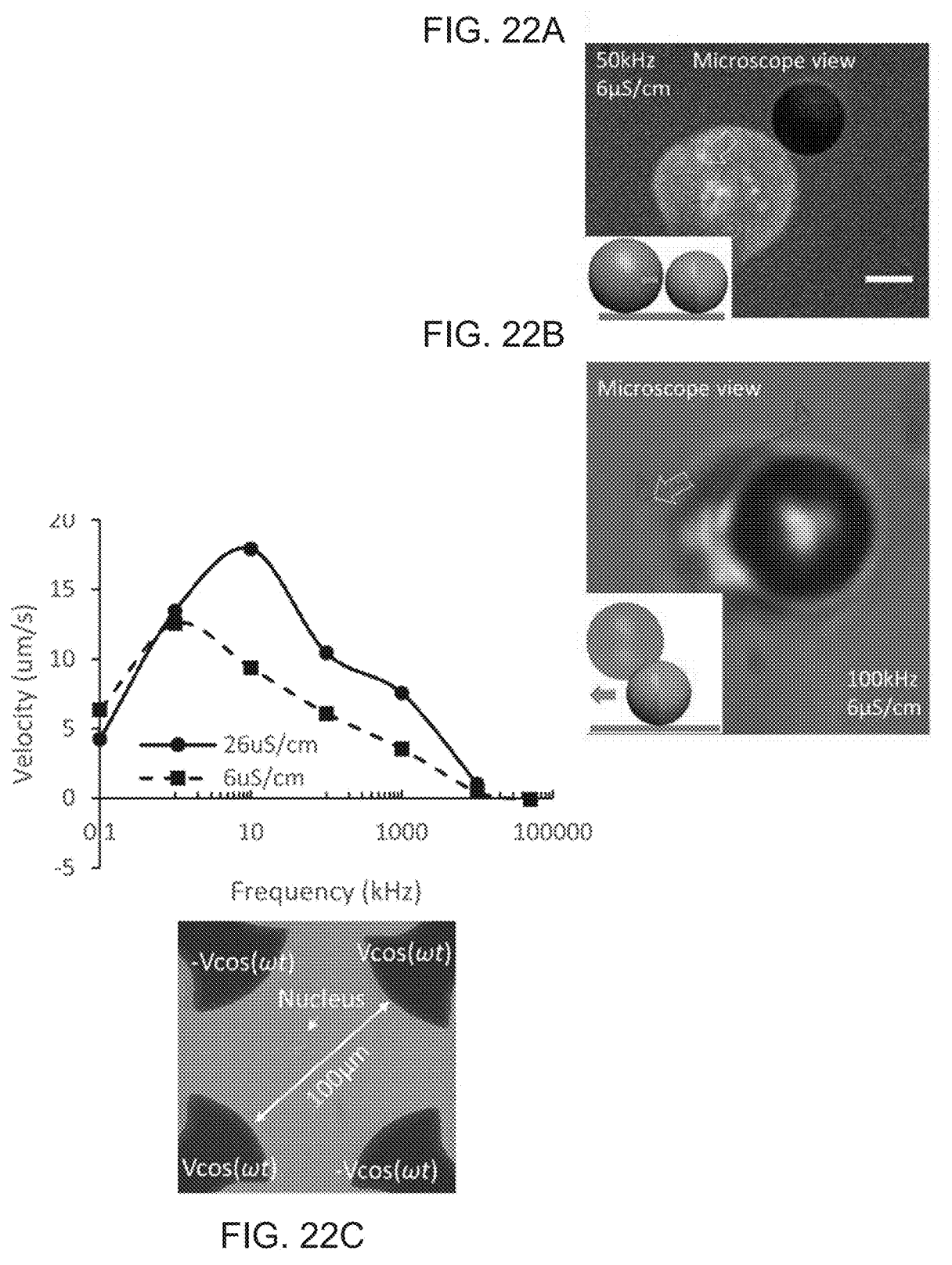
Figure 22D:
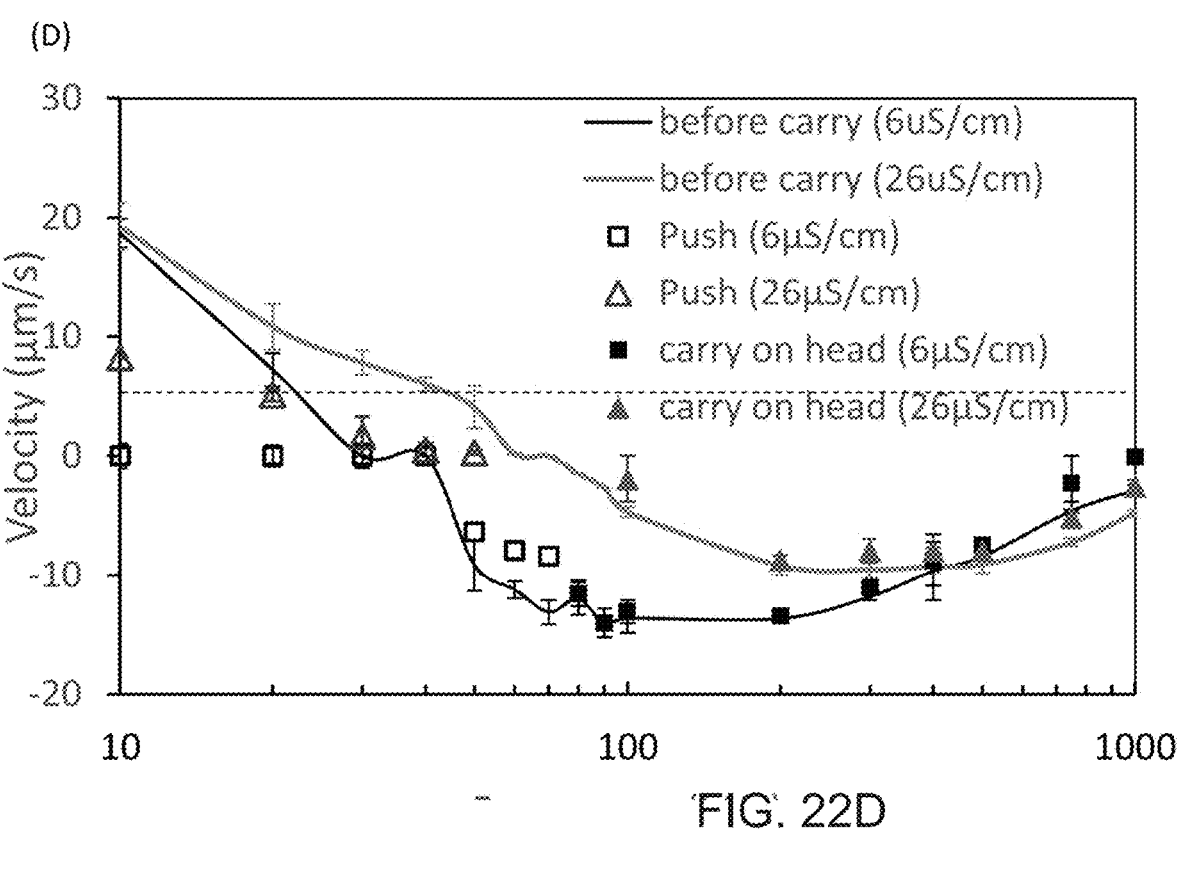

As shown in FIG. 22D, the different cargo manipulation modes (push, carry-on-top) affected the velocity of the JP. Its velocity, relative to the case without cargo, decreased more significantly in the push mode relative to the carry-on-top mode, which might be explained by increased interaction with the substrate in the former case.

The transition at about 70-80 kHz from the push to the carry on-top mode in the low conductivity solution (6 μS/cm) seems to be related to the increasing propulsion velocity which pushes the nucleus to its top part where it is dielectorphoretically trapped at location 1 in FIG. 21C. Under the ICEP mode (i.e., when the JP moves with its dielectric hemisphere forward) the JP could not push the nucleus until ~50 kHz. In contrast, in the higher conductivity solution (26 μS/cm), the JP was able to push the nucleus in both ICEP and sDEP modes. The former seems to also involve trapping of the nucleus at location 3 (FIG. 21C) due to strong pDEP forces in correspondence with the higher DEP response of the nucleus (FIG. 22C) at these lower frequencies (10-30 kHz). After exceeding the critical frequency for the reversal of the propulsion velocity, the nucleus is carried on-top of the JP to the trapping location 1.

Figure 22E:
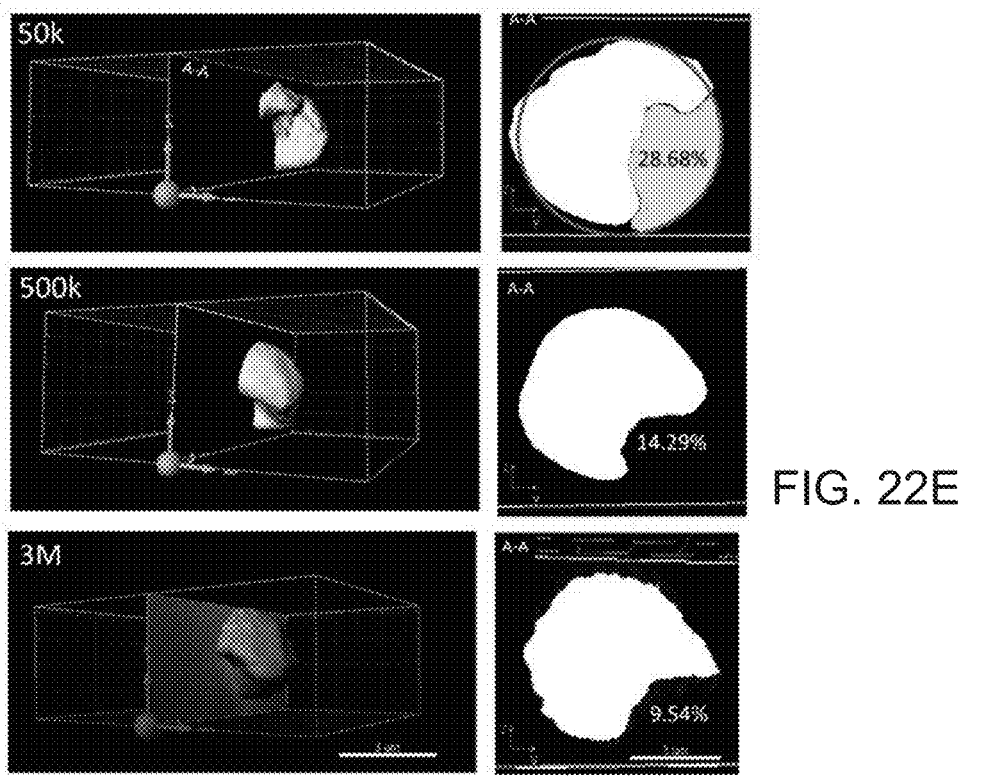

The on-top trapping of nuclei, specifically at location 1, was further verified in the 3D z-scan confocal images, where their cross-sections along the symmetric plane (A-A) are shown in FIG. 22E. The void region of the cross-section was due to the presence of the JP and is located more on the metallic side of the JP. The void region became smaller with increasing frequency, which is in agreement with the decreasing DEP force acting on the nucleus (FIG. 22C).

Electro-Deformation of MDA-MB-231 and MCF7 Nucleus

Figures 23A, 23B, 23C, 23D, 23E, 23F, 23G, 23H, 23I:
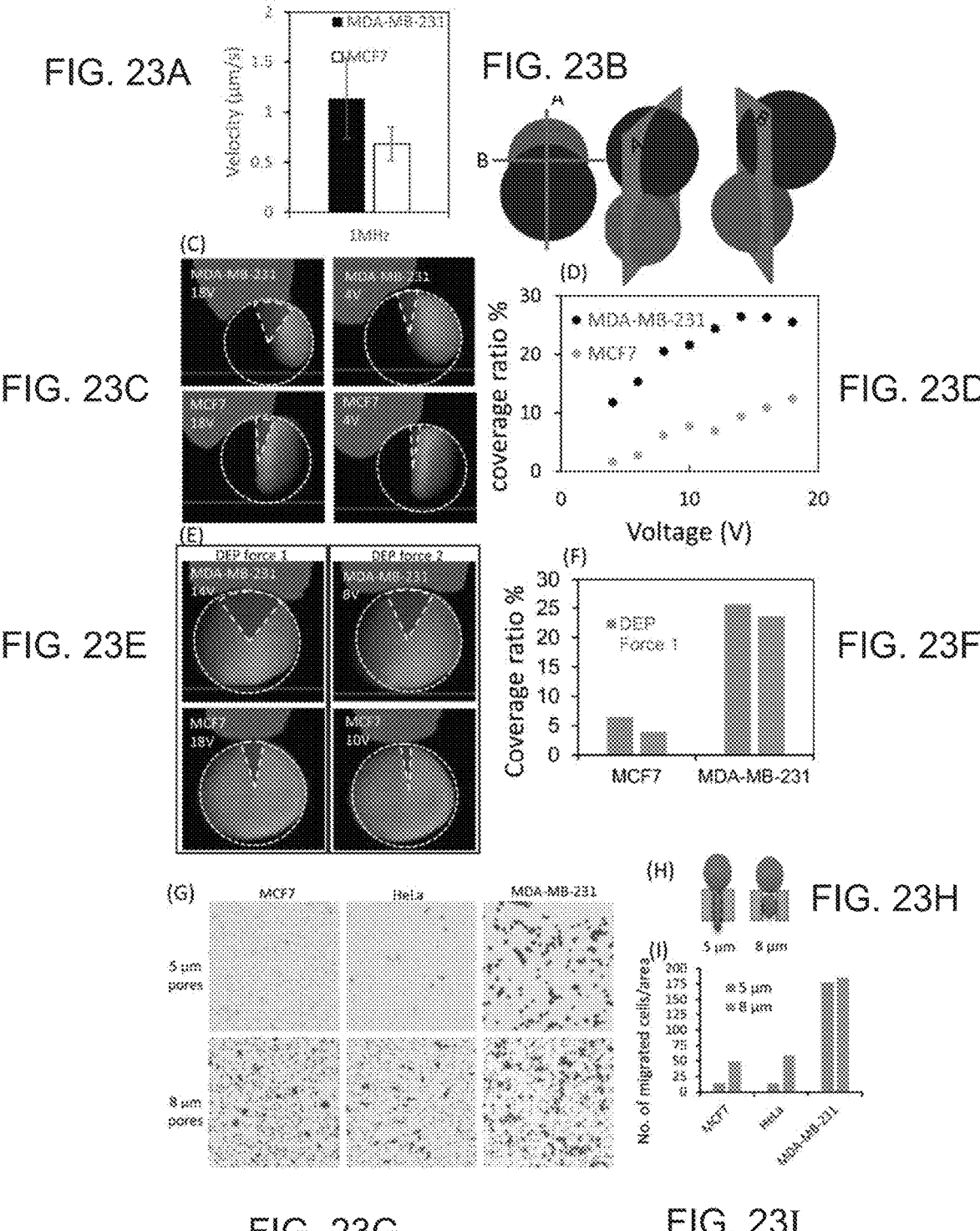
FIGS. 23A-I show deformability analysis of MDA-MB-231 and MCF7 nucleus using a Janus particle. (A) DEP response (i.e. velocity; positive towards the electrode edge) of the nuclei within a quadrupolar electrode array. DEP response was estimated by measuring the average transla- tional velocities between 10 and 20 μm distance from the edge of the electrode. (B) Schematic illustration of the two cutting planes (A and B): top view and perspective views of A and B, respectively. (C) The nucleus and JP rebuilt from Imaris 5.0 at plane A. The red area represents the nucleus, and the green represents the polystyrene hemisphere of the JP. The whole JP is indicated using a dotted yellow circle. The shaded circular sector represents the section of the JP's polystyrene hemisphere that is covered by the nucleus. (D) The coverage ratio (sector angle divided by π) of each nucleus at 1 MHz for various voltages. (E) The nucleus and JP rebuilt from Imaris 5.0 at plane B. (F) the coverage ratio (sector angle divided by 2π) of each nucleus at 1 MHz for varying voltage. (G) Microscope images of the different cells that were able to transmigrate the array of pores. (H) Schematic illustration of the cell deformation during the transmigration process. (I) The number of transmigrated cells per interrogation area.

DEP responses of each of the nucleus was estimated by measuring average translational velocities within a distance 10 to 20 μm from the edge of the electrode. FIG. 23A shows that at 1 MHz the velocity of MDA-MB-231 is 1.6 times higher than MCF7. Hence, in order to achieve the same DEP force, MCF7 requires 1.26 ($\sqrt{1.6}$; due to the quadratic dependency of the DEP force, i.e. induced Maxwell stresses, on the applied voltage) times higher voltage than MDA-MB-231.

When DEP force is higher, the nucleus is able to overcome the nDEP force at the polystyrene side and cover certain portion of polystyrene. However, when DEP force is lower, due to the gravity, nucleus tend to falling down along the metallic side of the JP. FIG. 23C shows the nucleus and JP rebuilt from Imaris 5.0 at plane A (FIG. 23B). The red color represents the nucleus, and the green color represents the JP's polystyrene hemisphere. The coverage ratio, defined by dividing the sector angle of the polystyrene part covered by the nucleus by n. By comparing the coverage ratio of two different nuclei (FIGS. 23C and 23D), it was found that MDA-MB-231 showed a higher coverage ratio than MCF7, which implies that MDA-MB-231 is significantly more deformed.

Since the MDA-MB-231 experiences a higher DEP force than that applied on the MCF7 under the same applied voltage at a frequency of 1 MHz (FIG. 23A) their electro-deformation was compared also under the same applied DEP by tuning the applied voltage accordingly (FIGS. 23E and 23F). It is clearly shown that under the same applied DEP force the MDA-MB-231 is significantly more deformed than the MCF7. This is again quantified by the coverage ratio (for plane B it is defined as the sector angle divided by $2\pi$) observed in a section plane B. The result that MDA-MB-231 has a larger deformability than MCF7 as obtained from the micromotor-based electro-deformation test, were further validated with a standard transmigration assay in Transwell inserts with two different pore size, 5 μm and 8 μm (FIG. 23G). The diameters of nuclei are around 8-10 μm, which restrict the transmigration of whole cell Therefore, when a serum chemotaxis was applied in a lower chamber, the nucleus transmigration from the top to the bottom chambers is in direct correlation to its deformability (FIG. 23H). Only about 50 MCF7 cells per interrogation area transmigrated through the 8 μm pores, while very few MCF7 cells were able to pass through 5 μm pores. In contrast, the MDA-MB-231 cells displayed strong deformability and more than 180 cells per interrogation area transmigrated successfully in both 5 μm and 8 μm pores, without significant difference between two pore sizes. Therefore, the nuclei of MDA-MB-231 cells has a much stronger deformability than MCF7 cells, which is consistent with their stronger metastasis ability in vivo.

Mitochondrion Manipulation and Transport

When targeting the mitochondrion, it becomes trapped between the JP's metallic hemisphere and the ITO substrate at two distinct frequency regimes: 1) a low-frequency regime (0.05-0.5 kHz) (FIGS. 24A and 24C), wherein the JP moves with its dielectric hemisphere forward and a 2) high-frequency regime (100-500 kHz) (FIGS. 23B and 23D) wherein the JP moves with its metallic hemisphere forward. In the low-frequency regime, the number of mitochondria trapped is determined by both the DEP response and the induced-charge electro-osmotic (ICEO) flow around the JP. The latter injects mitochondria into the trapping area and hence, with increasing flow, there is a parallel increase in the number of trapped mitochondria. However, if the ICEO flow is too large, the hydrodynamic shearing may result in fewer trapped mitochondria, as probably is the case with 0.2 kHz when compared to 0.1 kHz in FIG. 24C. Due to both the relatively large number of trapped mitochondria and the exchange of some with newly ICEO injected mitochondria with older ones that are hydrodynamically sheared, the number of trapped mitochondria was characterized using the mean fluorescence intensity of the area of interest (yellow circle in FIG. 24A) after 1.5 minutes of trapping. A low voltage of 1.5V was used to trap the mitochondria, since at higher voltages, the ICEO flow shears away the trapped mitochondria.

Figure 24D:
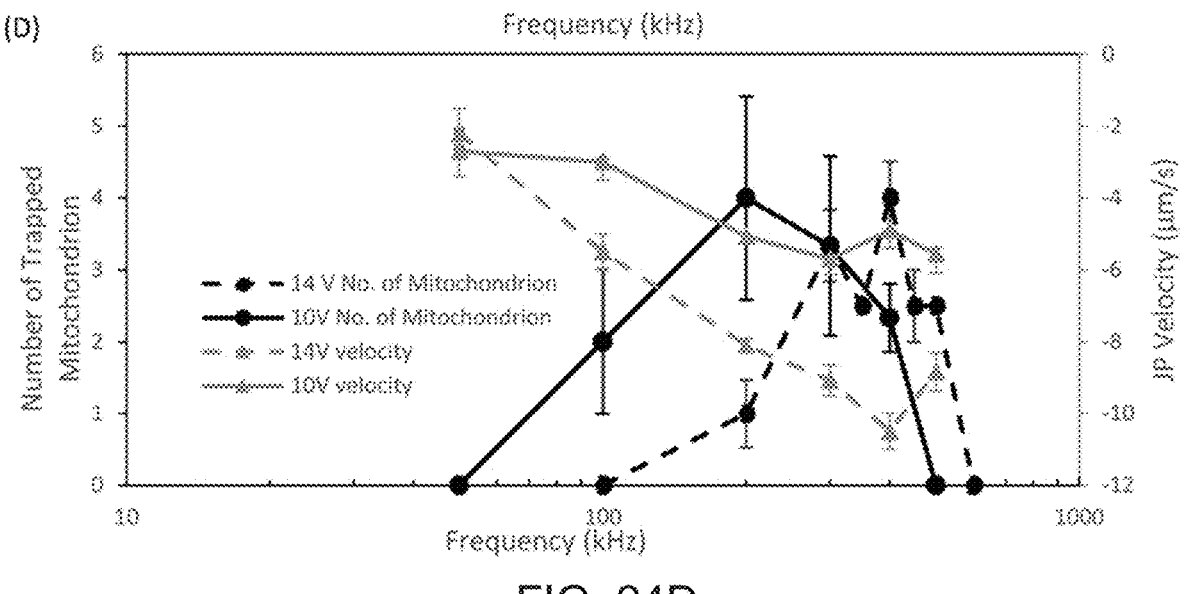

In the high-frequency regime (FIGS. 24B and 24D), the number of trapped mitochondria is determined by both the DEP response and the velocity of the JP. The trapping ability of the JP is characterized by the maximum number of individual mitochondria observed after 3.5 minute of trapping. The number of trapped mitochondria drastically increased from 0 (50 kHz) to 4±1.4 (200 kHz) at 10V (FIG. 24D). However, the quad test showed that the pDEP force for mitochondria was higher at 50 kHz than 200 kHz. Hence, the decreased trapping at a low frequency may be due to the higher ICEO flow around a JP at lower (50 kHz) as compared to higher (200 kHz) frequency. When increasing the voltage at the same frequency, the number of trapped mitochondria seemed to decrease (e.g., at 200 kHz from 4±1.4 to 1±0.47), likely due to the higher velocity of the JP at 14V (8.1±0.2 μm/s) as compared to 10V (5.07±0.03 μm/s), which caused enhanced hydrodynamic shearing of the mitochondria. No significant trapping of mitochondria was observed in the higher conductivity solution of 26 μS/cm.

Lysosome Manipulation and Transport

Figures 25A, 25B:
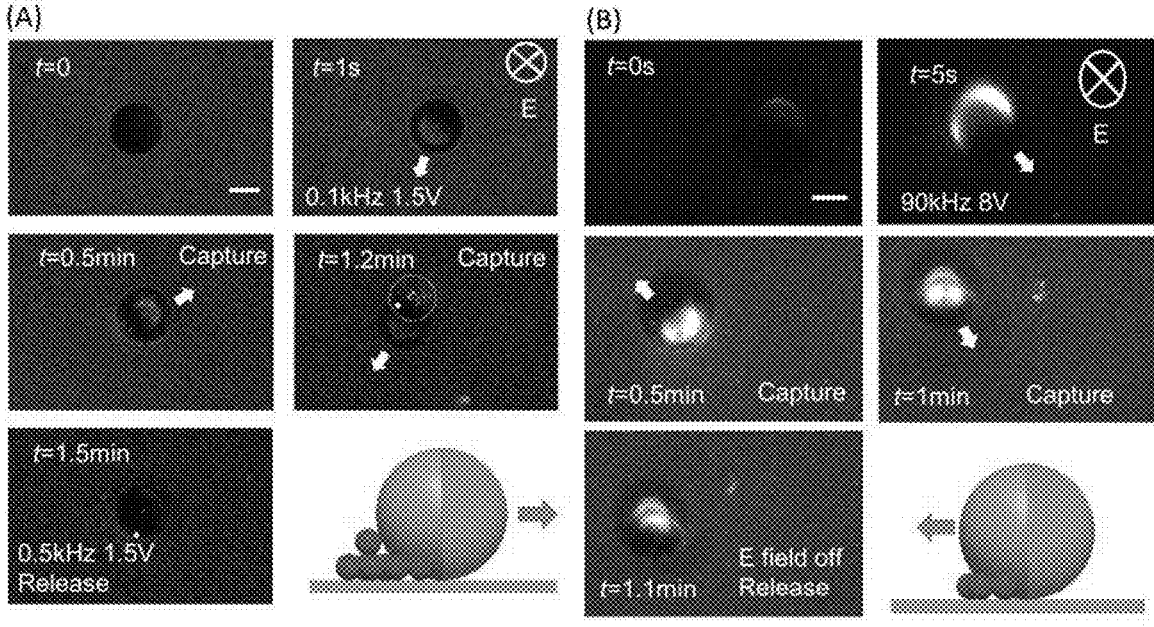
FIGS. 25A-D show trapping and transport of lysosomes using a Janus particle. The lysosome is always trapped between the metallic hemisphere of the Janus particle (JP) and the ITO substrate. (A) Sequential trapping of a lysosome using a JP of 10 μm in diameter, at 0.1 kHz and 1.5V, with solution conductivity of 6 μS/cm. (B) Sequential trapping of a lysosome using a JP of 15 μm in diameter, at 90 kHz and 8V, with solution conductivity of 6 μS/cm. (C) Mean fluo- rescence intensity in the trapping area on the metallic side of the JP at a frequency range between 0.01 kHz-1 kHz. The velocity of the JP is plotted on the secondary axis. Insert: mean fluorescence intensity in the area of interest, for frequency (0.05 kHz, 0.1 kHz and 0.2 kHz) versus operation time. (D) Number of individually trapped lysosomes over the frequency range of 10 kHz-150 kHz. The velocity of the JP is plotted on the secondary axis.
Figures 25C, 25D:
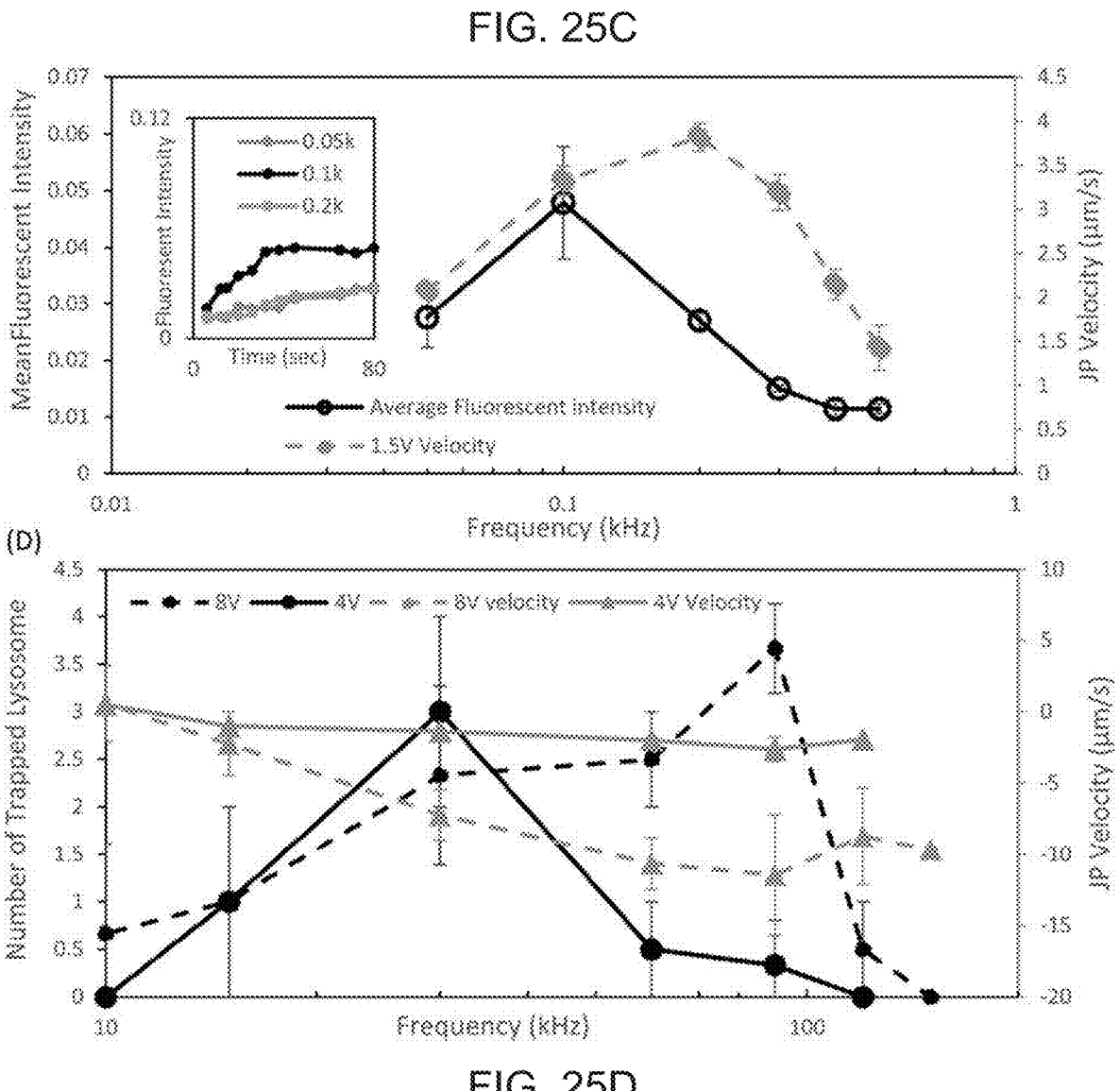

Characterization of lysosome trapping showed that, as with the mitochondrion, the lysosome is trapped between the JP's metallic hemisphere and the ITO substrate at two distinct frequency regimes: 1) low-frequency regime (0.05 kHz-0.5 kHz), wherein the JP moves with its dielectric end forward (FIGS. 25A and 25C) and 2) high-frequency regime (30 kHz-120 kHz), wherein the JP moves with its metallic end forward (FIGS. 25B and 25D).

In the low-frequency regime (FIGS. 25A and 25C), the number of trapped lysosomes is determined by both the DEP response and the ICEO flow around the JP. In the high-frequency regime, no significant lysosomal trapping was observed using a JP of 10 μm in diameter. However, for a 15 μm-diameter JP, significant trapping was observed (FIGS. 25B and 25D). This enhanced trapping with increasing JP diameter is in agreement with the larger area below the JP, where sufficiently high electric field gradients, necessary for trapping, exist. The reason lysosomes are more challenging to trap is likely due to their smaller size, hence, requiring higher pDEP force for trapping. In the high-frequency regime (FIGS. 25B and 25D), the number of lysosomes trapped by the JP is also determined by both the lysosome DEP response and the velocity of the JP. The JP trapping ability is characterized by the number of individually trapped lysosomes after 1 minute of trapping. While the velocity of the JP between 90 kHz-120 kHz did not change significantly, the number of trapped lysosomes drastically decreased from 3.67±0.47 (90 kHz) to 0.5±0.3 (120 kHz) at an applied voltage of 8V.

Simultaneous Trapping of Different Organelles

Figure 26C:
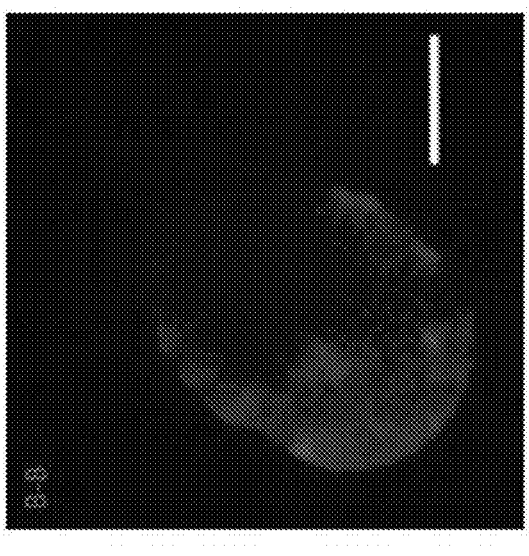
FIGS. 26A-C show simultaneous trapping of mitochon- dria and nuclei at different locations along the Janus particle surface. Mitochondria are stained with red fluorescent dye and the nucleus is stained with blue fluorescent dye. Solution conductivity of 6 μS/cm, applied field of 100 kHz, 10V.
Figure 26B:
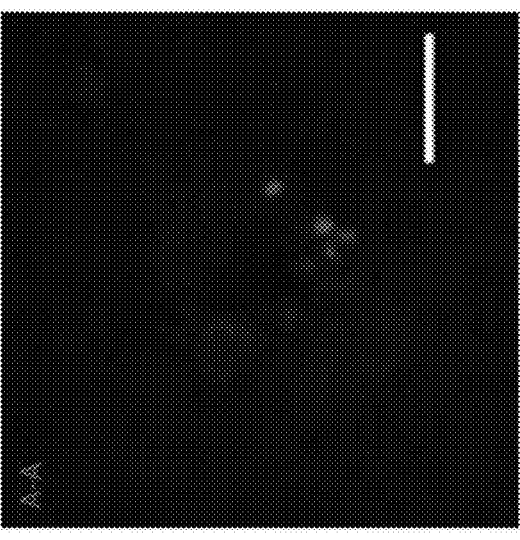
Figure 26A:
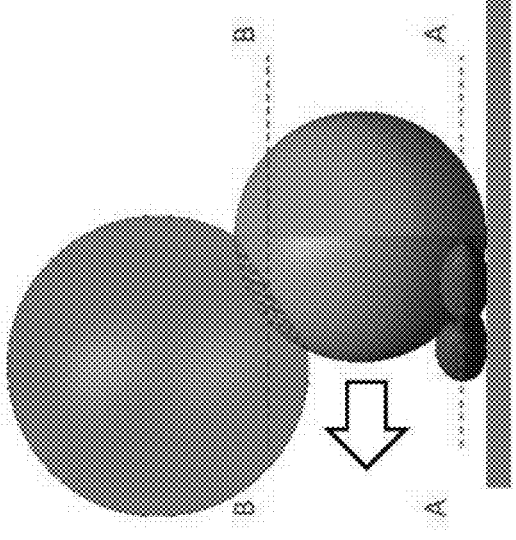
Figure 27:
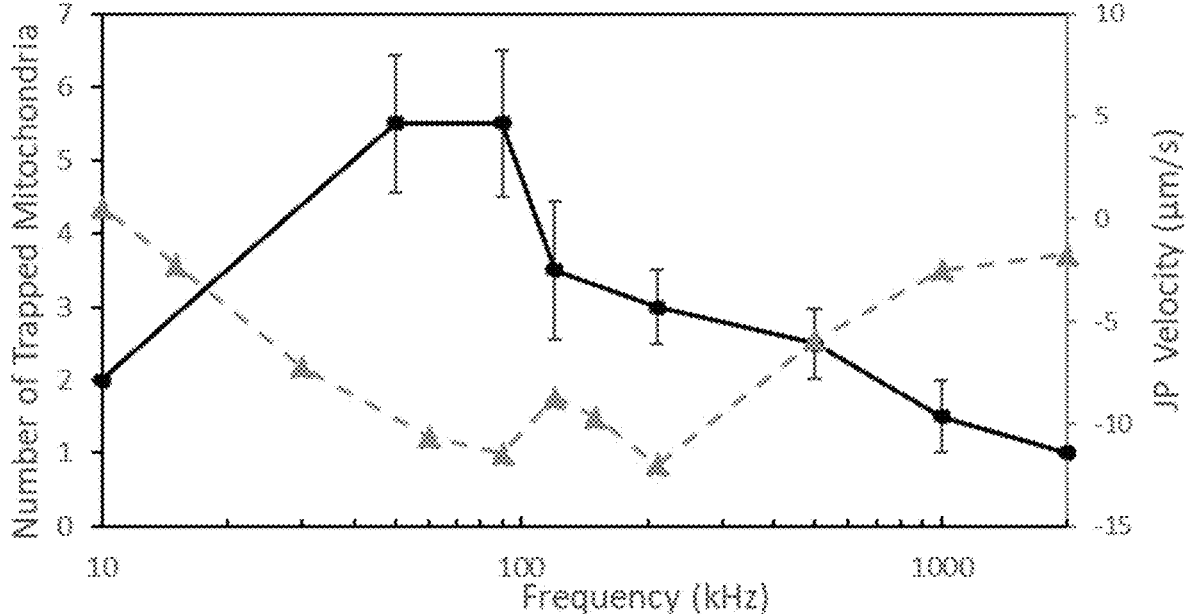
FIG. 27 shows the number of individually trapped mito- chondria (solid line, left vertical axis) by JP with a diameter of 15 μm. The velocity of the JP is also plotted (dashed line, right vertical axis). Data are shown for low-conductivity (6 μS/cm) solution.

Simultaneous trapping of mitochondria and nuclei was possible at 100 kHz and 10V, using a 10 μm JP, wherein the nucleus was trapped at the top of the particle, while mitochondria were trapped between the metallic surface and the ITO substrate (FIGS. 26A-C). This observation demonstrated that the active particle can both trap single organelle types by tuning the frequency (FIG. 21D) and also maintain them spatially separated on the JP surface. Simultaneous trapping of lysosomes and nuclei was not possible, as the lysosomes were only trapped by 15 μm-diameter JPs and at a maximum voltage of 8V, while nuclei were only trapped at voltages exceeding 10V. Simultaneous trapping of lysosomes and mitochondria occurred when using a 15 μm JP at 10 kHz-120 kHz and 8V. However, both were trapped between the metallic surface of the JP and the ITO substrate, with no spatial separation. Mitochondria trapping using 15 μm JPs at various frequencies and 8V, is shown in FIG. 27.

Conclusion

This Example demonstrated the use of an active particle system, acting as cargo carrier, to manipulate and transport different types of cell organelles (nucleus, mitochondria, and lysosome). Cargo manipulation (load and release) and carrier transport are singularly controlled using a single externally applied electric field via varying its frequency and amplitude. The cargo trapping onto the JP surface results from DEP forces. In contrast to the commonly used fixed electrode geometry for DEP manipulation, active particle of the present embodiments acts as a mobile microelectrode that can both manipulate (i.e., load and release) cargo using local DEP forces and transport cargo (through self-propulsion), with/without directed motion (magnetic steering). Besides avoiding the need to fabricate electrodes, the inherent nanometric gap formed between the particle and the ITO-coated glass substrate circumvents the need for complicated nanofabrication techniques, ensuring nanometric gaps between electrodes when dielectrophoretically trapping nanoscale particle/biomolecules. This approach is particularly advantageous for trapping small organelles such as lysosomes. In addition, the closed microchamber environment and directed motion option allows for superb subcellular accuracy, precluding the need for invasive external manipulation of the electrode position.

The ability to release cargo by simply tuning the frequency or turning off the electric field is a significant advantage of the DEP-based trapping mechanism. In contrast, micromotors that load cargos by magnetic, electrostatic, or biomolecular attraction forces might not be able to easily (if at all) release cargo. Specifically, lowering the frequency results in an increased ICEO flow which may hydrodynamically shear the trapped organelles, e.g. nucleus is released upon changing the frequency from about 200 kHz to about 10 kHz while mitochondrion and lysosomes are released upon changing the frequency from 0.1-0.5 kHz to 1 kHz. Another strategy for releasing the trapped organelles can be achieved when increasing the frequency beyond the COF from a pDEP to nDEP behavior (see FIG. 21D). Furthermore, turning off the electric field is also an option for releasing all trapped organelles.

Figure 28:
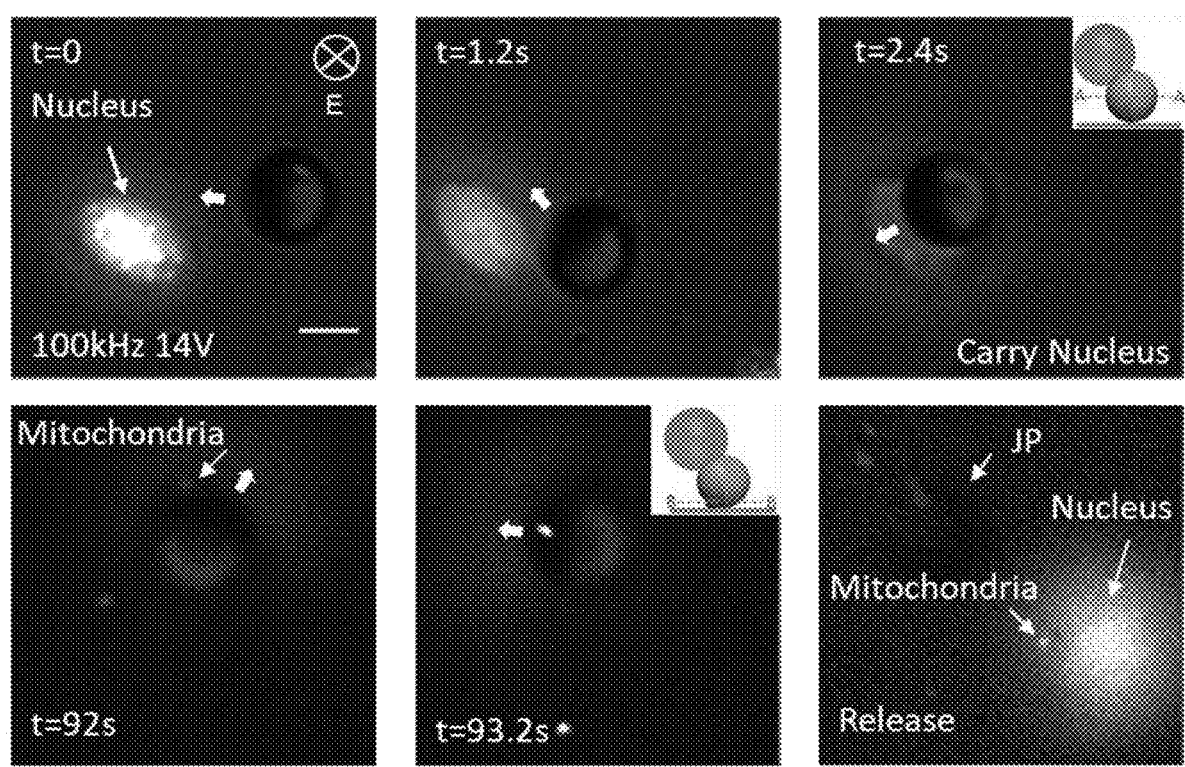
FIG. 28 shows sequential simultaneous trapping of a non-fixed nucleus and mitochondrion by a JP, in low- conductivity medium (9 μS/cm).
Figure 29:
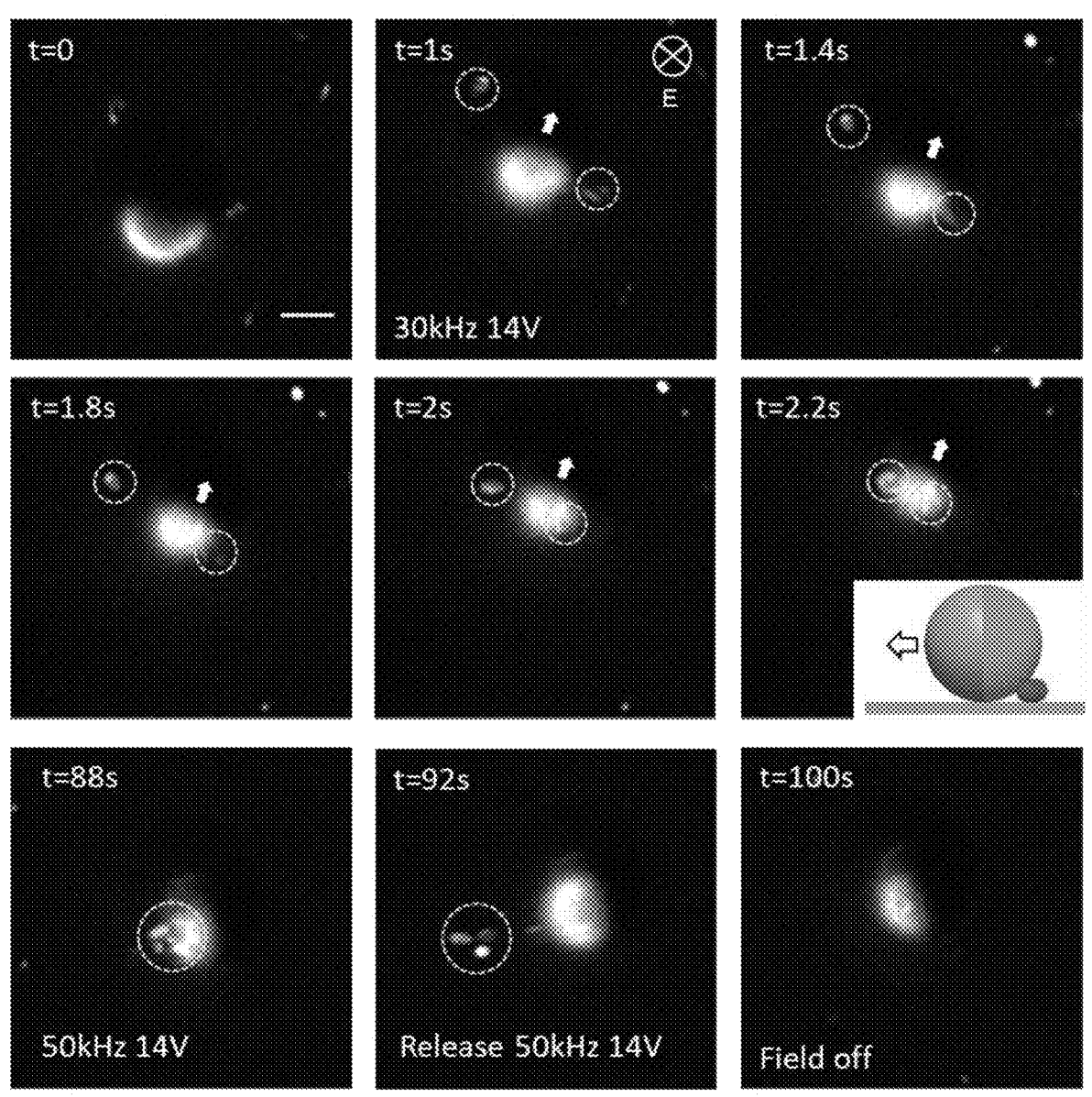
FIG. 29 shows trapping of a non-fixed lysosome at the JP's polystyrene hemisphere, by a 15 μm JP, in low-con- ductivity medium (9 μS/cm). 1-2.2 s: trapping of two mitochondria (yellow circles) by the JP. Trapping location is illustrated in the inset. 88-92 s: release a group of mitochon- dria by increasing the frequency from 30 kHz to 50 kHz.

Trapping different cargos (organelles) at different locations of the JP is a unique feature of the proposed active particle system. Micromotors, which rely on electrostatic interaction, physical absorption or surface functionalization to trap drugs/cargos, can only uniformly load cargo. However, in the active particle system, electric field gradients with positive and negative DEP potential wells are created at different locations on the symmetry-broken JP (FIG. 21C). Since both DEP force and self-propulsion strongly depend on the applied electric field frequency, this competition enables selective trapping of different organelles. Due to the larger size of the nucleus, it is trapped on top of the JP between 80-1 MHz (10V). Mitochondria are trapped between the JP's (10 μm in diameter) metallic hemisphere and the ITO substrate at either low (0.05-0.5 kHz) or high-frequency (100-500 kHz) regimes (FIGS. 24A-D). In the high-frequency regime, lysosomes can only be trapped by JPs with a sufficiently large diameter, e.g., 15 μm at 10-120 kHz (FIGS. 25A-D). This result enables separation, isolation and pre-concentration of cell organelles. The targeted organelles studied here were fixed with 4% v/v paraformaldehyde, so that trapping and manipulation could be performed in low-conductivity (<0.035/m) environments. However, exchanging the high ionic conductivity physiological solution with solution of low ionic conductivity but of similar osmolality is feasible. Such low-conductivity buffer is commonly used in DEP manipulation of mitochondria. Trapping of a non-fixed nucleus and mitochondrion in low-conductivity buffer (9 μS/cm) showed behavior similar to that of the fixed samples (see FIG. 28). However, the non-fixed lysosomes are trapped at the polystyrene side of the 15 μm JP in the low-conductivity buffer (see FIG. 29) at 30 kHz and 14V, suggesting that the DEP characteristics of the lysosomes were changed before (nDEP) and after (pDEP) fixation.

The specific fluorescent dyes of the targeted cell organelles not only provided loading guidance, but also revealed physiological properties of these organelles. The mitochondria were stained with MitoTracker Red (suitable for mitochondrial fixation) and MitoTracker Green (for non-fixed mitochondria) (Thermofisher), which are membrane potential dye. These two dyes stain healthy metabolically active mitochondria. During loading and release process, no significant reduction of fluorescent signal was observed, which suggested the mitochondrial membrane potential was still retained and therefore mitochondria were intact and functional. Lysosomes were stained with LysoTracker Red DND-99 (Thermofisher), which is a marker for acidic cell organelles, such as lysosomes. No significant fluorescent signal reduction of the lysosomes was observed during loading and transportation process, which indicates the lysosome still maintained its acidification and function. DAPI was used to stain nucleus and also for assessing the nuclear morphology, which can reflect the cell apoptosis (with chromatin condensation and nuclear deformation), necrosis (with nucleus fading and dispersal) and mitosis (with chromosome condensation and segregation). During loading and release process, no cell apoptosis and necrosis was observes, demonstrating that this strategy was not destructive to the cell nucleus as well.

The elastic/deformation properties of the nucleus have been intensively studied in stomach cells and human embryonic stem cells using a micropipette aspiration system. This Example demonstrates how the JP can act as a mobile platform for mechanical probing of a single nucleus. The electro-deformation of the nucleus, resulting from the induced Maxwell stresses, can be tuned using either the electric field frequency (FIG. 22E) or voltage (FIG. 23D). The coverage ratio of the JP's polystyrene hemisphere in contact with the deformed nucleus has been shown to be in agreement with the nucleus deformability. Specifically, it was shown that MDA-MB-231 has higher coverage ratio compared with MCF7 under the same DEP force, which implies higher deformability of MDA-MB-231. This result is in line with the standard Transwell result in FIGS. 23G and 231. This coverage ratio must depend on the mechanical properties of nucleus and hence can act as a promising biomechanical marker. This result can potentially serve as a novel tool to determine the elastic properties of a single and targeted nucleus.

In the system presented in this Example, mitochondria and lysosomes are immobilized between the metallic hemisphere of JP and ITO substrate. This immobilization provides a novel and easier means of directly imaging organelles at a single-cell level, as compared to nanofluidic platforms and nanohole array. The active loading can be used for selective purification of targeted organelles of interest from a mixed biological sample. For example, isolation of a single neuron cell nucleus from fresh brain tissue is usually complicated and challenging. Organelles of interest can be pre-stained with immunofluorescence or prelabelled with specific fluorescence tag, which provide guidance for active and selective loading of organelles or other subcellular components. Meanwhile, the ability to release cargo provides a technique to harvest targeted organelles. These isolated organelles can be applied for gene/RNA sequencing or proteomics analysis. The trapping and transport of organelles on the particle can also be used for analyzing the elastic properties of a single nucleus, for inducing cell fusion, cell fission, for dysfunction of mitochondrion, and/or autophagosome-lysosome fusion.

REFERENCES FOR EXAMPLE 3

1. C.-C. Chang et al., Mechanical property characterization of hundreds of single nuclei based on microfluidic constriction channel. Cytom. Part A. 93, 822-828 (2018).
2. K. S. Dimmer, L. Scorrano, (De)constructing Mitochondria: What For?Physiology. 21, 233-241 (2006).
3. C. Tesauro et al., Isolation of functional mitochondria by inertial microfluidics—a new method to sort intracellular organelles from a small scale biological sample. RSC Adv. 7, 23735-23741 (2017).
4. C. Aguado, E. Pérez-Jiménez, M. Lahuerta, E. Knecht, (Humana Press, New York, NY, 2016, pp. 299-311.
5. C. Frezza, S. Cipolat, L. Scorrano, Organelle isolation: functional mitochondria from mouse liver, muscle and cultured filroblasts. Nat. Protoc. 2, 287-295 (2007).
6. R. Flükiger-Gagescu, J. Gruenberg, Immunoisolation of Organelles Using Magnetic Solid Supports. Cell Biol., 27-31 (2006).
7. C. Pasquali, I. Fialka, L. A. Huber, Subcellular fractionation, electromigration analysis and mapping of organelles. J. Chromatogr. B Biomed. Sci. Appl. 722, 89-102 (1999).
8. Z. Li et al., Alignment and counting of mitochondria based on capillary electrophoresis. Sensors Actuators B Chem. 265, 110-114 (2018).
9. M. Moschallski et al., MicroPrep: Chip-based dielectrophoretic purification of mitochondria. Electrophoresis. 31, 2655-2663 (2010).
10. J. Luo, B. G. Abdallah, G. G. Wolken, E. A. Arriaga, A. Ros, Insulator-based dielectrophoresis of mitochondria. Biomicrofluidics. 8, 021801 (2014).
11. C.-H. Tai, S.-K. Hsiung, C.-Y. Chen, M.-L. Tsai, G.-B. Lee, Automatic microfluidic platform for cell separation and nucleus collection. Biomed. Microdevices. 9, 533-543 (2007).
12. K. Norregaard, R. Metzler, C. M. Ritter, K. Berg-Sørensen, L. B. Oddershede, Manipulation and Motion of Organelles and Single Molecules in Living Cells. Chem. Rev. 117, 4342-4375 (2017).
13. S. Kumar, G. G. Wolken, N. J. Wittenberg, E. A. Arriaga, S.-H. Oh, Nanohole Array-Directed Trapping of Mammalian Mitochondria Enabling Single Organelle Analysis. Anal. Chem. 87, 11973-11977 (2015).
14. K. Zand, T. Pham, A. Davila, D. C. Wallace, P. J. Burke, Nanofluidic Platform for Single Mitochondria Analysis Using Fluorescence Microscopy. Anal. Chem. 85, 6018-6025 (2013).
15. S. Ghosh, A. Ghosh, Mobile nanotweezers for active colloidal manipulation. Sci. Robot. 3 (2018), doi:10.1126/scirobotics.aaq0076.
16. F. Qiu et al., Magnetic Helical Microswimmers Functionalized with Lipoplexes for Targeted Gene Delivery. Adv. Funct. Mater. 25, 1666-1671 (2015).
17. D. M. Graham, M. A. Messerli, R. Pethig, Spatial manipulation of cells and organelles using single electrode dielectrophoresis. Biotechniques. 52, 39-43 (2012).
18. S.-H. Huang, L.-Y. Hung, G.-B. Lee, Continuous nucleus extraction by optically-induced cell lysis on a batch-type microfluidic platform. Lab Chip. 16, 1447-1456 (2016).
19. B. P. Nadappuram et al., Nanoscale tweezers for single-cell biopsies. Nat. Nanotechnol. 14, 80-88 (2019).
20. A. Ashkin, K. Schutze, J. M. Dziedzic, U. Euteneuer, M. Schliwa, Force generation of organelle transport measured in vivo by an infrared laser trap. Nature. 348, 346-348 (1990).
21. V. S. Vajala et al., Optical microwell array for large scale studies of single mitochondria metabolic responses. Anal. Bioanal. Chem. 406, 931-941 (2014).
22. H. R. Jiang, N. Yoshinaga, M. Sano, Active motion of a Janus particle by self-thermophoresis in a defocused laser beam. Phys. Rev. Lett. 105 (2010), doi:10.1103/PhysRevLett.105.268302.
23. Y. Wu, T. Si, J. Shao, Z. Wu, Q. He, Near-infrared light-driven Janus capsule motors: Fabrication, propulsion, and simulation. Nano Res. 9, 3747-3756 (2016).
24. F. Zhang et al., A Macrophage-Magnesium Hybrid Biomotor: Fabrication and Characterization. Adv. Mater. 31, 1901828 (2019).

25. T. Mirkovic, N. S. Zacharia, G. D. Scholes, G. A. Ozin, Nanolocomotion-Catalytic Nanomotors and Nanorotors. Small. 6, 159-167 (2010).

26. A. Boymelgreen, G. Yossifon, Observing Electrokinetic Janus Particle-Channel Wall Interaction Using Micropartticle Image Velocimetry. Langmuir. 31, 8243-8250 (2015).

27. A. Boymelgreen, G. Yossifon, T. Miloh, Propulsion of Active Colloids by Self-Induced Field Gradients. Langmuir. 32, 9540-9547 (2016).

28. A. M. Boymelgreen, T. Balli, T. Miloh, G. Yossifon, Active colloids as mobile microelectrodes for unified label-free selective cargo transport. Nat. Commun. 9 (2018), doi:10.1038/s41467-018-03086-2.

29. R. Pethig, Review—Where Is Dielectrophoresis (DEP) Going? J. Electrochem. Soc. 164, B3049-B3055 (2017).

30. S. Sundararajan, P. E. Lammert, A. W. Zudans, V. H. Crespi, A. Sen, Catalytic Motors for Transport of Colloidal Cargo. Nano Lett. 8, 1271-1276 (2008).

31. J. Orozco et al., Dynamic Isolation and Unloading of Target Proteins by Aptamer-Modified Microtransporters. Anal. Chem. 83, 7962-7969 (2011).

32. G. Bai et al., Characterization of biomechanical properties of cells through dielectrophoresis-based cell stretching and actin cytoskeleton modeling. Biomed. Eng. Online. 16, 1-15 (2017).

33. 1. Guido, M. S. Jaeger, C. Duschl, Dielectrophoretic stretching of cells allows for characterization of their mechanical properties. Eur. Biophys. J. 40, 281-288 (2011).

34. V. C. Shukla et al., Lab-on-a-Chip Platforms for Biophysical Studies of Cancer with Single-Cell Resolution. Trends Biotechnol. 36 (2018), pp. 549-561.

35. J. Zemla et al., Atomic force microscopy as a tool for assessing the cellular elasticity and adhesiveness to identify cancer cells and tissues. Semin. Cell Dev. Biol. 73 (2018), pp. 115-124.

36. S. L. Leung, Y. Lu, D. Bluestein, M. J. Slepian, Dielectrophoresis-Mediated Electrodeformation as a Means of Determining Individual Platelet Stiffness. Ann. Biomed. Eng. 44, 903-913 (2016).

37. S. Gangwal, O. J. Cayre, M. Z. Bazant, O. D. Velev, Induced-Charge Electrophoresis of Metallodielectric Particles. Phys. Rev. Lett. 100, 058302 (2008).

38. T. M. Squires, M. Z. Bazant, Breaking symmetries in induced-charge electro-osmosis and electrophoresis. J. Fluid Mech. 560, 65 (2006).

39. A. Fu et al., High expression of MnSOD promotes survival of circulating breast cancer cells and increases their resistance to doxorubicin. Oncotarget. 7, 50239-50257 (2016).

40. M. Medina-Sánchez, H. Xu, O. G. Schmidt, Micro- and nano-motors: the new generation of drug carriers. Ther. Deliv. 9, 303-316 (2018).

41. S. V. Puttaswamy et al., Enhanced cell viability and cell adhesion using low conductivity medium for negative dielectrophoretic cell patterning. Biotechnol. J. 5, 1005-1015 (2010).

42. I. Samudio et al., 2-Cyano-3,12-dioxooleana-1,9-dien-28-imidazolide (CDDO-Im) directly targets mitochondrial glutathione to induce apoptosis in pancreatic cancer. J. Biol. Chem. 280, 36273-36282(2005).

43. A. Pol et al., A caveolin dominant negative mutant associates with lipid bodies and induces intracellular cholesterol imbalance. J. Cell Biol. 152, 1057-1070 (2001).

44. B. S. Cummings, R. G. Schnellmann, in Current Protocols in Pharmacology (John Wiley & Sons, Inc., 2004).

45. K. N. Dahl, A. J. Engler, J. D. Pajerowski, D. E. Discher, Power-Law Rheology of Isolated Nuclei with Deformation Mapping of Nuclear Substructures. Biophys. J. 89, 2855-2864 (2005).

46. J. D. Pajerowski, K. N. Dahl, F. L. Zhong, P. J. Sammak, D. E. Discher, Physical plasticity of the nucleus in stem cell differentiation. Proc. Natl. Acad. Sci. U.S.A 104, 15619-24(2007).

47. S. R. Krishnaswami et al., Using single nuclei for RNA-seq to capture the transcriptome of postmortem neurons. Nat. Protoc. 11, 499-524 (2016).

48. L. Aring, S. Steinbach, K. Marcus, C. May, in Methods in Molecular Biology (Humana Press Inc., 2018), vol. 1723, pp. 247-260.

49. R. V. Grindberg et al., RNA-sequencing from single nuclei. Proc. Natl. Acad. Sci. U.S.A 110, 19802-19807 (2013).

50. M. Gómez-Serrano, E. Camafeita, M. Loureiro, B. Peral, Mitoproteomics: Tackling mitochondrial dysfunction in human disease. Oxid. Med. Cell. Longev. 2018 (2018), doi:10.1155/2018/1435934.

51. A. Jourdain, J. C. Martinou, Mitochondrial dynamics: Quantifying mitochondrial fusion in vitro. BMC Biol. 8 (2010), doi:10.1186/1741-7007-8-99.

52. S. B. Moparthi, T. Wollert, Reconstruction of destruction—In vitro reconstitution methods in autophagy research. J. Cell Sci. 132 (2019), doi:10.1242/jcs.223792.

53. C.-Y. Wu, K. T. Roybal, E. M. Puchner, J. Onuffer, W. A. Lim, Remote control of therapeutic T cells through a small molecule-gated chimeric receptor. Science (80-.). 350, aab4077-aab4077 (2015).

54. C. H. Lin, Y. L. Chen, H. R. Jiang, Orientation-dependent induced-charge electrophoresis of magnetic metal-coated Janus particles with different coating thicknesses. RSC Adv. 7, 46118-46123 (2017).

55. S. Ma, A. Fu, S. Lim, G. G. Y. Chiew, K. Q. Luo, MnSOD mediates shear stress-promoted tumor cell migration and adhesion. Free Radic. Biol. Med. 129, 46-58 (2018).

Example 4

Trapping and Local Electroporation of Mammalian Cells

Experiments were conducted to demonstrate trapping and local electroporation of mammalian cells.

Figures 30A, 30B:
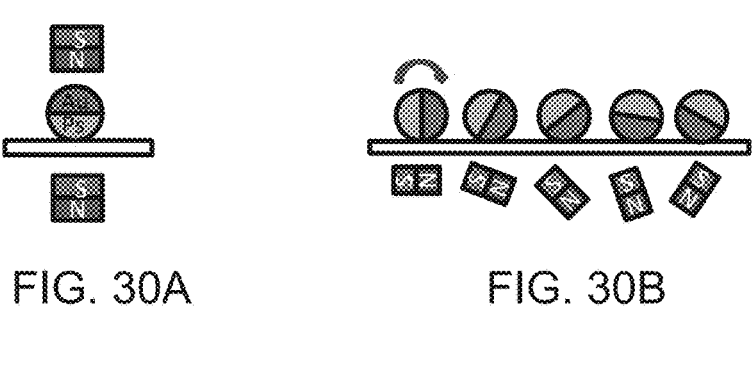
FIGS. 30A-I show methodology of experiments per- formed according to some embodiments of the present invention for trapping and local electroporation of mamma- lian cells.
Figure 30C:
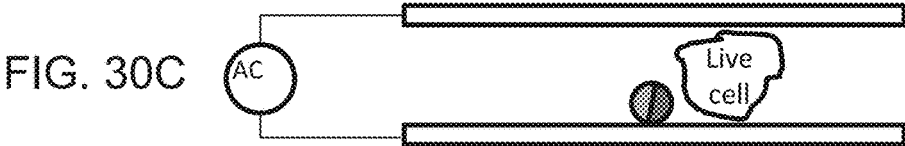
Figures 30D, 30E:
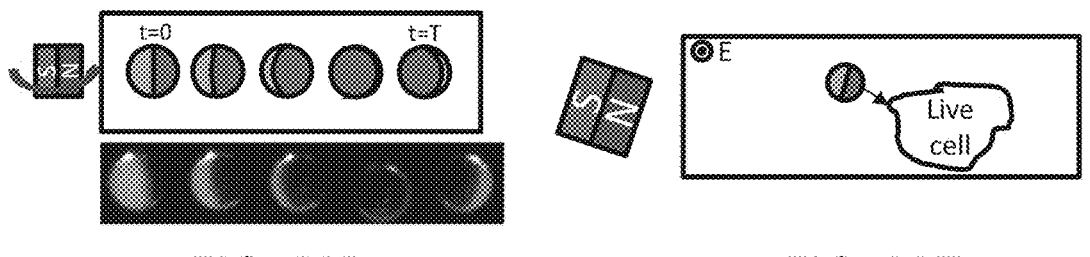
Figures 30F, 30G, 30H, 30I:
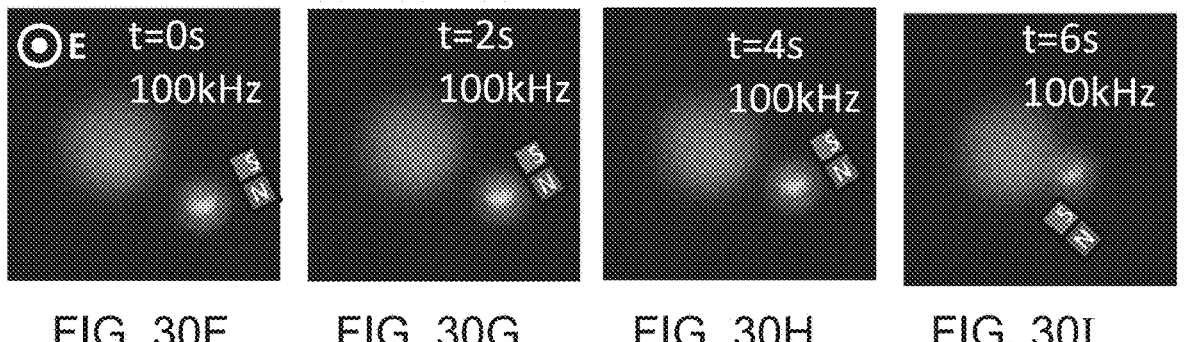

The methodology of the experiments is illustrated in FIG. 30A-I. The Janus particle is magnetized (FIGS. 30A, and 30B). The mammalian cell is approached by rotating a magnetic field (side view in FIG. 30B, microscope view in FIG. 30D). When the Janus particle is near the cell, the cell is approached by an electric field with magnetic field steering (side view in FIG. 30C, and microscope view in FIG. 30E). FIGS. 30F-I show sequential approaching the mammalian cell under 100 kHz.

FIG. 31A shows 3D reconstructed Janus particle and mammalian cell, and FIG. 31B shows electric field surface plots and streamlines around the Janus particle.

Viability fluorescent marker (CFDA) decrease with time for JP approached and non-approached mammalian cell, are shows in FIGS. 32 and 33A-F. FIG. 32 shows normalized CFDA fluorescent intensity of both JP approached and non-approached cells, and FIGS. 33A-F are microscopy images of JP approached and non-approached cells.

Local electroporation of Propidium iodide (PI) into a mammalian cell by a Janus particle is shown in FIGS.

Figures 34B, 34C:
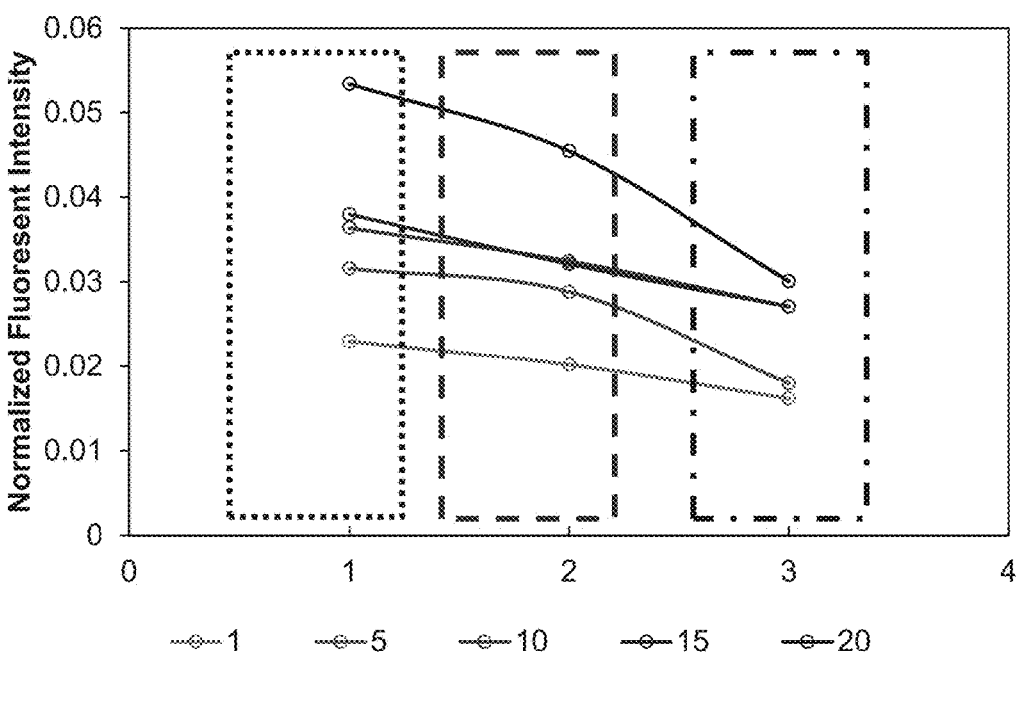

34A-C. FIG. 34A demonstrates a cell that is divided into three interrogation regions based on the distance to the JP: yellow, blue and red. FIG. 34B shows the normalized fluorescent intensity of the three regions at varying times. (C) Microscope images of the entire local electroporation process from when the JP approaches a cell (t=0) until the cell is electroporated (t=173 s).

Example 5

Non-Spherical Carrier Particle

Figure 35:
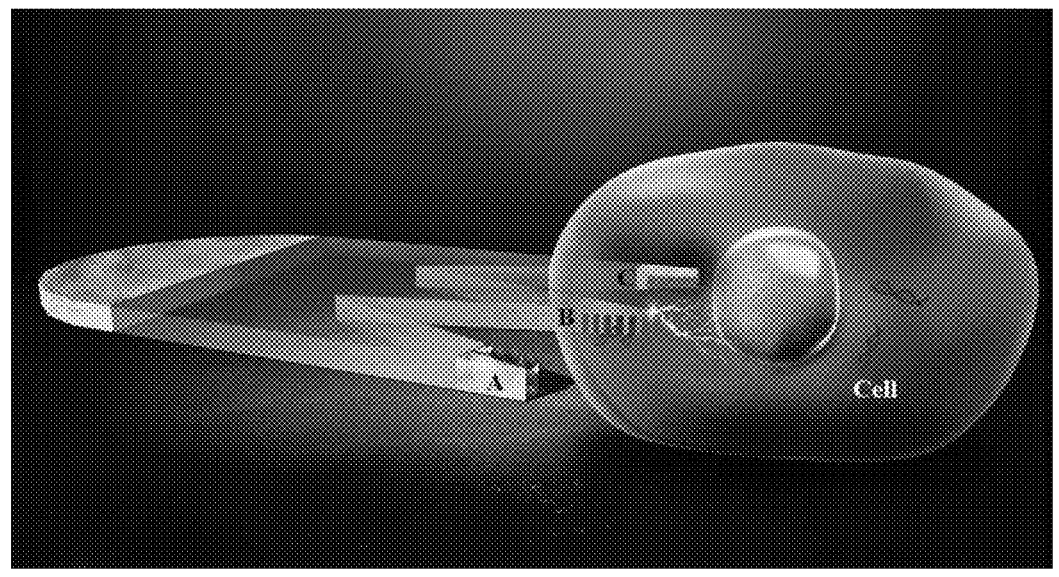
FIG. 35 is a schematic illustration of a non-spherical carrier particle approaching a cell, according to some embodiments of the present invention.

FIG. 35 is a schematic illustration of a non-spherical carrier particle which can be used according to some embodiments of the present invention. In the present example, the non-spherical carrier particle approaches a cell, but it can be used for trapping, transporting and/or electroporation of any object. The carrier particle of this example includes discrete metallic patches that can be used according to some embodiments of the present invention for carrier propulsion and/or micro or nanoscale cargo loading. In FIG. 35 a semi-circular metallic patch at the rear part of the carrier particle (left side of the FIG. 35) is designed and constructed for propulsion. Metallic coated ends at the opposite side of the semi-circular metallic patch are geometrical features designed and constructed for trapping the object. In this Example, three geometrical features are shows: a funnel (A), posts (B), and a vertical gap (C). The geometrical features allow control over the location, size and intensity of the induced electric field gradients. In addition, the carrier particle locally intensifies the electric field, resulting in local cell electroporation at a sub-cellular precision for efficient delivery of the transported cargo. Also shown in FIG. 35 is a cell approached and trapped by the carrier particle. The carrier particle can be navigated, for example, under a microscope to a specific region of the cell thereby allowing location-specific electroporation, or electrodeformation.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. A method of electroporation of a biological object, comprising:
   introducing a carrier particle into a medium containing the biological object;
   applying a first electric field to said medium at a frequency, amplitude, and/or pulse parameter selected to induce trapping of the biological object by said carrier particle; and
   varying at least said amplitude parameter so as to induce electroporation of the biological object.

2. The method of claim 1, comprising applying an electric field pulse train, in addition to said first electric field.

3. The method according to claim 1, wherein said trapping is by positive dielectrophoresis.

4. The method according to claim 1, wherein said trapping is by negative dielectrophoresis.

5. The method according to claim 1, further comprising, following said trapping and prior to said electroporation, transporting said carrier particle and the biological object to an electroporation location.

6. The method according to claim 1, further comprising, following said trapping and prior to said electroporation, varying a speed of said carrier particle.

7. The method according to claim 6, wherein said varying said speed is to a speed of zero.

8. The method according to claim 5, wherein said transporting comprises varying said first electric field to induce induced-charge electrophoresis or self-dielectrophoresis on said carrier particle.

9. The method according to claim 5, wherein the carrier particle comprises a magnetic coating or a magnetic core.

10. The method according to claim 5, wherein said transporting comprises applying a magnetic force or an optical field to said carrier particle.

11. The method according to claim 1, wherein said carrier particle is a homogenous particle.

12. The method according to claim 1, wherein said carrier particle is a symmetry broken particle, optionally wherein said symmetry broken particle is a Janus particle.

13. The method according to claim 1, wherein the biological object comprises at least one object selected from the group consisting of a bacterium, a virus, a mammalian cell, and an organelle of a biological cell.

14. The method according to claim 1, further comprising varying said electric field to deform the shape of the biological object, and probe at least one mechanical property thereof.

* * * * *